United States Patent
Liu et al.

(10) Patent No.: US 9,981,970 B2
(45) Date of Patent: May 29, 2018

(54) BICYCLIC UREAS AND THIADIAZOLIDINE-1,1-DIOXIDES AS CETP INHIBITORS

(71) Applicants: Jian Liu, Edison, NJ (US); Pengcheng Patrick Shao, Fanwood, NJ (US); Arto K. Krikorian, Astoria, NY (US); Petr Vachal, Summit, NJ (US)

(72) Inventors: Jian Liu, Edison, NJ (US); Pengcheng Patrick Shao, Fanwood, NJ (US); Arto K. Krikorian, Astoria, NY (US); Petr Vachal, Summit, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 9 days.

(21) Appl. No.: 14/908,180

(22) PCT Filed: Jul. 28, 2014

(86) PCT No.: PCT/US2014/048353
§ 371 (c)(1),
(2) Date: Jan. 28, 2016

(87) PCT Pub. No.: WO2015/017302
PCT Pub. Date: Feb. 5, 2015

(65) Prior Publication Data
US 2016/0185784 A1   Jun. 30, 2016

Related U.S. Application Data

(60) Provisional application No. 61/859,981, filed on Jul. 30, 2013.

(51) Int. Cl.
| | |
|---|---|
| *C07D 487/04* | (2006.01) |
| *A61K 45/06* | (2006.01) |
| *A61K 31/519* | (2006.01) |
| *A61K 31/714* | (2006.01) |
| *A61K 31/4439* | (2006.01) |
| *C07D 513/04* | (2006.01) |
| *A61K 31/4188* | (2006.01) |

(52) U.S. Cl.
CPC ........ *C07D 487/04* (2013.01); *A61K 31/4188* (2013.01); *A61K 31/4439* (2013.01); *A61K 31/519* (2013.01); *A61K 31/714* (2013.01); *A61K 45/06* (2013.01); *C07D 513/04* (2013.01)

(58) Field of Classification Search
None
See application file for complete search history.

(56) References Cited

U.S. PATENT DOCUMENTS

| | | |
|---|---|---|
| 3,886,177 A | 5/1975 | Fontanella et al. |
| 7,652,049 B2 | 1/2010 | Ali et al. |
| 7,737,295 B2 | 6/2010 | Ali et al. |
| 7,781,426 B2 | 8/2010 | Ali et al. |
| 7,910,592 B2 | 3/2011 | Ali et al. |
| 7,915,271 B2 | 3/2011 | Ali et al. |
| 8,293,721 B2 | 10/2012 | Hunt et al. |
| 8,436,028 B2 | 5/2013 | Hunt et al. |
| 8,445,480 B2 | 5/2013 | Hunt et al. |
| 8,486,983 B2 | 7/2013 | Sheth et al. |
| 8,865,707 B2 | 10/2014 | Ali et al. |
| 8,871,738 B2 | 10/2014 | Shao et al. |
| 2009/0192154 A1 | 7/2009 | Maekawara et al. |
| 2013/0331372 A1 | 12/2013 | Lu et al. |
| 2014/0357632 A1 | 12/2014 | Anand et al. |
| 2015/0111866 A1 | 4/2015 | Acton, III et al. |
| 2015/0307464 A1 | 10/2015 | Shao et al. |
| 2015/0342931 A1 | 12/2015 | Ondeyka et al. |

OTHER PUBLICATIONS

International Search Report for PCT/US2014/048353, dated Nov. 11, 2014.
Ko, et al.; Pyrrole-based Scaffolds for Turn Mimics, Org Letters, Mar. 4, 2011, pp. 1-12, vol. 13, Issue 5.
Written Opinion for PCT/US2014/048353, dated Nov. 11, 2014.

*Primary Examiner* — Sreeni Padmanabhan
*Assistant Examiner* — Jody Karol
(74) *Attorney, Agent, or Firm* — Eric A. Meade; John C. Todaro

(57) ABSTRACT

Compounds having the structure of Formula I, including pharmaceutically acceptable salts of the compounds, wherein X is —C(=O) or —S(O)$_2$—, are CETP inhibitors and are useful for raising HDL-cholesterol, reducing LDL-cholesterol, and for treating or preventing atherosclerosis.

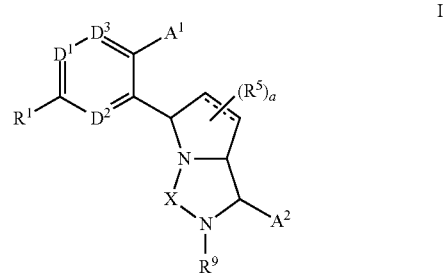

10 Claims, No Drawings

BICYCLIC UREAS AND THIADIAZOLIDINE-1, 1-DIOXIDES AS CETP INHIBITORS

CROSS-REFERENCE TO RELATED APPLICATIONS

This application is a U.S. National Phase application under 35 U.S.C. § 371 of PCT/US2014/048353, filed Jul. 28, 2014, which claims priority from U.S. provisional application No. 61/859,981 filed Jul. 30, 2013.

FIELD OF THE INVENTION

This invention relates to chemical compounds that inhibit cholesterol ester transfer protein (CETP) and are expected to have utility in raising HDL-C, lowering LDL-C, and in the treatment and prevention of atherosclerosis.

BACKGROUND OF THE INVENTION

Atherosclerosis and its clinical consequences, including coronary heart disease (CHD), stroke and peripheral vascular disease, represent a truly enormous burden to the health care systems of the industrialized world. In the United States alone, approximately 13 million patients have been diagnosed with CHD, and greater than one half million deaths are attributed to CHD each year. Further, this toll is expected to grow over the next quarter century as an epidemic in obesity and diabetes continues to grow.

It has long been recognized that in mammals, variations in circulating lipoprotein profiles correlate with the risk of atherosclerosis and CHD. The clinical success of HMG-CoA reductase inhibitors, especially the statins, in reducing coronary events is based on the reduction of circulating low density lipoprotein cholesterol (LDL-C), levels of which correlate directly with an increased risk for atherosclerosis. More recently, epidemiologic studies have demonstrated an inverse relationship between high density lipoprotein cholesterol (HDL-C) levels and atherosclerosis, leading to the conclusion that low serum HDL-C levels are associated with an increased risk for CHD.

Metabolic control of lipoprotein levels is a complex and dynamic process involving many factors. One important metabolic control in man is the cholesteryl ester transfer protein (CETP), a plasma glycoprotein that catalyzes the movement of cholesteryl esters from HDL to the apoB containing lipoproteins, especially VLDL (see Hesler, C. B., et. al. (1987) *Purification and characterization of human plasma cholesteryl ester transfer protein. J. Biol. Chem.* 262(5), 2275-2282)). Under physiological conditions, the net reaction is a heteroexchange in which CETP carries triglyceride to HDL from the apoB lipoprotein and transports cholesterol ester from HDL to the apoB lipoprotein.

In humans, CETP plays a role in reverse cholesterol transport, the process whereby cholesterol is returned to the liver from peripheral tissues. Intriguingly, many animals do not possess CETP, including animals that have high HDL levels and are known to be resistant to coronary heart disease, such as rodents (see Guyard-Dangremont, V., et. al., (1998) *Phospholipid* and *cholesteryl ester transfer activities in plasma from 14 vertebrate species. Relation to atherogenesis susceptibility, Comp. Biochem. Physiol. B Biochem. Mol. Biol.* 120(3), 517-525). Numerous epidemiologic studies correlating the effects of natural variation in CETP activity with respect to coronary heart disease risk have been performed, including studies on a small number of known human null mutations (see Hirano, K.-I., Yamashita, S. and Matsuzawa, Y. (2000) *Pros and cons of inhibiting cholesteryl ester transfer protein, Curr. Opin. Lipidol.* 11(6), 589-596). These studies have clearly demonstrated an inverse correlation between plasma HDL-C concentration and CETP activity (see Inazu, A., et. al. (2000) *Cholesteryl ester transfer protein and atherosclerosis, Curr. Opin. Lipidol.* 11(4), 389-396), leading to the hypothesis that pharmacologic inhibition of CETP lipid transfer activity may be beneficial to humans by increasing levels of HDL-C while lowering LDL-C.

Despite the significant therapeutic advance that statins such as simvastatin and atorvastatin represent, statins only achieve a risk reduction of approximately one-third in the treatment and prevention of atherosclerosis and ensuing atherosclerotic disease events. Currently, few pharmacologic therapies are available that favorably raise circulating levels of HDL-C. Certain statins and some fibrates offer modest HDL-C gains. Niacin provides an effective therapy for raising HDL-C but suffers from patient compliance issues, due in part to side effects such as flushing. Drugs that inhibit CETP (CETP inhibitors) have been under development with the expectation that they will effectively raise HDL cholesterol levels and also reduce the incidence of atherosclerosis in patients. Torcetrapib was the first drug that was tested in a long-term outcomes clinical trial. The clinical trial of torcetrapib was terminated early due to a higher incidence of mortality in patients to whom torcetrapib and atorvastatin were administered concomitantly compared with patients who were treated with atorvastatin alone. The cause of the increased mortality is not completely understood, but it is not believed to be associated with the CETP inhibiting effects of the drug. Dalcetrapib was recently tested in a Phase III outcomes trial, which was terminated early because the interim data did not show a clinical benefit. There were no safety issues detected for dalcetrapib.

Anacetrapib is currently the only CETP inhibitor being tested in a large scale Phase III clinical outcomes trial. Data from the recently completed DEFINE Phase II/III trial of anacetrapib are promising. Patients who were treated with anacetrapib along with baseline statin therapy showed an increase of HDL-C of 138% and a decrease of LDL-C of 40% compared with patients who were treated with just a statin. See: *N. Engl. J. Med.* 2010: 363: 2406-15. The DEFINE study was not carried out on a large enough scale to serve as a pivotal outcomes trial, but the data in the DEFINE trial were sufficient to indicate that an increase in mortality for patients treated with anacetrapib is unlikely. Additional drug candidates are in development. Evacetrapib currently appears to be the next CETP inhibitor that will proceed to a Phase III outcomes trial. Additional compounds are being sought that may have properties that are advantageous compared with the CETP inhibitors that have so far been studied or are currently being studied. Such properties may include, for example, higher potency, reduced off-target activity, better pharmacodynamics, higher bioavailability, or a reduced food effect compared with many of the highly lipophilic compounds that have so far been studied. "Food effect" refers to the variability in exposure to the active drug that occurs depending on when the patient had last eaten, whether or not the drug is administered with food, and the fat content of the food.

SUMMARY OF THE INVENTION

The compound of Formula I, or a pharmaceutically acceptable salt thereof, is a potent CETP inhibitor, having the utilities described herein:

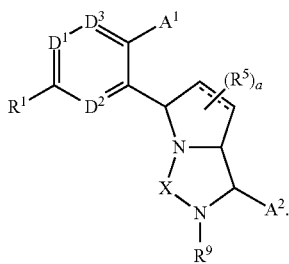

I wherein X is —C(═O)—, —S(O)₂—, —C(═S)—, or —C(═NR), wherein R is H, —CN, —C₁-C₅ alkyl, phenyl, C₃₋₆ cycloalkyl optionally having 1-2 double bonds, or HET(3), wherein when R is phenyl, C₃₋₆ cycloalkyl, or HET(3), R is optionally substituted with 1-5 substituent groups which are each independently halogen, —CN, —C₁-C₄ alkyl optionally substituted with 1-5 halogens, —OC₁-C₄ alkyl optionally substituted with 1-5 halogens, C₃₋₆ cycloalkyl optionally substituted with 1-5 halogens, —NR⁶R⁷, —CO₂R⁸, —C(O)NR⁶R⁷, or —SO₂NR⁶R⁷, and when R is —C₁-C₅ alkyl or —OC₁-C₅ alkyl, R is optionally substituted with 1-5 substituent groups which are independently halogen, —OC₁-C₄ alkyl optionally substituted with 1-5 halogens, —CN, C₃₋₆ cycloalkyl optionally substituted with 1-5 halogens, —NR⁶R⁷, —CO₂R⁸, —C(O)NR⁶R⁷, or —SO₂NR⁶R⁷;

R¹ is H, —C₁-C₅ alkyl, —OC₁-C₅ alkyl, —C₂-C₅ alkenyl, —OC₂-C₅ alkenyl, —C₂-C₅ alkynyl, —OC₂-C₅ alkynyl, —OH, halogen, —CN, —NR⁶R⁷, —CO₂R⁸, —C(O)NR⁶R⁷, —SO₂NR⁶R⁷, HET(3), or C₃₋₆ cycloalkyl optionally having 1-2 double bonds, wherein —C₁-C₅ alkyl, —OC₁-C₅ alkyl, —C₂-C₅ alkenyl, —OC₂-C₅ alkenyl, —C₂-C₅ alkynyl, and —OC₂-C₅ alkynyl are each optionally substituted with 1-7 halogens, and wherein HET(3) and C₃₋₆ cycloalkyl optionally having 1-2 double bonds are optionally substituted with 1-3 substituent groups which are each independently halogen, —C₁-C₃ alkyl, —OC₁-C₃ alkyl, —C₁-C₃ alkenyl, —OC₂-C₃ alkenyl, —C₂-C₃ alkynyl, or —OC₂-C₃ alkynyl, wherein —C₁-C₃ alkyl, —OC₁-C₃ alkyl, —C₂-C₃ alkenyl, —OC₂-C₃ alkenyl, —C₂-C₃alkynyl, and —OC₂-C₃ alkynyl are each optionally substituted with 1-7 halogens;

R⁶ and R⁷ are each independently H, —C₁-C₅ alkyl, phenyl, naphthyl, C₃₋₆ cycloalkyl optionally having 1-2 double bonds, or HET(3), wherein phenyl, naphthyl, C₃₋₆ cycloalkyl, and HET(3) are optionally substituted with 1-3 substituent groups which are each independently halogen, —C₁-C₃ alkyl, —OC₁-C₃ alkyl, —C₂-C₃ alkenyl, —OC₂-C₃ alkenyl, —C₂-C₃ alkynyl, or —OC₂-C₃ alkynyl, wherein —C₁-C₃ alkyl, —OC₁-C₃ alkyl, —C₂-C₃ alkenyl, —OC₂-C₃ alkenyl, —C₂-C₃alkynyl, and —OC₂-C₃ alkynyl are each optionally substituted with 1-7 halogens;

R⁸ is H or —C₁₋₅alkyl optionally substituted with 1-7 halogens;

R⁹ is H or —C₁₋₅alkyl optionally substituted with 1-7 halogens;

HET(3) is a 3-6 membered heterocyclic ring having 1-3 heteroatom groups which are each independently N, NH, O, S, S(O), or S(O)₂ and optionally having 1-3 double bonds;

The dashed line in Formula I represents an optional double bond;

D¹ is N or CR²;
D² is N or CR³;
D³ is N or CR⁴;

R², R³, and R⁴ are each independently H, —C₁-C₅ alkyl, —OC₁-C₅ alkyl, —C₂-C₅ alkenyl, —OC₂-C₅ alkenyl, —C₂-C₅ alkynyl, —OC₂-C₅ alkynyl, —OH, halogen, —CN, —NR⁶R⁷, —CO₂R⁸, —C(O)NR⁶R⁷, or —SO₂NR⁶R⁷, wherein —C₁-C₅ alkyl, —OC₁-C₅ alkyl, —C₁-C₅ alkenyl, —OC₂-C₅ alkenyl, —C₁-C₅ alkynyl, and —OC₂-C₅ alkynyl are optionally substituted with 1-7 halogens;

Each R⁵ is independently —C₁-C₅ alkyl, —OC₁-C₅ alkyl, —C₂-C₅ alkenyl, —OC₂-C₅ alkenyl, —C₂-C₅ alkynyl, —OC₂-C₅ alkynyl, —OH, halogen, —CN, —NR⁶R⁷, —CO₂R⁸, —C(O)NR⁶R⁷, or —SO₂NR⁶R⁷, wherein —C₁-C₅ alkyl, —OC₁-C₅ alkyl, —C₂-C₅ alkenyl, —OC₂-C₅ alkenyl, —C₂-C₅ alkynyl, and —OC₂-C₅ alkynyl are optionally substituted with 1-7 halogens;

A¹ is phenyl, HET(1), or C₃-C₈ cycloalkyl optionally having 1-2 double bonds, wherein A¹ is optionally substituted with one substituent group Z and is optionally substituted with 1-3 groups which are each independently —C₁-C₅ alkyl, —OC₁-C₅ alkyl, —C₂-C₅ alkenyl, —OC₂-C₅ alkenyl, —C₁-C₅ alkynyl, —OC₂-C₅ alkynyl, halogen, —OH, or —CN, wherein —C₁-C₅ alkyl, —OC₁-C₅ alkyl, —C₂-C₅ alkenyl, —OC₂-C₅ alkenyl, —C₂-C₅ alkynyl, and —OC₂-C₅ alkynyl are optionally substituted with 1-7 halogens;

HET(1) is a 5- or 6-membered heterocyclic ring having 1-4 heteroatom groups which are each independently —N—, —NH—, —S—, —O—, —S(O)—, or —S(O)₂—, optionally having one group —C(═O)—, and optionally having 1-3 double bonds;

Z is A³, —C₁-C₃ alkylene-CO₂R⁸, —C₁-C₃ alkylene-C(O)NR⁶R⁷, —C₁-C₃ alkylene-SO₂NR⁶R⁷, —CO₂R⁸, —C(O)NR⁶R⁷, —SO₂NR⁶R⁷, or —C₁-C₃alkylene-HET(2), wherein —C₁-C₃alkylene in all uses is optionally substituted with 1-7 halogens, and HET(2) is optionally substituted with 1-3 substituents which are independently —C₁-C₃ alkyl optionally substituted with 1-5 halogens, —OC₁₋₃ alkyl optionally substituted with 1-5 halogens, halogen or NR⁶R⁷;

A³ is phenyl, C₃-C₆ cycloalkyl optionally having 1-2 double bonds, or HET(1), wherein A³ is optionally substituted with 1-3 groups which are each independently —C₁-C₅ alkyl, —OC₁-C₅ alkyl, —C₂-C₅ alkenyl, —OC₂-C₅ alkenyl, —C₂-C₅ alkynyl, —OC₂-C₅ alkynyl, halogen, —OH, or —CN, wherein —C₁-C₅ alkyl, —OC₁-C₅ alkyl, —C₂-C₅ alkenyl, —OC₂-C₅ alkenyl, —C₂-C₅ alkynyl, and —OC₂-C₅ alkynyl are optionally substituted with 1-7 halogens; and A³ is optionally substituted with one group which is HET(2), —C₁₋₄ alkylene-CO₂R⁸, —C₁₋₄alkylene-C(O)NR⁶R⁷, —C₁-C₄alkylene-SO₂NR⁶R⁷, —CO₂R⁸, —C(O)NR⁶R⁷, —SO₂NR⁶R⁷, or —C(O)NR⁶C₃₋₆cycloalkyl in which C₃₋₆cycloalkyl is optionally substituted with 1-3 substituents which are independently selected from halogen, C₁₋₂ alkyl, and —CN, wherein —C₁-C₄alkylene in all uses is optionally substituted with 1-7 halogens; and wherein HET(2) is optionally substituted with 1-3 groups which are each independently halogen, —C₁₋₅ alkyl optionally substituted with 1-7 halogens, —OC₁₋₅alkyl optionally substituted with 1-7 halogens, or NR⁶R⁷;

HET(2) is a 5-6 membered heterocyclic ring having 1-3 heteroatom groups which are each independently N, NH, O, or S, optionally having one group —C(═O)—, and optionally having 1-3 double bonds;

A² is phenyl or HET(1), wherein A² is optionally substituted with 1-3 substituent groups which are each independently —C₁-C₅ alkyl, —OC₁-C₅ alkyl, —C₂-C₅ alkenyl, —OC₂-C₅ alkenyl, —C₂-C₅alkynyl, —OC₂-C₅alkynyl, halogen, —CN, —OH, or C₃₋₆cycloalkyl, wherein —C₁-C₅ alkyl, —$OC_1$-$C_5$ alkyl, —$C_2$-$C_5$ alkenyl, —$OC_2$-$C_5$ alkenyl, —$C_2$-$C_5$alkynyl, and —$OC_2$-$C_5$ alkynyl are optionally substituted with 1-7 halogens, and $C_{3-6}$cycloalkyl is optionally substituted with 1-3 substituents which are each independently halogen, —$C_1$-$C_3$ alkyl, or —$OC_1$-$C_3$ alkyl, wherein-$C_1$-$C_3$ alkyl and —$OC_1$-$C_3$ alkyl are each optionally substituted with 1-7 halogens; and a is 0 or an integer from 1-3.

DETAILED DESCRIPTION OF THE INVENTION

In further embodiments of the invention, the substituent groups defined above may have alternative values independent of one another, as written below. Such embodiments include pharmaceutically acceptable salts where such salts are possible.

In some embodiments, $R^1$ is —$C_1$-$C_5$ alkyl, —$OC_1$-$C_5$ alkyl, halogen, —$NR^6R^7$, HET(3), or $C_{3-6}$ cycloalkyl optionally having 1-2 double bonds, wherein —$C_1$-$C_5$ alkyl and —$OC_1$-$C_5$ alkyl are optionally substituted with 1-7 halogens, and wherein HET(3) and $C_{3-6}$ cycloalkyl optionally having 1-2 double bonds are optionally substituted with 1-3 substituent groups which are each independently halogen, $CH_3$, $CF_3$, $OCH_3$, or $OCF_3$.

In some embodiments, $R^1$ is $CH_3$, $CF_3$, —$OCH_3$, —$OCF_3$, halogen, or —$NR^6R^7$.

In some embodiments, at least one of $D^1$, $D^2$, and $D^3$ is $CR^2$, $CR^3$, or $CR^4$, where $R^2$, $R^3$, and $R^4$ are each independently H, —$C_1$-$C_5$ alkyl, —$OC_1$-$C_5$ alkyl, or halogen, wherein —$C_1$-$C_5$ alkyl and —$OC_1$-$C_5$ alkyl are optionally substituted with 1-7 halogens.

In some embodiments, $R^2$, $R^3$, and $R^4$ are each independently H, $C_{1-3}$alkyl, $CF_3$, —$OC_{1-3}$ alkyl, —$OCF_3$, or halogen.

In some embodiments, each $R^5$ is independently —$C_1$-$C_5$ alkyl, —$OC_1$-$C_5$ alkyl, or halogen, where —$C_1$-$C_5$ alkyl and —$OC_1$-$C_5$ alkyl are optionally substituted with 1-7 halogens.

In some embodiments, $R^5$ is independently $CH_3$, $CF_3$, —$OCH_3$, —$OCF_3$, or halogen.

In some embodiments, $R^6$ and $R^7$ are each independently H or —$C_1$-$C_5$ alkyl.

In some embodiments, $R^6$ and $R^7$ are each independently H or —$C_1$-$C_3$ alkyl.

In some embodiments, $R^6$ and $R^7$ are each independently H or —$CH_3$.

In some embodiments, $R^8$ is H or —$C_{1-3}$alkyl optionally substituted with 1-3 halogens.

In some embodiments, $R^8$ is H or —$CH_3$.
In some embodiments, $R^9$ is H or —$C_{1-5}$alkyl.
In some embodiments, $R^9$ is H or —$C_{1-3}$alkyl.
In some embodiments, $R^9$ is H or —$CH_3$.

In some embodiments, $A^1$ is phenyl, HET(1), or $C_3$-$C_6$ cycloalkyl optionally having 1-2 double bonds, where $A^1$ is optionally substituted with one substituent group Z and is optionally substituted with 1-3 groups which are each independently halogen, —OH, —CN, —$C_{1-5}$alkyl optionally substituted with 1-7 halogens, or —$OC_{1-5}$alkyl optionally substituted with 1-7 halogens.

In some embodiments, $A^1$ is phenyl, HET(1), or $C_3$-$C_6$ cycloalkyl optionally having 1-2 double bonds, wherein $A^1$ is optionally substituted with one substituent group Z and is optionally substituted with 1-3 groups which are each independently —$C_{1-3}$alkyl optionally substituted with 1-5 halogens, —$OC_{1-3}$alkyl optionally substituted with 1-5 halogens, halogen, —OH, or —CN.

In some embodiments, each HET(1) is a 5- or 6-membered heterocyclic ring having 1-3 heteroatom groups which are each independently —N—, —NH—, —S—, or —O—, optionally having one group —C(=O)—, and optionally having 1-3 double bonds.

In some embodiments, Z is $A^3$, —$(CH_2)_{1-3}$—$CO_2R^8$, —$(CH_2)_{1-3}$—$C(O)NR^6R^7$, —$(CH_2)_{1-3}$—$SO_2NR^6R^7$, —$CO_2R^8$, —$C(O)NR^6R^7$, —$SO_2NR^6R^7$, or —$(CH_2)_{1-3}$-HET(2), where HET(2) is optionally substituted with 1-3 substituents which are independently —$C_1$-$C_3$ alkyl optionally substituted with 1-5 halogens, —$OC_{1-3}$ alkyl optionally substituted with 1-5 halogens, halogen or $NR^6R^7$.

In some embodiments, $A^3$ is phenyl, $C_3$-$C_6$ cycloalkyl optionally having 1-2 double bonds, or HET(1), where $A^3$ is optionally substituted with 1-3 groups which are each independently —$C_1$-$C_5$ alkyl optionally substituted with 1-7 halogens, —$OC_1$-$C_5$ alkyl optionally substituted with 1-7 halogens, —OH, or halogen, and is optionally substituted with one group which is HET(2), —$C_{1-2}$ alkylene-$CO_2R^8$, —$C_{1-2}$alkylene-$C(O)NR^6R^7$, —$C_1$-$C_2$alkylene-$SO_2NR^6R^7$, —$CO_2R^8$, —$C(O)NR^6R^7$, —$SO_2NR^6R^7$, or —$C(O)NR^6C_{3-6}$cycloalkyl wherein $C_{3-6}$cycloalkyl is optionally substituted with 1-3 substituents which are independently selected from halogen, $C_{1-2}$alkyl, and —CN, wherein —$C_1$-$C_2$alkylene is optionally substituted with 1-3 halogens; and wherein HET(2) is optionally substituted with 1-3 groups which are each independently halogen, —$C_{1-5}$ alkyl optionally substituted with 1-7 halogens, —$OC_{1-5}$alkyl optionally substituted with 1-7 halogens, or $NR^6R^7$.

In some embodiments, $A^3$ is phenyl, $C_3$-$C_6$ cycloalkyl optionally having 1-2 double bonds, or HET(1), wherein $A^3$ is optionally substituted with 1-3 groups which are each independently $CH_3$, $CF_3$, —$OCH_3$, —$OCF_3$, —OH, or halogen, and is optionally substituted with one group which is HET(2), —$(CH_2)_{1-2}$—$CO_2R^8$, —$(CH_2)_{1-2}$—$C(O)NR^6R^7$, —$(CH_2)_{1-2}$—$SO_2NR^6R^7$, —$CO_2R^8$, —$C(O)NR^6R^7$, —$SO_2NR^6R^7$, or —$C(O)NR^6$cyclopropyl, wherein cyclopropyl is optionally substituted with 1-3 substituents which are independently selected from 1-3 halogens, one $CH_3$, and one —CN, and HET(2) is optionally substituted with 1-3 groups which are each independently $CH_3$, $CF_3$, —$OCH_3$, —$OCF_3$, halogen, or $NR^6R^7$.

In some embodiments, $A^2$ is phenyl or HET(1), where $A^2$ is optionally substituted with 1-3 substituent groups which are each independently $C_1$-$C_5$ alkyl optionally substituted with 1-7 halogens, —$OC_{1-5}$alkyl optionally substituted with 1-7 halogens, halogen, —OH, —CN, or $C_{3-6}$cycloalkyl optionally substituted with 1-3 substituents which are each independently halogen, $CF_3$, $CH_3$, —$OCF_3$, or —$OCH_3$.

In some embodiments, $A^2$ is phenyl or HET(1), wherein $A^2$ is substituted with 1-3 substituent groups which are each independently $CH_3$, $CF_3$, —$OCH_3$, —$OCF_3$, halogen, —CN, —OH, or $C_{3-4}$cycloalkyl optionally substituted with 1-3 substituents which are each independently halogen, $CF_3$, $CH_3$, —$OCF_3$, or —$OCH_3$.

In some embodiments, a is 0, 1, or 2.
In some embodiments, $R^1$ is $CH_3$, $CF_3$, —$OCH_3$, —$OCF_3$, F, Cl, or —$NR^6R^7$.
In some embodiments, $D^1$ is N or $CR^2$, wherein $R^2$ is H, —$C_{1-3}$alkyl, F, or Cl.
In some embodiments, $D^2$ is N or $CR^3$, wherein $R^3$ is H, —$C_{1-3}$alkyl, F, or Cl.
In some embodiments, $D^3$ is N or $CR^4$, wherein $R^4$ is H, —$C_1$-$C_3$ alkyl, F, or Cl.
In some embodiments, at least one of $D^1$, $D^2$, or $D^3$ is $CR^2$, $CR^3$, or $CR^4$.
In some embodiments, $R^5$ is H or $CH_3$.

In some embodiments, A¹ is phenyl, pyridinyl, pyrazinyl, pyrimidinyl, pyridazinyl, pyrazolyl, imidazolyl, isoxazolyl, thiazolyl, oxadiazolyl, thiadiazolyl, oxazolyl, pyrrolyl, thienyl, furyl, cyclopropyl, cyclobutyl, cyclohexyl, cyclohexenyl, cyclopentyl, or cyclopentenyl, wherein A¹ is optionally substituted with 1-3 groups which are each independently F, Cl, —OCH$_3$, —OCF$_3$, —C$_{1-3}$alkyl, —CN, or CF$_3$, and optionally one substituent group Z.

In some embodiments, Z is A³, —CH$_2$CH$_2$CO$_2$R⁸, —CH$_2$CH$_2$C(O)NR⁶R⁷, —CH$_2$CH$_2$SO$_2$NR⁶R⁷, or —CH$_2$CH$_2$-HET(2), wherein HET(2) is optionally substituted with 1-2 substituent groups which are each independently CH$_3$, CF$_3$, —OCH$_3$, —OCF$_3$, halogen, or NR⁶R⁷.

In some embodiments, R⁸ is H or —CH$_3$.
In some embodiments, R⁹ is H or —CH$_3$.
In some embodiments, HET(2) is a 5-membered heterocyclic ring having 1-3 heteroatom groups which are each independently N, NH, O, or S, optionally having one group —C(=O), and optionally having 1-3 double bonds.

In some embodiments, A³ is phenyl, cyclopropyl, cyclobutyl, cyclohexyl, cyclohexenyl, cyclopentyl, cyclopentenyl, or HET(1), wherein HET(1) is pyridinyl, pyrazinyl, pyrimidinyl, pyridazinyl, pyrazolyl, imidazolyl, isoxazolyl, thiazolyl, oxadiazolyl, thiadiazolyl, oxazolyl, pyrrolyl, thienyl, furyl, or a 5-6-membered heterocyclic ring having 1-2 heteroatom groups which are independently —N—, —NH— or —O—, and optionally one —C(=O)— group, wherein A³ is optionally substituted with 1-2 groups which are each independently CH$_3$, CF$_3$, —OCH$_3$, —OCF$_3$, —OH, or halogen, and is optionally substituted with 1 group which is —CO$_2$R⁸, —C(O)NR⁶R⁷, —SO$_2$NR⁶R⁷, HET(2), or —C(O)NR⁶cyclopropyl wherein cyclopropyl is optionally substituted with 1-3 substituents which are independently selected from 1-3 halogens, one CH$_3$ and one —CN, and HET(2) is optionally substituted with 1-2 substituent groups which are each independently CH$_3$, CF$_3$, —OCH$_3$, —OCF$_3$, halogen, or NR⁶R⁷.

In some embodiments, A² is phenyl or HET(1) wherein A² is substituted with 1-3 substituent groups which are each independently CF$_3$, CH$_3$, F, Cl, —CN, or cyclopropyl.

In some embodiments, a is 0 or 1.
In some embodiments, a is 0.
In some embodiments, the compound has Formula 1a, including pharmaceutically acceptable salts thereof.

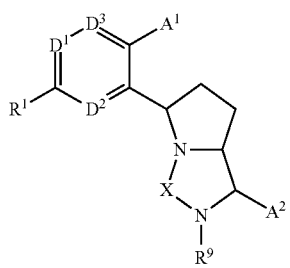

Ia

The substituent groups defined above can also used with Formula Ia.

The substituent groups as defined below can used with Formula I or Ia.

In some embodiments, R¹ is CF$_3$, F, or —N(CH$_3$)$_2$.
In some embodiments, D¹ is N or CR², wherein R² is H or C$_{1-3}$alkyl.
In some embodiments, D² is N or CR³, wherein R³ is H or CH$_3$.

In some embodiments, D³ is N or CR⁴, wherein R⁴ is H or CH$_3$.

In some embodiments, A¹ is phenyl, pyridinyl, thienyl, furyl, cyclohexenyl, or cyclopentenyl, wherein A¹ is optionally substituted with 1-3 groups which are each independently F, Cl, —OCH$_3$, isopropyl, —CN, —CH$_3$, or CF$_3$, and optionally one substituent group Z.

In some embodiments, Z is A³, —CH$_2$CH$_2$CO$_2$R⁸, —CH$_2$CH$_2$-(5-oxo-4,5-dihydro-1,3,4-oxadiazol-2-yl), or —CH$_2$CH$_2$-(5-amino-1,3,4-oxadiazol-2-yl).

In some embodiments, R⁸ is H or —CH$_3$.
In some embodiments, R⁹ is H or —CH$_3$.
In some embodiments, A³ is phenyl, cyclobutyl, cyclopentyl, cyclohexyl, or HET(1), wherein HET(1) is pyridinyl, 6-oxopiperidinyl, 2-oxo-1,3-oxazolidinyl, 2-oxo-1,3-oxazinanyl, 5-oxopyrrolidinyl, -(5-oxo-4,5-dihydro-1,3,4-oxadiazol-2-yl), or -(5-amino-1,3,4-oxadiazol-2-yl) wherein A³ is optionally substituted with 1-2 groups —CH$_3$, —OCH$_3$, or —OH, and is optionally substituted with 1 group which is —CO$_2$R⁸ or —C(=O)NHcyclopropyl which is optionally substituted with 1-3 groups independently selected from one —CN and 1-3 halogens.

In some embodiments, A² is phenyl or pyridinyl, wherein A² is substituted with 1 or 2 groups which are each independently CF$_3$, CH$_3$, F, or Cl.

In some embodiments, R¹ is CF$_3$.
In some embodiments, D¹ is N or CR², wherein R² is H.
In some embodiments, D² is CR³, wherein R³ is H.
In some embodiments, D³ is CR⁴, wherein R⁴ is H.
In some embodiments, A¹ is phenyl or pyridinyl, wherein A¹ is optionally substituted with 1-3 groups which are each independently F, —OCH$_3$, or isopropyl, and optionally one substituent group Z.

In some embodiments, Z is A³ or —CH$_2$CH$_2$CO$_2$R⁸.
In some embodiments, R⁸ is H or —CH$_3$.
In some embodiments, R⁹ is H or —C$_{1-5}$alkyl;
In some embodiments, A³ is phenyl, cyclohexyl, or HET (1), wherein HET(1) is pyridinyl or 5-oxopyrrolidinyl, wherein A³ is optionally substituted with 1-2 groups —CH$_3$ and is optionally substituted with 1 group which is —CO$_2$R⁸ or —C(=O)NHcyclopropyl which has a geminal —CN substituent on the cyclopropyl ring.

In some embodiments, A² is phenyl or pyridinyl, wherein A² is substituted with 1-2 groups which are selected from CF$_3$ and F.

In many embodiments, X is —C(=O)— or —S(O)$_2$—,
In many embodiments, X is —C(=O)—.
In many embodiments, X is —S(O)$_2$—.

In the compound of formula I and formula Ia (defined above) and in subgroups and other embodiments of the invention, alkyl groups and substituents based on alkyl groups, such as alkoxy, may be linear or branched unless otherwise indicated.

In general, references to the compound(s) of formula I or Ia are meant to also include subsets of compounds of formula I or Ia as may be defined herein, and also are meant to include the specific numbered examples provided herein.

Definitions and Abbreviations

"Ac" is acetyl, which is CH$_3$C(=O)—.
"AcOH" is acetic acid.
"Alkyl" means saturated carbon chains which may be linear or branched or combinations thereof, unless the carbon chain is defined otherwise. Other groups having the prefix "alk", such as alkoxy and alkanoyl, also may be linear or branched or combinations thereof, unless the carbon chain is defined otherwise. Examples of alkyl groups include methyl, ethyl, propyl, isopropyl, n-butyl, sec-butyl, tert-butyl, pentyl, hexyl, heptyl, octyl, nonyl, and the like.

"Alkylene" groups are alkyl groups that are difunctional rather than monofunctional. For example, methyl is an alkyl group and methylene (—CH$_2$—) is the corresponding alkylene group. Alkyl groups that are shown as difunctional are alkylene groups, even if they are referred to as alkyl groups.

"Alkenyl" means carbon chains which contain at least one carbon-carbon double bond, and which may be linear or branched or combinations thereof. Examples of alkenyl include vinyl, allyl, isopropenyl, pentenyl, hexenyl, heptenyl, 1-propenyl, 2-butenyl, 2-methyl-2-butenyl, and the like.

"Alkynyl" means carbon chains which contain at least one carbon-carbon triple bond, and which may be linear or branched or combinations thereof. Examples of alkynyl include ethynyl, propargyl, 3-methyl-1-pentynyl, 2-heptynyl and the like.

"Cycloalkyl" means a saturated carbocyclic ring having from 3 to 8 carbon atoms, unless otherwise stated. The term also includes a cycloalkyl ring fused to an aryl group. Examples of cycloalkyl include cyclopropyl, cyclopentyl, cyclohexyl, cycloheptyl, and the like. "Cycloalkenyl" means a non-aromatic carbocyclic ring having one or more double bonds, but less than the number of double bonds that are required for the cycloalkenyl to be aromatic.

"Aryl" when used to describe a substituent or group in a structure means a monocyclic or bicyclic compound in which the rings are aromatic and which contain only carbon ring atoms. The term "aryl" can also refer to an aryl group that is fused to a cycloalkyl or heterocycle. Preferred "aryls" are phenyl and naphthyl. Phenyl is generally the most preferred aryl group.

"Heterocycle" or "heterocyclic" means a fully or partially saturated or aromatic cyclic compound containing 1 or more heteroatom groups which may be one or more of N, S, O, S(O), S(O)$_2$, or (N)R, and may have one or more double bonds, where R is H or a substituent group. In general, when heterocycles are defined herein, the definition will include the number of ring members, the number of double bonds (if any), and the specific heteroatoms. The heterocycles in some cases will be aromatic, depending on the number of double bonds (e.g. 6-membered ring with 3 double bonds). Aromatic heterocycles are also referred to as heteroaromatics. S(O), S(O)$_2$, and N(R) are referred to as heteroatom groups, and each heteroatom group is counted as one ring member, as is also the case for N, S, and O.

"Benzoheterocycle" represents a phenyl ring fused to a heterocyclic ring. Examples include indole, benzofuran, 2,3-dihydrobenzofuran and quinoline.

"Boc" is tert-butoxycarbonyl.
"n-Bu" is n-butyl.
"t-Bu" is tert-butyl.
"Celite®" is a trade name for diatomaceous earth.
"DBU" is 1,8-diazabicyclo[5.4.0]undec-7-ene.
"D-Epoxone" is a commercial epoxidation catalyst.
"DIPEA" and "DIEA" are N,N-diisopropylethylamine.
"DCM" is dichloromethane.
"DIBAL" or "DIBAL-H" is diisobutylaluminum hydride.
"DMF" is N,N-dimethylformamide.
"DMAP" is 4-dimethylaminopyridine.
"DMSO" is dimethyl sulfoxide.
"DOPC" is 1,2-dioleoyl-sn-glycero-3-phosphocholine.
"dppf" is 1,1'-bis(diphenylphosphino)ferrocene.
"EDTA" is ethylenediaminetetraacetic acid.
"EtOAc" is ethyl acetate.
"Et" is ethyl.

"Halogen" includes fluorine, chlorine, bromine and iodine.
"HATU" is O-(7-azabenzotriazol-1-yl)-N,N,N',N'-tetramethyluronium hexafluorophosphate, a peptide coupling reagent.
"HPLC" is high pressure liquid chromatography.
"IPA" is isopropyl alcohol.
"i-pr" and "$^i$Pr" represent isopropyl.
"LAH" is lithium aluminum hydride.
"LCMS" is liquid chromatograpy-mass spectrometry.
"LDA" is lithium diisopropyl amide.
"LiHMDS" is lithium hexamethyldisilazide.
"MCPBA" and "m-CPBA" are meta-chloroperbenzoic acid
"Me" represents methyl.
"MPLC" is medium pressure liquid chromatography
"MsCl" is methanesulfonyl chloride
"MS-ESI" is electrospray ionization mass spectrometry.
"MTBE" is methyl t-butyl ether.
"NMP" is N-methyl-2-pyrrolidone.
"O$^i$Pr" is isopropoxy.
"OXONE®" is a commercial persulfate oxidizing agent from DuPont.
"PEG" is poly(ethylene glycol).
"RBF" is a round bottom flask.
"Rochelle's salt" is potassium sodium tartrate.
"RT" and "rt" are abbreviations for room temperature.
"SFC" is supercritical fluid chromatography.
"SM" is starting material.
"TEA" is triethylamine.
"TFA" is trifluoroacetic acid.
"THF" is tetrahydrofuran.
"TLC" is thin layer chromatography.
"TMS" is trimethylsilyl.
"UPLC" is ultra performance liquid chromatography The term "composition," as in pharmaceutical composition, is intended to encompass a product comprising the active ingredient(s) and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of Formula I and a pharmaceutically acceptable carrier.

The substituent "tetrazole" means a 2H-tetrazol-5-yl substituent group and tautomers thereof.

Optical Isomers—Diastereomers—Geometric Isomers—Tautomers

The compounds disclosed herein generally have at least one asymmetric center, and can thus occur as pure stereoisomers and as mixtures of stereoisomers, including racemates, racemic mixtures, single enantiomers, mixtures of enantiomers, diastereomeric mixtures and individual diastereomers in all ratios. The invention includes all possible enantiomers and diastereomers and mixtures of two or more stereoisomers, for example mixtures of enantiomers and/or diastereomers, in all ratios. Thus, enantiomers are a subject of the invention in enantiomerically pure form, both as levorotatory and as dextrorotatory antipodes, in the form of racemates and in the form of mixtures of the two enantiomers in all ratios. In the case of a cis/trans isomerism the invention includes both the cis form and the trans form as well as mixtures of these forms in all ratios. The preparation of individual stereoisomers can be carried out, if desired, by separation of a mixture by customary methods, for example by chromatography or crystallization, by the use of stereochemically uniform starting materials for the synthesis or by stereoselective synthesis. Optionally a derivatization can be carried out before a separation of stereoisomers. The separation of a mixture of stereoisomers can be carried out at an intermediate step during the synthesis of a compound of Formula I or it can be done on a final racemic product. Absolute stereochemistry may be determined by X-ray crystallography of crystalline products or crystalline intermediates which are derivatized, if necessary, with a reagent containing a stereogenic center of known configuration. Where compounds of this invention are capable of tautomerization, all individual tautomers as well as mixtures thereof are included in the scope of this invention. The present invention includes all such isomers, as well as salts, solvates (which includes hydrates) and solvated salts of such racemates, enantiomers, diastereomers and tautomers and mixtures thereof.

Different stereoisomers having the same 2-dimensional chemical structure may have different levels of activity with respect to CETP inhibition, so that some stereoisomers may have higher activity than others. The compounds that are potent inhibitors of CETP may have utility in patients for raising HDL-C, lowering LDL-C, treating dyslipidemia, and for preventing, treating or delaying the onset of conditions that are related to atherosclerosis. Stereoisomers that have little or no activity may have utility as research tools for better understanding CETP inhibition. All stereoisomers and mixtures of stereoisomers of the claimed compounds thus have utility. The compounds of Formula I may also occur as atropisomers (rotamers) due to hindered rotation, which may be observable by NMR spectroscopy, and in some cases may be stable enough with respect to conversion by bond rotation to other atropisomers that they can be isolated and assayed.

Salts

When the compounds of Formula I contain one or more acidic or basic groups the invention also includes the corresponding pharmaceutically acceptable salts. Thus, the compounds of Formula I which contain acidic groups can be used according to the invention, for example, as alkali metal salts, alkaline earth metal salts or as ammonium salts. Examples of such salts include but are not limited to sodium salts, potassium salts, calcium salts, magnesium salts or salts with ammonia or organic amines such as, for example, ethylamine, ethanolamine, triethanolamine or amino acids. Compounds of Formula I which contain one or more basic groups, i.e. groups which can be protonated, can be used according to the invention in the form of their acid addition salts with inorganic or organic acids as, for example but not limited to, salts with hydrogen chloride, hydrogen bromide, phosphoric acid, sulfuric acid, nitric acid, benzenesulfonic acid, methanesulfonic acid, p-toluenesulfonic acid, naphthalenedisulfonic acids, oxalic acid, acetic acid, trifluoroacetic acid, tartaric acid, lactic acid, salicylic acid, benzoic acid, formic acid, propionic acid, pivalic acid, diethylacetic acid, malonic acid, succinic acid, pimelic acid, fumaric acid, maleic acid, malic acid, sulfaminic acid, phenylpropionic acid, gluconic acid, ascorbic acid, isonicotinic acid, citric acid, adipic acid, etc. If the compounds of Formula I simultaneously contain acidic and basic groups in the molecule the invention also includes, in addition to the salt forms mentioned, inner salts or betaines (zwitterions). Salts can be obtained from the compounds of Formula I by customary methods which are known to the person skilled in the art, for example by combination with an organic or inorganic acid or base in a solvent or dispersant, or by anion exchange or cation exchange from other salts. The present invention also includes all salts of the compounds of Formula I which, owing to low physiological compatibility, are not directly suitable for use in pharmaceuticals but which can be used, for example, as intermediates for chemical reactions or for the preparation of pharmaceutically acceptable salts.

Furthermore, compounds of the present invention may exist in one or more amorphous forms and/or one or more crystalline forms, and as such all amorphous and crystalline forms and mixtures thereof of the compounds of Formula I are intended to be included within the scope of the present invention. In addition, some of the compounds of the instant invention may form solvates with water (i.e., a hydrate) or common organic solvents. Such solvates and hydrates, particularly the pharmaceutically acceptable solvates and hydrates, of the instant compounds are likewise encompassed within the scope of this invention, along with unsolvated and anhydrous forms.

It will be understood that, as used herein, references to the compounds of Formula I and Ia and to the examples are meant to also include the pharmaceutically acceptable salts and prodrugs, where such salts and prodrugs are possible.

Prodrugs

Prodrugs, which are compounds that are converted to the compound of Formula I as they are being administered to a patient or after they have been administered to a patient, are also compounds of formula I in the sense that they provide the claimed pharmaceutically active drug moiety to the patient.

Isotopes

In the compounds of Formula I, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic Formula I and Formula II. For example, different isotopic forms of hydrogen (H) include protium ($^1$H) and deuterium ($^2$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within generic Formula I can be prepared without undue experimentation by conventional techniques well known to those skilled in the art or by processes analogous to those described in the Schemes and Examples herein using appropriate isotopically-enriched reagents and/or intermediates.

Utilities

The compounds disclosed herein, including pharmaceutically acceptable salts thereof, are potent inhibitors of CETP. The compounds may therefore be useful in treating mammalian patients, preferably human patients, having diseases and conditions that are treated by inhibition of CETP.

One aspect of the present invention provides a method for treating or reducing the risk of developing a disease or condition that may be treated or prevented by inhibition of CETP by administering a therapeutically effective amount of the compound of Formula I to a patient in need of treatment. The patient is a human or mammal, but is most often a human. A "therapeutically effective amount" is the amount of compound that is effective in obtaining a desired clinical outcome in the treatment of a specific disease.

In one aspect, the invention is a method of treating atherosclerosis in a patient in need of treatment comprising the administration of a therapeutically effective amount of the compound of Formula I or Ia to said patient, or a pharmaceutically acceptable salt thereof.

In one aspect, the invention is a method of raising HDL-C in a patient in need of treatment comprising the administration of a therapeutically effective amount of the compound of Formula I or Ia to said patient, or a pharmaceutically acceptable salt thereof.

In one aspect, the invention is a method of lowering LDL-C in a patient in need of treatment comprising the administration of a therapeutically effective amount of the compound of Formula I or Ia to said patient, or a pharmaceutically acceptable salt thereof.

In one aspect, the invention is a method of treating dyslipidemia in a patient in need of treatment comprising the administration of a therapeutically effective amount of the compound of Formula I or Ia to said patient, or a pharmaceutically acceptable salt thereof.

In one aspect, the invention is the use of the compound of Formula I or Ia or a pharmaceutically acceptable salt thereof for the manufacture of a medicament for the treatment of atherosclerosis.

In one aspect, the invention is the compound of Formula I or Ia or a pharmaceutically acceptable salt thereof for use in the treatment of atherosclerosis.

Diseases or conditions that may be treated with the compounds of Formula I, or which the patient may have a reduced risk of developing as a result of being treated with the compounds of Formula I, include: atherosclerosis, peripheral vascular disease, dyslipidemia, hyperbetalipoproteinemia, hypoalphalipoproteinemia, hypercholesterolemia, hypertriglyceridemia, familial-hypercholesterolemia, cardiovascular disorders, angina, ischemia, cardiac ischemia, stroke, myocardial infarction, reperfusion injury, angioplastic restenosis, hypertension, vascular complications of diabetes, obesity, endotoxemia, and metabolic syndrome. There are reports in the scientific literature that suggest that inhibition of CETP may have utility in preventing or slowing the development of Alzheimer's disease. The compounds of Formula I may therefore have utility in preventing or delaying the progression of Alzheimer's disease or other neurodegenerative diseases.

The compounds disclosed herein are particularly effective in raising HDL-C and/or increasing the ratio of HDL-C to LDL-C. The compounds may also be effective in reducing LDL-C, and may be effective in treating dyslipidemia. These changes in HDL-C and LDL-C may be beneficial in treating atherosclerosis, reducing or delaying the development of atherosclerosis, reducing the risk of developing atherosclerosis, or preventing atherosclerosis. The compounds disclosed herein may thus be beneficial in treating atherosclerosis, reducing or delaying the development of atherosclerosis, reducing the risk of developing atherosclerosis, or preventing atherosclerosis.

Likely indications for atherosclerosis and dyslipidemia using the compounds described herein are written below, where the drug product is titled "CETP inhibitor:"

Atherosclerosis.

In patients at high risk of cardiovascular events because of existing coronary, cerebrovascular, or peripheral vascular disease, CETP inhibitor co-administered with an HMG-CoA reductase inhibitor is indicated to reduce the risk of coronary mortality, myocardial infarction, coronary revascularization procedures, ischemic stroke, and cardiovascular death.

Dyslipidemia.

CETP inhibitor co-administered with a statin is indicated to reduce elevated LDL-C, apolipoprotein B (ApoB), lipoprotein a (Lp(a)), non-HDL-C, and total cholesterol; and increase HDL-C and apolipoprotein A-1 (Apo A-1) in patients with mixed or primary dyslipidemia.

Administration and Dose Ranges

Any suitable route of administration may be employed for providing a mammal, especially a human, with an effective dose of the compounds described herein. For example, oral, rectal, topical, parenteral, ocular, pulmonary, nasal, and the like may be employed. Dosage forms include tablets, troches, dispersions, suspensions, solutions, capsules, creams, ointments, aerosols, and the like. Preferably the compound of Formula I is administered orally.

When treating the diseases for which the compound of Formula I is indicated, generally satisfactory results are expected when the compound of Formula I is administered at a daily dosage of from about 0.1 milligram to about 1000 milligram in one dose daily or divided into more than one dose per day.

Oral administration will usually be carried out using tablets. Examples of doses in tablets include 0.1 mg, 0.5 mg, 1 mg, 2 mg, 5 mg, 10 mg, 25 mg, 50 mg, 60 mg, 70 mg, 80 mg, 90 mg, 100 mg, 110 mg, 120 mg, 130 mg, 140 mg, 150 mg, 160 mg, 170 mg, 180 mg, 190 mg, 200 mg, 210 mg, 220 mg, 230 mg, 240 mg, 250 mg, 275 mg, 300 mg, 350 mg, 400 mg, 450 mg, 500 mg, and 1000 mg. Other oral forms can also have the same dosages (e.g. capsules). A preferred dose is likely in the range of 50-200 mg.

Pharmaceutical Compositions

Another aspect of the present invention provides pharmaceutical compositions which comprise the compound of Formula I and a pharmaceutically acceptable carrier. The pharmaceutical compositions of the present invention comprise the compound of Formula I or a pharmaceutically acceptable salt as an active ingredient, as well as a pharmaceutically acceptable carrier and optionally other therapeutic ingredients. The term "pharmaceutically acceptable salts" refers to salts prepared from pharmaceutically acceptable non-toxic bases or acids including inorganic bases or acids and organic bases or acids. A pharmaceutical composition may also comprise a prodrug, or a pharmaceutically acceptable salt thereof, if a prodrug is administered. A pharmaceutical composition may also consist essentially of the compound of Formula I, or a pharmaceutically acceptable salt of the compound, and a pharmaceutically acceptable carrier, without other therapeutic ingredients.

Pharmaceutical compositions may be formulated to be suitable for oral, rectal, topical, parenteral (including subcutaneous, intramuscular, and intravenous), ocular (ophthalmic), pulmonary (nasal or buccal inhalation), or nasal administration, although the most suitable route in any given case will depend on the nature and severity of the conditions being treated and on the nature of the active ingredient. They may be conveniently presented in unit dosage form and prepared by any of the methods well-known in the art of pharmacy.

In practical use, the compound of Formula I can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, hard and soft capsules and tablets, with the solid oral preparations being preferred over the liquid preparations.

Because of their ease of administration, tablets and capsules represent the most advantageous oral dosage unit form in which case solid pharmaceutical carriers are obviously employed. If desired, tablets may be coated by standard aqueous or nonaqueous techniques. Such compositions and preparations should contain at least 0.1 percent of active compound. The percentage of active compound in these compositions may, of course, be varied and may conveniently be between about 2 percent to about 60 percent of the weight of the unit. The amount of active compound in such therapeutically useful compositions is such that an effective dosage will be obtained. The active compound can also be administered intranasally as, for example, liquid drops or spray.

The tablets, pills, capsules, and the like may also contain a binder such as gum tragacanth, acacia, corn starch or gelatin; excipients such as dicalcium phosphate; a disintegrating agent such as corn starch, potato starch, alginic acid; a lubricant such as magnesium stearate; and a sweetening agent such as sucrose, lactose or saccharin. When a dosage unit form is a capsule, it may contain, in addition to materials of the above type, a liquid carrier such as a fatty oil.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor.

The compound of formula I may also be administered parenterally. Solutions or suspensions of the compound can be prepared in water suitably mixed with a surfactant such as hydroxypropylcellulose. Dispersions can also be prepared in glycerol, liquid polyethylene glycols and mixtures thereof in oils. Under ordinary conditions of storage and use, these preparations may contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g. glycerol, propylene glycol and liquid polyethylene glycol), suitable mixtures thereof, and vegetable oils.

Combination Therapy

The compound of Formula I, including pharmaceutically acceptable salts thereof, may be used in pharmaceutical combinations with other drugs that may also be useful in the treatment or amelioration of the diseases or conditions for which the compound of Formula I is useful. Such other drugs may be administered, by a route and in an amount commonly used therefor, contemporaneously or sequentially with the compound of Formula I. When the compound of Formula I is used contemporaneously with one or more other drugs, a pharmaceutical composition in unit dosage form containing such other drugs and the compound of Formula I is preferred. However, the combination therapy also includes therapies in which the compound of Formula I and one or more other drugs are administered concomitantly, on the same or different schedules. The drugs that are administered, whether alone or in combination with other drugs, include the free-acid, free-base, and pharmaceutically acceptable salt forms, pro-drug forms (including but not limited to esters), and salts of pro-drugs of the medicinal agents where chemically possible When oral formulations are used, the drugs may be combined into a single combination tablet or other oral dosage form, or the drugs may be packaged together as separate tablets or other oral dosage forms. It is also contemplated that when used in combination with one or more other active ingredients, the compound of formula I and the other active ingredients may be used in lower doses than when each is used singly. Accordingly, the pharmaceutical compositions of the compound of formula I include those that contain one or more other active ingredients, in addition to the compound of Formula I.

The compound of Formula I will likely be approved initially for coadministration with a statin, which could be administered in the form of a fixed dose combination of the compound of formula I and a statin. Additional drugs may also be administered in combination with the compound of Formula I and the statin, either by coadministration or in a fixed dose combination. The compound of formula I and the drugs that are administered with it may be administered as pharmaceutically acceptable salts, as prodrugs, or otherwise formulated for immediate release, extended release, or controlled release, as necessary.

Examples of statins that may be administered in combination with the compound of Formula I include, but are not limited to, (i) simvastatin and lovastatin which are marketed as ZOCOR® and MEVACOR® in lactone prodrug form and function as inhibitors after administration, and (ii) dihydroxy open ring acid HMG-CoA reductase inhibitors such as atorvastatin (particularly the calcium salt sold in LIPITOR®), rosuvastatin (particularly the calcium salt sold in CRESTOR®), pravastatin (particularly the sodium salt sold in PRAVACHOL®), fluvastatin (particularly the sodium salt sold in LESCOL®), and pitavastatin (particularly the calcium salt sold in LIVALO®), and (iii) other statins that may yet be developed. Preferred statins for combination therapy include atorvastatin, rosuvastatin, and simvasatin, as described above.

Cholesterol absorption inhibitors, and particularly ezetimibe (ZETIA®), as well as other cholesterol absorption inhibitors, such as stanol esters, beta-sitosterol, sterol glycosides such as tiqueside, and other azetidinones, may be administered with the compound of Formula I or II, generally with a statin, as described above. The preferred cholesterol absorption inhibitor is ezetimibe. Combinations of the compound of formula I with a statin and a cholesterol inhibitor, such as ezetimibe, are also contemplated. Preferred 3-component combinations include combinations of the compound of formula I with simvastatin, atorvastatin, or rosuvastatin in combination with ezetimibe, where the statins may be salt forms or prodrugs as described above. The combination of simvastatin with ezetimibe is currently marketed as VYTORIN®.

Other cholesterol reducing drugs that may be coadministered with the compound of formula I in addition to HMG- CoA reductase inhibitors (statins) and cholesterol absorption inhibitors include (i) bile acid sequestrants, as for example cholestyramine, colestipol, dialkylaminoalkyl derivatives of a cross-linked dextran, Colestid®, and LoCholest®, (ii) niacin and related compounds, such as nicotinyl alcohol, nicotinamide, and nicotinic acid or a salt thereof, in an immediate release or extended release form, which may optionally be in the form of a combination with a DP-1 antagonist, such as laropiprant, (iii) PPARα agonists, such as gemfibrozil and fenofibric acid derivatives (fibrates), including clofibrate, fenofibrate, bezafibrate, ciprofibrate, and etofibrate, (iv) acyl CoA:cholesterol acyltransferase (ACAT) inhibitors, such as avasimibe and melinamide, and including selective ACAT-1 and ACAT-2 inhibitors and dual inhibitors, (v) phenolic anti-oxidants, such as probucol, (vi) microsomal triglyceride transfer protein (MTP)/ApoB secretion inhibitors, (vii) anti-oxidant vitamins, such as vitamins C and E and beta carotene, (viii) thyromimetics, (ix) LDL (low density lipoprotein) receptor inducers, (x) platelet aggregation inhibitors, for example glycoprotein IIb/IIIa fibrinogen receptor antagonists and aspirin, (xi) vitamin B12 (also known as cyanocobalamin), (xii) folic acid or a pharmaceutically acceptable salt or ester thereof, such as the sodium salt and the methylglucamine salt, (xiii) FXR and LXR ligands, including both inhibitors and agonists, (xiv) agents that enhance ABCA1 gene expression, (xv) ileal bile acid transporters, and (xvi) niacin receptor agonists (e.g. acipimox and acifran) and partial agonists.

Finally the compound of formula I can be combined with compounds that are useful for treating other diseases, such as diabetes, hypertension and obesity, as well as other anti-atherosclerotic compounds. Such combinations may be used to treat one or more of such diseases as diabetes, obesity, atherosclerosis, and dyslipidemia, or more than one of the diseases associated with metabolic syndrome. The combinations may exhibit synergistic activity in treating these diseases, allowing for the possibility of administering reduced doses of active ingredients, such as doses that otherwise might be sub-therapeutic.

Examples of other active ingredients that may be administered in combination with a compound of formula I include, but are not limited to, compounds that are primarily anti-diabetic compounds, including:

(a) PPAR gamma agonists and partial agonists, including glitazones and non-glitazones (e.g. pioglitazone, englitazone, MCC-555, rosiglitazone, balaglitazone, netoglitazone, T-131, LY-300512, LY-818, and compounds described in WO 02/060388, WO 02/08188, WO 2004/019869, WO 2004/020409, WO 2004/020408, and WO2004/066963);

(b) biguanides such as metformin, phenformin, and pharmaceutically acceptable salts thereof, in particular metformin hydrochloride and extended release formulations thereof, such as Glumetza™, Fortamet™, and GlucophageXR™;

(c) protein tyrosine phosphatase-1B (PTP-1B) inhibitors, such as ISIS-113715 and TTP814;

(d) dipeptidyl peptidase IV (DP-IV) inhibitors, including sitagliptin, vildagliptin, saxagliptin, alogliptin, linagliptin, dutogliptin, teneligliptin, MK-3102, and gemigliptin;

(e) insulin or insulin mimetics, such as for example insulin lispro, insulin glargine, insulin detemir, insulin glulisine, insulin degludec, SBS1000, insulin zinc suspension, and oral and inhalable formulations of insulin and insulin analogs;

(f) sulfonylureas, such as tolbutamide, glipizide, glimepiride, acetohexamide, chlorpropamide, glibenclamide, and related materials;

(g) α-glucosidase inhibitors (such as acarbose, adiposine; camiglibose; emiglitate; miglitol; voglibose; pradimicin-Q; and salbostatin);

(h) PPARα/γ dual agonists, such as muraglitazar, tesaglitazar, farglitazar, and naveglitazar;

(i) PPARδ agonists such as GW501516 and those disclosed in WO97/28149;

(j) glucagon receptor antagonists;

(k) GLP-1; GLP-1 derivatives; GLP-1 mimetics, GLP-1 analogs, and GLP-1 receptor agonists, such as exendins, e.g. exenatide (BYETTA), dulaglutide, semaglutide, albiglutide, liraglutide, lixisenatide, and taspoglutide, including intranasal, tranxsdermal, and once weekly fomulations thereof, and oxyntomodulin analogs and derivatives, and non-peptidyl GLP-1 receptor agonists;

(l) GIP-1;

(m) amylin and amylin analogs (e.g. pramlintide);

(n) Non-sulfonylurea insulin secretagogues, such as the meglitinides (e.g. glimepiride, mitiglinide, meglitinide, nateglinide, and rapeglinide); and (o) leptin and leptin derivatives and agonists.

In one embodiment, the invention is a pharmaceutical composition comprising the compound of Formula I or Ia, or a pharmaceutically acceptable salt thereof, a pharmaceutically acceptable carrier, and one or more of the following active ingredients:

(i) HMG-CoA reductase inhibitors;
(ii) bile acid sequestrants;
(iii) niacin and related compounds;
(iv) PPARα agonists;
(v) cholesterol absorption inhibitors;
(vi) acyl CoA:cholesterol acyltransferase (ACAT) inhibitors;
(vii) phenolic anti-oxidants;
(viii) microsomal triglyceride transfer protein (MTP)/ApoB secretion inhibitors;
(ix) anti-oxidant vitamins;
(x) thyromimetics;
(xi) LDL (low density lipoprotein) receptor inducers;
(xii) platelet aggregation inhibitors;
(xiii) vitamin B12 (also known as cyanocobalamin);
(xiv) folic acid or a pharmaceutically acceptable salt or ester thereof;
(xv) FXR and LXR ligands;
(xvi) agents that enhance ABCA1 gene expression;
(xvii) ileal bile acid transporters; and
(xviii) niacin receptor agonists.

The compounds of this invention can be advantageously administered in combination with antidiabetic compounds. Preferred combinations with antidiabetic compounds include combinations of the compounds disclosed herein with DP-IV inhibitors (sitagliptin, vildagliptin, saxagliptin, alogliptin, linagliptin, dutogliptin, teneligliptin, omarigliptin, and gemigliptin), combinations with biguanides, and combinations with both a DP-IV inhibitor and a biguanide. The preferred DP-IV inhibitor is sitagliptin, and the preferred biguanide is metformin in the formulations and salt forms described above.

Other active ingredients that may be advantageously used in combination with the compound of formula I include antiobesity compounds, such as 5-HT(serotonin) inhibitors, neuropeptide Y5 (NPY5) inhibitors, melanocortin 4 receptor (Mc4r) agonists, cannabinoid receptor 1 (CB-1) antagonists/inverse agonists, and β3 adrenergic receptor agonists.

Other active ingredients that can be advantageously used in combination with the compounds described herein include active ingredients that are used to treat inflammatory conditions, such as aspirin, non-steroidal anti-inflammatory drugs, glucocorticoids, azulfidine, and selective cyclooxygenase-2 (COX-2) inhibitors, including etoricoxib, celecoxib, rofecoxib, and Bextra.

Antihypertensive compounds may also be used advantageously in combination therapy with the compound of formula I. Examples of antihypertensive compounds that may be used with the compound of formula I include thiazide-like diuretics, e.g., hydrochlorothiazide (HCTZ or HCT); angiotensin converting enzyme inhibitors (e.g., alacepril, benazepril, captopril, ceronapril, cilazapril, delapril, enalapril, enalaprilat, fosinopril, imidapril, lisinopril, moveltipril, perindopril, quinapril, ramipril, spirapril, temocapril, or trandolapril); dual inhibitors of angiotensin converting enzyme (ACE) and neutral endopeptidase (NEP) such as omapatrilat, sampatrilat and fasidotril; angiotensin II receptor antagonists, also known as angiotensin receptor blockers or ARBs, which may be in free-base, free-acid, salt or pro-drug form, such as azilsartan, e.g., azilsartan medoxomil potassium (EDARBI®), candesartan, e.g., candesartan cilexetil (ATACAND®), eprosartan, e.g., eprosartan mesylate (TEVETAN®), irbesartan (AVAPRO®), losartan, e.g., losartan potassium (COZAAR®), olmesartan, e.g, olmesartan medoximil (BENICAR®), telmisartan (MICARDIS®), valsartan (DIOVAN®), and any of these drugs used in combination with a thiazide-like diuretic such as hydrochlorothiazide (e.g., HYZAAR®, DIOVAN HCT®, ATACAND HCT®, etc.); potassium sparing diuretics such as amiloride HCl, spironolactone, epleranone, triamterene, each with or without HCTZ; carbonic anhydrase inhibitors, such as acetazolamide; neutral endopeptidase inhibitors (e.g., thiorphan and phosphoramidon); aldosterone antagonists; aldosterone synthase inhibitors; small molecule renin inhibitors, such as enalkrein; RO 42-5892; A 65317; CP 80794; ES 1005; ES 8891; SQ 34017; aliskiren (2(S),4(S),5(S),7(S)—N-(2-carbamoyl-2-methylpropyl)-5-amino-4-hydroxy-2,7-diisopropyl-8-[4-methoxy-3-(3-methoxypropoxy)-phenyl]-octanamid hemifumarate) SPP600, SPP630 and SPP635); endothelin receptor antagonists; vasodilators (e.g. nitroprusside); calcium channel blockers (e.g., amlodipine, nifedipine, verapamil, diltiazem, felodipine, gallopamil, niludipine, nimodipine, nicardipine, bepridil, nisoldipine); potassium channel activators (e.g., nicorandil, pinacidil, cromakalim, minoxidil, aprilkalim, loprazolam); sympatholitics; beta-adrenergic blocking drugs (e.g., acebutolol, atenolol, betaxolol, bisoprolol, carvedilol, metoprolol, metoprolol tartate, nadolol, propranolol, sotalol, timolol); alpha adrenergic blocking drugs (e.g., doxazocin, prazocin or alpha methyldopa); central alpha adrenergic agonists; peripheral vasodilators (e.g. hydralazine); and nitrates or nitric oxide donating compounds, e.g. isosorbide mononitrate.

Preferred antihypertensives that may be used in combination with the CETP inhibitors disclosed herein include one or more of an angiotensin II antagonist (losartan), an ACE inhibitor (enalapril or captopril), and hydrochlorothiazide.

Anti-obesity compounds may be administered in combination with the compounds of Formula I, including: (1) growth hormone secretagogues and growth hormone secretagogue receptor agonists/antagonists, such as NN703 and hexarelin; (2) protein tyrosine phosphatase-1B (PTP-1B) inhibitors; (3) cannabinoid receptor ligands, such as cannabinoid $CB_1$ receptor antagonists or inverse agonists; (4) anti-obesity serotonergic agents, such as fenfluramine, dexfenfluramine, phentermine, and sibutramine; (5) β3-adrenoreceptor agonists, such as AD9677/TAK677 (Dainippon/Takeda), CL-316,243, SB 418790, BRL-37344, L-796568, BMS-196085, BRL-35135A, CGP12177A, BTA-243, Trecadrine, Zeneca D7114, and SR 59119A; (6) pancreatic lipase inhibitors, such as orlistat (Xenical®), Triton WR1339, RHC80267, lipstatin, tetrahydrolipstatin, teasaponin, and diethylumbelliferyl phosphate; (7) neuropeptide Y1 antagonists, such as BIBP3226, J-115814, BIBO 3304, LY-357897, CP-671906, and GI-264879A; (8) neuropeptide Y5 antagonists, such as GW-569180A, GW-594884A, GW-587081X, GW-548118X, FR226928, FR 240662, FR252384, 1229U91, GI-264879A, CGP71683A, LY-377897, PD-160170, SR-120562A, SR-120819A and JCF-104; (9) melanin-concentrating hormone (MCH) receptor antagonists; (10) melanin-concentrating hormone 1 receptor (MCH1R) antagonists, such as T-226296 (Takeda); (11) melanin-concentrating hormone 2 receptor (MCH2R) agonist/antagonists; (12) orexin-1 receptor antagonists, such as SB-334867-A; (13) melanocortin agonists, such as Melanotan II; (14) other Mc4r (melanocortin 4 receptor) agonists, such as CHIR86036 (Chiron), ME-10142, and ME-10145 (Melacure), CHIR86036 (Chiron); PT-141, and PT-14 (Palatin); (15) 5HT-2 agonists; (16) 5HT2C (serotonin receptor 2C) agonists, such as BVT933, DPCA37215, WAY161503, and R-1065; (17) galanin antagonists; (18) CCK agonists; (19) CCK-A (cholecystokinin-A) agonists, such as AR-R 15849, GI 181771, JMV-180, A-71378, A-71623 and SR146131; (20) GLP-1 agonists; (21) corticotropin-releasing hormone agonists; (22) histamine receptor-3 (H3) modulators; (23) histamine receptor-3 (H3) antagonists/inverse agonists, such as hioperamide, 3-(1H-imidazol-4-yl)propyl N-(4-pentenyl)carbamate, clobenpropit, iodophenpropit, imoproxifan, and GT2394 (Gliatech); (24)β-hydroxy steroid dehydrogenase-1 inhibitors (11β-HSD-1 inhibitors), such as BVT 3498 and, BVT 2733, (25) PDE (phosphodiesterase) inhibitors, such as theophylline, pentoxifylline, zaprinast, sildenafil, amrinone, milrinone, cilostamide, rolipram, and cilomilast; (26) phosphodiesterase-3B (PDE3B) inhibitors; (27) NE (norepinephrine) transport inhibitors, such as GW 320659, despiramine, talsupram, and nomifensine; (28) ghrelin receptor antagonists; (29) leptin, including recombinant human leptin (PEG-OB, Hoffman La Roche) and recombinant methionyl human leptin (Amgen); (30) leptin derivatives; (31) BRS3 (bombesin receptor subtype 3) agonists such as [D-Phe6, beta-Ala11,Phe13,Nle14]Bn(6-14) and [D-Phe6,Phe13]Bn (6-13)propylamide; (32) CNTF (Ciliary neurotrophic factors), such as GI-181771 (Glaxo-SmithKline), SR146131 (Sanofi Synthelabo), butabindide, PD170,292, and PD 149164 (Pfizer); (33) CNTF derivatives, such as axokine (Regeneron); (34) monoamine reuptake inhibitors, such as sibutramine; (35) UCP-1 (uncoupling protein-1, 2, or 3) activators, such as phytanic acid, 4-[(E)-2-(5,6,7,8-tetrahydro-5,5,8,8-tetramethyl-2-napthalenyl)-1-propenyl]benzoic acid (TTNPB), and retinoic acid; (36) thyroid hormone β-agonists, such as KB-2611 (KaroBioBMS); (37) FAS (fatty acid synthase) inhibitors, such as Cerulenin and C75; (38) DGAT1 (diacylglycerol acyltransferase 1) inhibitors; (39) DGAT2 (diacylglycerol acyltransferase 2) inhibitors; (40) ACC2 (acetyl-CoA carboxylase-2) inhibitors; (41) glucocorticoid antagonists; (42) acyl-estrogens, such as oleoylestrone; (43) dicarboxylate transporter inhibitors; (44) peptide YY, PYY 3-36, peptide YY analogs, derivatives, and fragments such as BIM-43073D, BIM-43004C, (45) Neuropeptide Y2 (NPY2) receptor agonists such NPY3-36, N acetyl [Leu(28,31)] NPY 24-36, TASP-V, and cyclo-(28/32)-Ac-[Lys28-Glu32]-(25-36)-pNPY; (46) Neuropeptide Y4 (NPY4) agonists such as pancreatic peptide (PP); (47) Neuropeptide Y1 (NPY1) antagonists such as BIBP3226, J-115814, BIBO 3304, LY-357897, CP-671906, and GI-264879A; (48) Opioid antagonists, such as nalmefene (Revex®), 3-methoxynaltrexone, naloxone, and naltrexone; (49) glucose transporter inhibitors; (50) phosphate transporter inhibitors; (51) 5-HT (serotonin) inhibitors; (52) beta-blockers; (53) Neurokinin-1 receptor antagonists (NK-1 antagonists); (54) clobenzorex; (55) cloforex; (56) clominorex; (57) clortermine; (58) cyclexedrine; (59) dextroamphetamine; (60) diphemethoxidine, (61) N-ethylamphetamine; (62) fenbutrazate; (63) fenisorex; (64) fenproporex; (65) fludorex; (66) fluminorex; (67) furfurylmethylamphetamine; (68) levamfetamine; (69) levophacetoperane; (70) mefenorex; (71) metamfepramone; (72) methamphetamine; (73) norpseudoephedrine; (74) pentorex; (75) phendimetrazine; (76) phenmetrazine; (77) picilorex; (78) phytopharm 57; (79) zonisamide, (80) aminorex; (81) amphechloral; (82) amphetamine; (83) benzphetamine; and (84) chlorphentermine.

The combination therapies described above which use the compounds of Formula I may also be useful in the treatment of the metabolic syndrome. According to one widely used definition, a patient having metabolic syndrome is characterized as having three or more symptoms selected from the following group of five symptoms: (1) abdominal obesity; (2) hypertriglyceridemia; (3) low high-density lipoprotein cholesterol (HDL); (4) high blood pressure; and (5) elevated fasting glucose, which may be in the range characteristic of Type 2 diabetes if the patient is also diabetic. Each of these symptoms is defined clinically in the Third Report of the National Cholesterol Education Program Expert Panel on Detection, Evaluation and Treatment of High Blood Cholesterol in Adults (Adult Treatment Panel III, or ATP III), National Institutes of Health, 2001, NIH Publication No. 01-3670. Patients with metabolic syndrome have an increased risk of developing the macrovascular and microvascular complications that are listed above, including atherosclerosis and coronary heart disease. The combinations described above may ameliorate more than one symptom of metabolic syndrome concurrently (e.g. two symptoms, three symptoms, four symptoms, or all five of the symptoms).

Assays

Protocol: Scintillation Proximity Assay (SPA) for CETP Activity

First, low density lipoprotein (LDL) (Meridian) is biotinylated by incubating LDL with biotin for 1 hour on ice, after which it is dialyzed to remove free biotin. Then compounds at varying concentrations are incubated with 15 nM CETP (reagent production group. In Vitro Pharmacology, MRL Rahway) and 50 ug/ml of the biotinylated LDL in 50 mM HEPES, 150 mM NaCl, pH 7.4, for 1 hour at 37° C. The reaction is started by adding $^3$H-cholesterol ester high density lipoprotein (HDL) (American Radiochemicals Corp) at a concentration of ~0.6 nM. The reaction proceeds for 2 hours at 37° C., after which time it is quenched by the addition of 12% acetic acid. PVT streptavadin-coated scintillation proximity beads, which have been brought to room temperature, are then added at a concentration of 4 mg/ml. The assay is then mixed and counted after one half hour in a Microbeta plate reader.

In Vitro Radioactive Assays of CETP-Catalyzed CE and TG Transfer (RTA Assay)

Reagents and sources are: [3H] cholesteryl oleate (GE #TRK.886), [3H] Triolein (Perkin-Elmer NET-431), Butylated hydroxyl toluene (Aldrich, #D4740-4), DOPC (Sigma, # P6354), Sodium Bromide (Fisher scientific #S255-500), PEG 8000 (Fisher, #BP233-1), and human HDL (Intracel Corp #RP-036).

An in vitro assay for determining $IC_{50}$'s to identify compounds that inhibit CETP transfer activity is performed based on a modification of a published method (Morton and Zilversmit, (1981) A plasma inhibitor of triglyceride and cholesteryl ester transfer activities, J. Biol. Chem. 256(23), 11992-11995). The ability of inhibitors to alter CETP activity is performed using two different assays: one using recombinant CETP and one using an endogenous plasma source of CETP. Both assays measure the transfer of [3H] cholesteryl oleate or [3H] triolein from exogenous LDL to HDL.

Radiolabeled donor particles are generated by first combining 100 µl of 200 µM butylated hydroxyl toluene in $CHCl_3$, 216 µL of 21.57 mM DOPC in EtOH, and either 500 µCi [3H]-triolein (Perkin Elmer #NET-431) or 500 µCi [3H]-cholesteryl oleate (GE #TRK886) in a glass tube. Reagents are mixed, dried under nitrogen, and then resuspended in 2 mL of 50 mM Tris, 27 µM EDTA at pH 7.4. After a brief vortex, the solution is sonicated until clear and mixed with 20 mL of fresh human serum. The mixture is incubated overnight at 37° C. The [3H] labeled LDL substrate is separated at 1.063 g/ml density by sequential ultracentrifugal flotation in NaBr according to the method of Havel, Eder, et al., 1955, and Chapman, Goldstein, et al., 1981. Once isolated the particles are dialyzed 3× in CETP buffer (50 mM Tris, pH 7.4, 100 mM NaCl, 1 mM EDTA). Human HDL is purchased from Intracel and used as the acceptor particles.

Transfer assays are performed in a 96-well v-bottom polypropylene plate. For the RTA using recombinant CETP (2% RTA), an assay cocktail is prepared with the final concentrations 128 µg/mL HDL, 20 nM rCETP, 2% human serum, and 1×CETP buffer. 1 µL of each test compound diluted in DMSO is added to 47 µL of assay cocktail per well and incubated at 37° C. for 1 hour. To initiate the transfer reaction, 2 µL radiolabeled LDL is added. After an additional 60 min of incubation at 37° C., the transfer action is terminated by precipitation of LDL with an equal volume of 20% WN PEG 8000. The plates are centrifuged at 2000 rpm for 30 minutes at 4° C. A 40 µL aliquot of the HDL-containing supernatant is transferred to a Packard Optiplate™ with 200 µL of MicroScint™ 20. After mixing, plates are counted by liquid scintillation. Counts present in the supernatant for blanks (wells containing only HDL acceptor, CETP buffer and DMSO) are subtracted from those containing test compounds and used to correct for non-specific transfer.

For the transfer assay using endogenous CETP from serum (95% RTA), the same procedure is used except that human serum is added such that a final concentration of serum of 95% of the total assay volume is achieved, yielding a concentration of approximately 15 nM endogenous CETP in the assay. This is then combined with HDL and CETP buffer and the reaction proceeds as above and is terminated as described.

Comparison of the counts of samples with inhibitors to an uninhibited (DMSO only) positive control yield a percent inhibition. A plot of percent inhibition vs. log of inhibitor concentration, fit to a Sigmoidal 4 parameter equation is used to calculate IC50.

EXAMPLES

The following schemes and examples are provided so that the invention will be more fully appreciated and understood.

These schemes and examples are illustrative and are not to be construed as limiting the invention in any way. The claims appended hereto define the scope of the invention. The examples are specific compounds of the invention that were made and are CETP inhibitors based on the assay data for the compounds.

Starting materials are commercially available or are made using known procedures or as shown below. The examples may be synthesized according to the general schemes provided below and by using the synthetic intermediates that are described. The data reported for the examples below were generally obtained using the RTA assay in 95% human serum. The IC50's for the examples using this assay are in the range of about 270-5040 nM. Preferred compounds have an IC50 less than about 1000 nM. More preferred compounds have an IC50 less than about 500 nM. When compounds of Formula I are mentioned herein, such compounds include compounds defined generically by Formula I and also the specific examples disclosed herein. The specific compounds that are disclosed as examples are CETP inhibitors. They were made as disclosed, and they inhibit CETP as shown by the assay data that were obtained for the individual compounds.

Synthetic Schemes

Scheme A

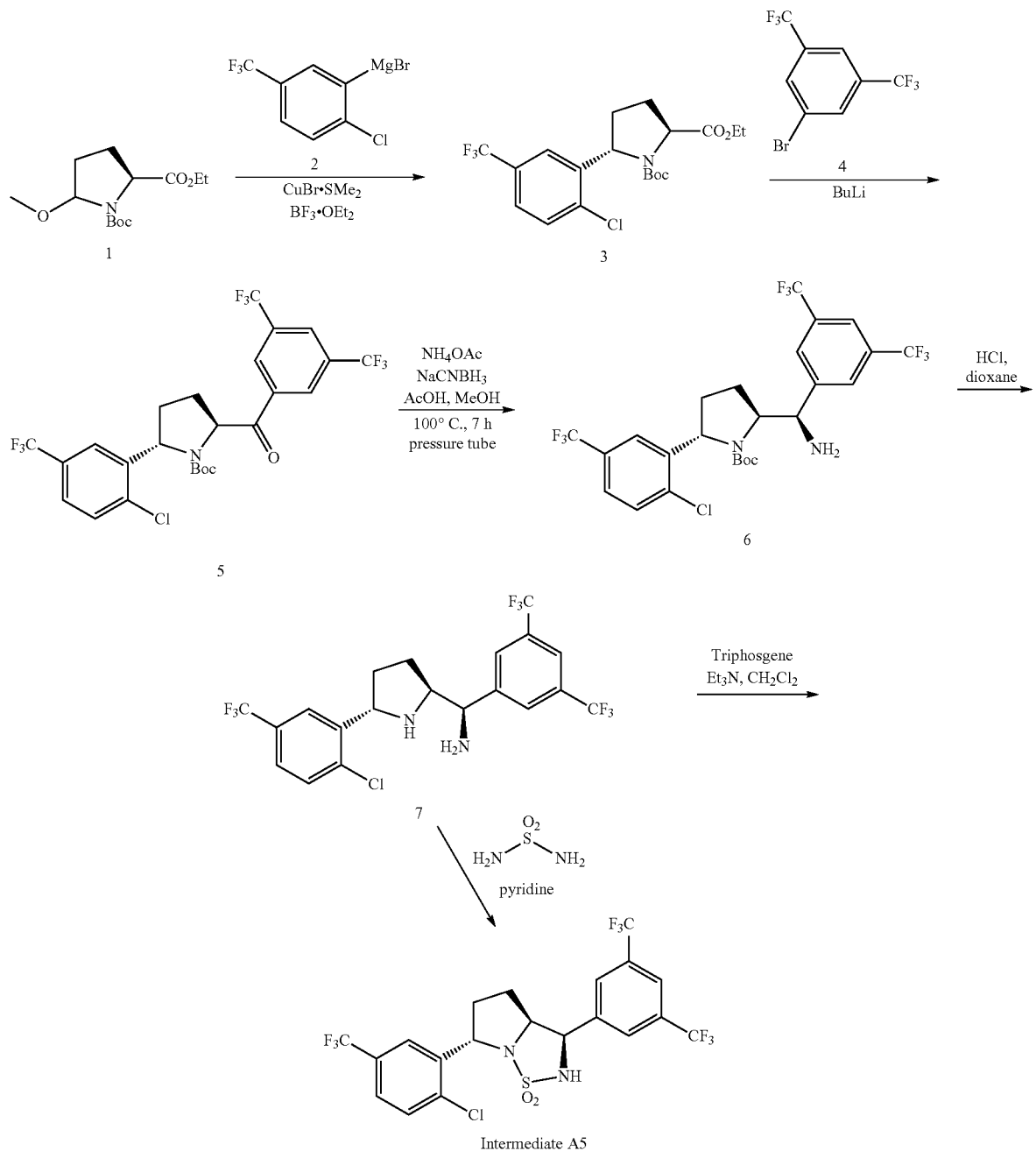

Intermediate A5

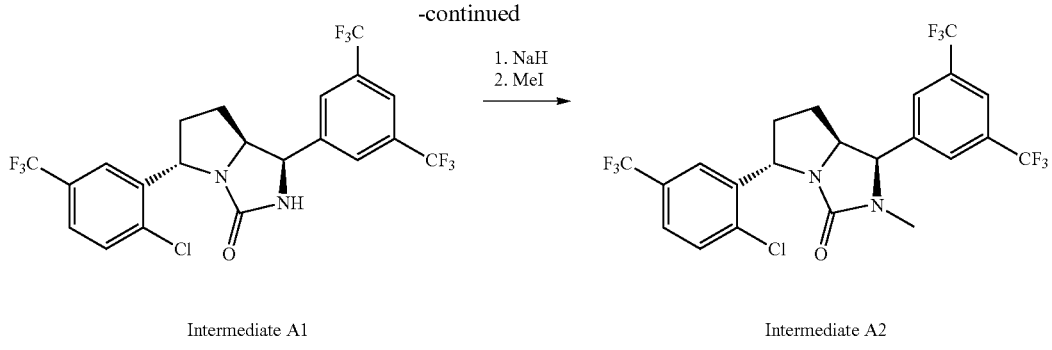

Intermediate A1 → Intermediate A2

1. NaH
2. MeI (2S,5S)-1-tert-butyl 2-ethyl 5-(2-chloro-5-(trifluoromethyl)phenyl)pyrrolidine-1,2-dicarboxylate 3 was synthesized according to a published procedure (Wallen et al., Tetra. Lett., 2003, 44, 2081-2082). It was treated with (3,5-bis(trifluoromethyl)phenyl)lithium generated in situ to give the desired ketone intermediate. Reductive amination, followed by removal of the Boc group and cyclization gave Intermediate A1. Intermediate A1 was alkylated to give Intermediate A2. Alternatively, diamine 7 was treated with sulfuric diamide in pyridine to give A5.

Intermediate A1

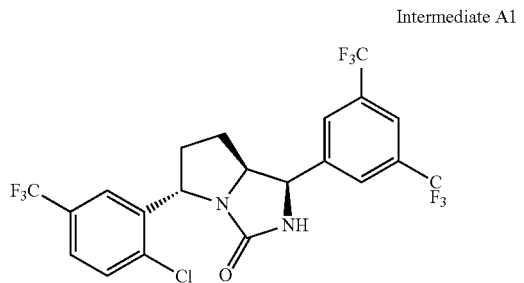 [SMILES: O=C1N[C@H](c2cc(C(F)(F)F)cc(C(F)(F)F)c2)[C@@H]2CC[C@@H](c3cc(C(F)(F)F)ccc3Cl)N12]

((1R,5S,7aS)-1-(3,5-bis(trifluoromethyl)phenyl)-5-(2-chloro-5-(trifluoromethyl)phenyl)tetrahydro-1H-pyrrolo[1,2-c]imidazol-3(2H)-one Step 1:

To a 500 mL three-neck RBF equipped with a magnetic stirring bar were added, under $N_2$ atmosphere, 3-bromo-4-chloro-benzotrifluoride (16.5 mL, 110 mmol) and dry THF (150 mL). The resulting solution was cooled to 0° C. To this solution was added i-PrMgBr (110 mL, 110 mmol) and the reaction was warmed to rt and stirred for 1 h. To another 500 mL RBF containing a solution of $CuBr.Me_2S$ (18.8 g, 91.5 mmol) in THF (100 mL) was added $BF_3.OEt2$ (14 mL, 110 mmol) dropwise at −40° C. The resulting solution was stirred at that temperature for 45 min. Then, the Grignard reagent prepared previously was added dropwise to this solution while maintaining the internal temperature at −32 to −38° C. After completion of addition, the reaction mixture was stirred at that temperature for 1 h. The reaction mixture was cooled to −78° C., and a solution of (2S)-1-t-butyl 2-ethyl 5-methoxypyrrolidine-1,2-dicarboxylate (25.0 g, 91.5 mmol) in THF (50 mL) was added dropwise. The resulting reaction mixture was allowed to warm up to rt and was stirred for 14 h. The reaction mixture was cooled to 0° C., and saturated aqueous $NH_4Cl$ solution (100 mL) was added followed by aqueous $NH_4OH$ solution (100 mL) and water (300 mL). The layers were separated. The aqueous layer was extracted with EtOAc (3×200 mL). The combined organics were dried over anhydrous $Na_2SO_4$ and concentrated. The crude product was purified by column chromatography eluting with 5% EtOAc in petroleum ether to yield (2S,5S)-1-tert-butyl 2-ethyl 5-(2-chloro-5-(trifluoromethyl)phenyl)pyrrolidine-1,2-dicarboxylate (34.0 g, 79.8 mmol) as a colorless liquid. $^1$H NMR (400 MHz, $CDCl_3$) δ 7.32-7.47 (m, 3H), 5.39-5.50 (m, 1H), 4.58-4.70 (m, 1H), 4.22-4.28 (m, 2H), 2.55 (m, 1H), 2.18 (m, 1H), 2.05 (m, 1H), 1.83 (m, 1H), 1.16-1.43 (m, 12H); LC-MS ESI calc'd. for $C_{19}H_{23}ClF_3NO_4$ [M-Boc]+321.84. found 322.2.

Step 2:

To a 250 mL RBF containing a solution of (2S,5S)-1-tert-butyl 2-ethyl 5-(2-chloro-5-(trifluoromethyl)phenyl)pyrrolidine-1,2-dicarboxylate (4.00 g, 9.48 mmol) and 1-bromo-3,5-bis(trifluoromethyl)benzene (2.5 mL, 14.22 mmol) in diethyl ether (40 mL) was added n-BuLi (1.6 M in hexanes, 8.9 mL, 14.2 mmol) dropwise at −78° C. The resulting solution was stirred at that temperature for 2 h, and was allowed to warm to rt and stirred for another 3 h. The reaction was quenched by addition of saturated $NH_4Cl$ solution (20 mL). It was diluted with diethyl ether (100 mL) and the layers were separated. The organic layer was rinsed with water (3×200 mL), dried over brine and anhydrous $Na_2SO_4$ and concentrated. The crude product was purified by column chromatography eluting with 5% EtOAc in petroleum ether to yield (2S,5S)-tert-butyl 2-(3,5-bis(trifluoromethyl)benzoyl)-5-(2-chloro-5-(trifluoromethyl)phenyl)pyrrolidine-1-carboxylate (3.80 g, 6.44 mmol) as a colorless, gummy solid. $^1$H NMR (400 MHz, $CDCl_3$) δ 8.49 (d, 2H, J=12 Hz), 8.13 (d, 1H, J=15 Hz), 7.86-7.91 (m, 1H), 7.48-7.55 (m, 2H), 5.55-5.73 (m, 2H), 2.37-2.59 (m, 2H), 1.90-1.96 (m, 2H), 1.17 (s, 9H); LC-MS ESI calc'd. for $C_{25}H_{21}ClF_9NO_3$ [M-Boc]+489.88. found 490.0.

Step 3:

To a solution of (2S,5S)-tert-butyl 2-(3,5-bis(trifluoromethyl)benzoyl)-5-(2-chloro-5-(trifluoromethyl)phenyl)pyrrolidine-1-carboxylate (2.00 g, 3.39 mmol) in MeOH (20 mL), were added $NH_4OAc$ (2.61 g, 33.9 mmol) and $NaCNBH_3$ (639 mg, 10.2 mmol). The resulting reaction mixture was heated in a 100 mL pressure tube at 100° C. for 16 h. After cooling to rt, silica gel was added to the reaction mixture to make a slurry. It was purified by column chromatography to yield (2S,5S)-tert-butyl 2-((R)-amino(3,5-bis(trifluoromethyl)phenyl)methyl)-5-(2-chloro-5-(trifluoromethyl)phenyl)pyrrolidine-1-carboxylate (620 mg, 1.05 mmol). LC-MS ESI calc'd. for $C_{25}H_{24}ClF_9N_2O_2$ [M+H]+ 590.1, 592.1. found 491.0, 493.0.

Step 4:

To a solution (2S,5S)-tert-butyl 2-((R)-amino(3,5-bis(trifluoromethyl)phenyl)methyl)-5-(2-chloro-5-(trifluoromethyl)phenyl)pyrrolidine-1-carboxylate (620 mg, 1.05 mmol) in $CH_2Cl_2$ (5 mL), was added a solution of HCl in dioxane (10 mL) and the reaction was stirred at rt for 4 h. The reaction solution was concentrated, the residue was partitioned between $CH_2Cl_2$ and 10% $NaHCO_3$ aqueous solution. The aqueous layer was extracted with $CH_2Cl_2$, dried over anhydrous $Na_2SO_4$ and concentrated to yield (R)-(3,5-bis(trifluoromethyl)phenyl)((2S,5S)-5-(2-chloro-5-(trifluoromethyl)phenyl)pyrrolidin-2-yl)methanamine (525 mg, 1.05 mmol). It was carried forward to the next step without further purification. LC-MS ESI calc'd. for $C_{20}H_{16}ClF_9N_2$ [M+H]+ 491.1, 493.1. found 491.0, 493.0.

Step 5:

To a solution of (R)-(3,5-bis(trifluoromethyl)phenyl)((2S,5S)-5-(2-chloro-5-(trifluoromethyl)phenyl)pyrrolidin-2-yl)methanamine (525 mg, 1.07 mmol) in $CH_2Cl_2$ (10 mL), were added $Et_3N$ (0.45 mL, 3.21 mmol) and triphosgene (476 mg, 1.60 mmol) at 0° C. The resulting reaction mixture was allowed to warm up to rt and stirred for 3 h. It was then diluted with $CH_2Cl_2$, rinsed with 1.5 N HCl aqueous solution and water, dried over anhydrous $Na_2SO_4$ and concentrated. The crude product was purified by column chromatography eluted with 10% EtOAc in petroleum ether to yield intermediate A1 (180 mg, 0.35 mmol). $^1$H NMR (400 MHz, $CDCl_3$) δ 7.89 (m, 3H), 7.80 (s, 1H), 7.48 (d, 2H, J=2 Hz), 5.51 (s, 1H), 5.43-5.45 (d, 1H, J=9 Hz), 5.27-5.31 (t, 1H, J=8 Hz), 4.41-4.47 (m, 1H), 2.83-2.91 (m, 1H), 1.51-1.59 (m, 1H), 1.41 (m, 2H); LC-MS ESI calc'd. for $C_{21}H_{14}ClF_9N_2O$ [M+H]+ 517.1, 519.1. found 516.8, 518.8.

Intermediate A2

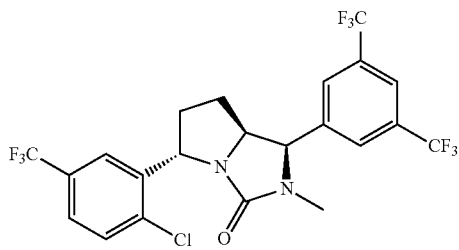

(1R,5S,7aS)-1-(3,5-bis(trifluoromethyl)phenyl)-5-(2-chloro-5-(trifluoromethyl)phenyl)-2-methyltetrahydro-1H-pyrrolo[1,2-c]imidazol-3(2H)-one To a solution of (1R,5S,7aS)-1-(3,5-bis(trifluoromethyl)phenyl)-5-(2-chloro-5-(trifluoromethyl)phenyl)tetrahydro-1H-pyrrolo[1,2-c]imidazol-3(2H)-one (120 mg, 0.23 mmol) in DMF (5 mL), stirring at 0° C., was added NaH (11 mg, 0.28 mmol) and the reaction was stirred for 30 min., after which MeI (0.02 mL, 0.35 mmol) was added and the solution was stirred at rt for 3 h. Ice was added to the reaction mixture, the layers separated and the aqueous fraction was extracted was with EtOAc. The combined organic fractions were dried over anhydrous $Na_2SO_4$ and concentrated to yield (1R,5S,7aS)-1-(3,5-bis(trifluoromethyl)phenyl)-5-(2-chloro-5-(trifluoromethyl)phenyl)-2-methyltetrahydro-1H-pyrrolo[1,2-c]imidazol-3(2H)-one (120 mg, 0.23 mmol). $^1$H NMR (400 MHz, CDCl3): δ 7.92 (s, 1H), 7.80 (s, 1H), 7.77 (s, 2H), 7.49-7.48 (m, 2H), 5.29 (t, J=8.28 Hz, 1H), 5.07 (d, J=8.80 Hz, 1H), 4.31-3.29 (m, 1H), 2.85 (s, 3H), 2.84-2.79 (m, 1H), 1.61-1.52 (m, 1H), 1.32-1.25 (m, 2H). LC-MS ESI calc'd. for $C_{22}H_{16}ClF_9N_2O$ [M+H]+ 531.09. found, 531.0.

Intermediate A3

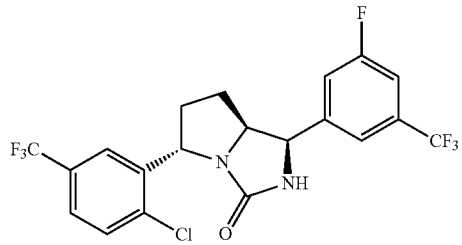

(1R,5S,7aS)-5-(2-chloro-5-(trifluoromethyl)phenyl)-1-(3-fluoro-5-(trifluoromethyl)phenyl)tetrahydro-1H-pyrrolo[1,2-c]imidazol-3(2H)-one Intermediate A3 was synthesized according to Scheme A using similar procedures as were used for the synthesis of Intermediate A1. $^1$H NMR (400 MHz, $CDCl_3$): δ 7.81 (m, 1H), 7.50-7.45 (m, 3H), 7.33 (d, J=8 Hz, 2H), 5.89 (bs, 1H), 5.36-5.34 (d, J=7 Hz, 1H), 5.26 (t, J=8 Hz, 1H), 4.42-4.36 (m, 1H), 2.89-2.82 (m, 1H), 1.60-1.50 (m, 1H), 1.38-1.31 (m, 2H). LC-MS ESI calc'd. for $C_{20}H_{14}ClF_7N_2O$ [M+H]$^+$ 469.1. found, 469.2.

Intermediate A4

(1R,5S,7aS)-5-(2-chloro-5-(trifluoromethyl)phenyl)-1-(2-(trifluoromethyl)pyridin-4-yl)tetrahydro-1H-pyrrolo[1,2-c]imidazol-3(2H)-one Intermediate A4 was synthesized according to Scheme A using similar procedures as were used for the synthesis of Intermediate A1. $^1$H NMR (400 MHz, $CDCl_3$): δ 8.80 (d, J=5.00 Hz, 1H), 7.79 (s, 1H), 7.73 (s, 1H), 7.55 (d, J=4.96 Hz, 1H), 7.50-7.45 (m, 2H), 5.75 (s, 1H), 5.36 (d, J=8.80 Hz, 1H), 5.26 (t, J=8.16 Hz, 1H), 4.47-4.40 (m, 1H), 2.90-2.83 (m, 1H), 1.55-1.51 (m, 1H), 1.41-1.36 (m, 2H). LC-MS ESI calc'd. for $C_{19}H_{14}ClF_6N_3O$ [M+H]$^+$ 450.1. found, 450.0.

Intermediate A5

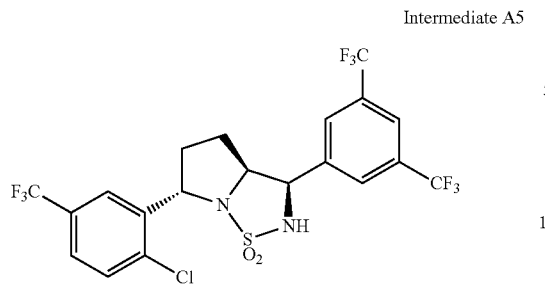

(3R,3aS,6S)-3-(3,5-bis(trifluoromethyl)phenyl)-6-(2-chloro-5-(trifluoromethyl)phenyl)hexahydropyrrolo[1,2-b][1,2,5]thiadiazole 1,1-dioxide To a solution of (R)-(3,5-bis(trifluoromethyl)phenyl)((2S,5S)-5-(2-chloro-5-(trifluoromethyl)phenyl)pyrrolidin-2-yl)methanamine (300 mg, 0.61 mmol) in pyridine (5.0 mL), was added sulfuric diamide (176 mg, 1.81 mmol) at room temperature. The reaction mixture was heated at 105° C. for 16 h. The reaction mixture was concentrated. The crude product was purified by flash column chromatography using 10% ethyl acetate in hexanes to yield (3R,3aS,6S)-3-(3,5-bis(trifluoromethyl)phenyl)-6-(2-chloro-5-(trifluoromethyl)phenyl)hexahydropyrrolo[1,2-b][1,2,5]thiadiazole 1,1-dioxide. $^1$H NMR (300 MHz, CDCl$_3$): δ 7.93 (d, J=3.54 Hz, 2H), 7.88 (s, 2H), 7.50 (d, J=1.20 Hz, 2H), 5.44-5.36 (m, 2H), 4.75 (d, J=4.05 Hz, 1H), 4.68-4.61 (m, 1H), 2.63-2.59 (m, 1H), 1.64 (t, J=11.91 Hz, 2H), 1.58-1.49 (m, 1H). LC-MS ESI calc'd. for C$_{20}$H$_{14}$ClF$_9$N$_2$O$_2$S [M–H]$^+$ 551.8. found 551.84.

Intermediate A6

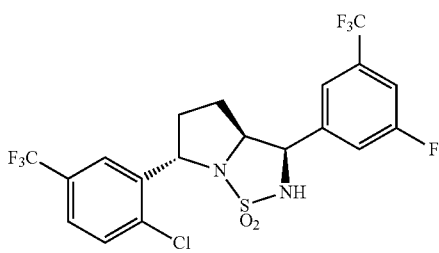

(3R,3aS,6S)-6-(2-chloro-5-(trifluoromethyl)phenyl)-3-(3-fluoro-5-(trifluoromethyl)phenyl)hexahydropyrrolo[1,2-b][1,2,5]thiadiazole 1,1-dioxide Intermediate A6 was synthesized according to Scheme A using similar procedures as were used for the synthesis of Intermediate A5. $^1$H NMR (400 MHz, DMSO-d$_6$): δ 8.13 (d, J=4.00 Hz, 1H), 7.94 (s, 1H), 7.11-7.10 (m, 4H), 7.64 (d, J=8.00 Hz, 1H), 5.25 (t, J=4.80 Hz, 1H), 5.13 (t, J=6.80 Hz, 1H), 4.75-4.71 (m, 1H), 2.39-2.37 (m, 1H), 1.61-1.51 (m, 1H), 1.47-1.38 (m, 2H). LC-MS ESI calc'd. for C$_{19}$H$_{14}$ClF$_7$N$_2$O$_2$S [M–H]$^+$ 501.04. found, 501.0.

Scheme B

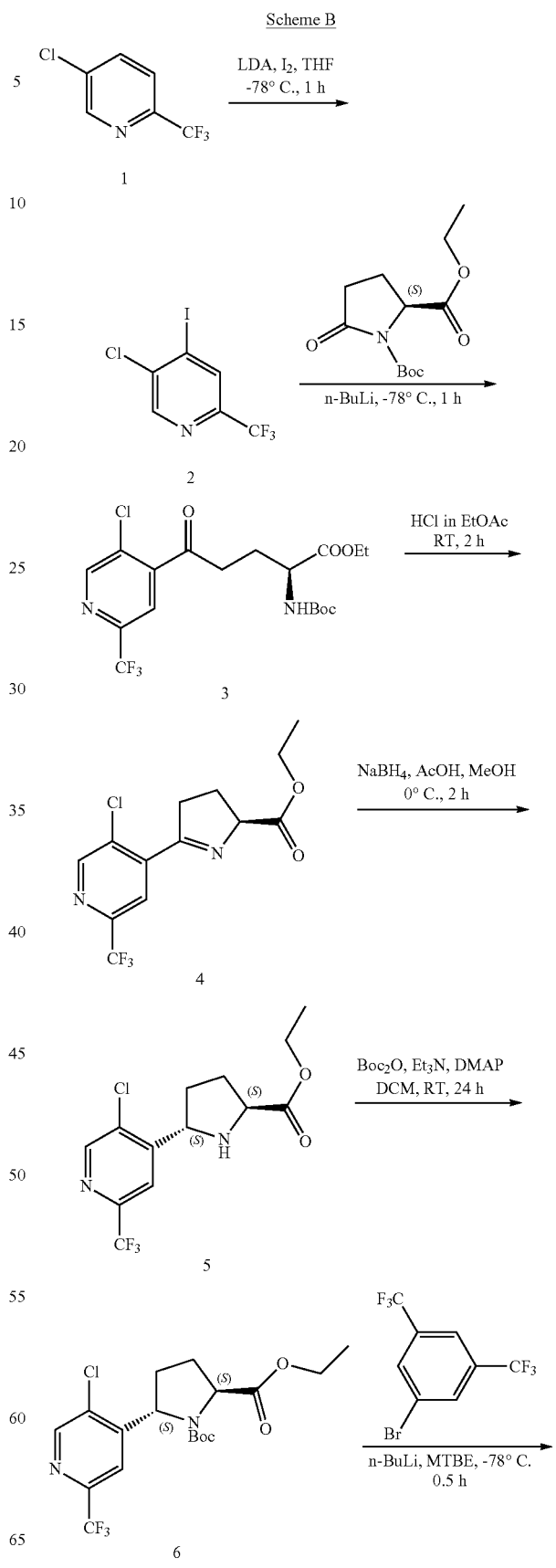

-continued

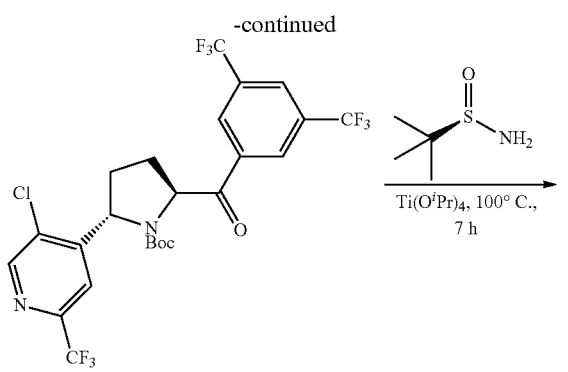

7

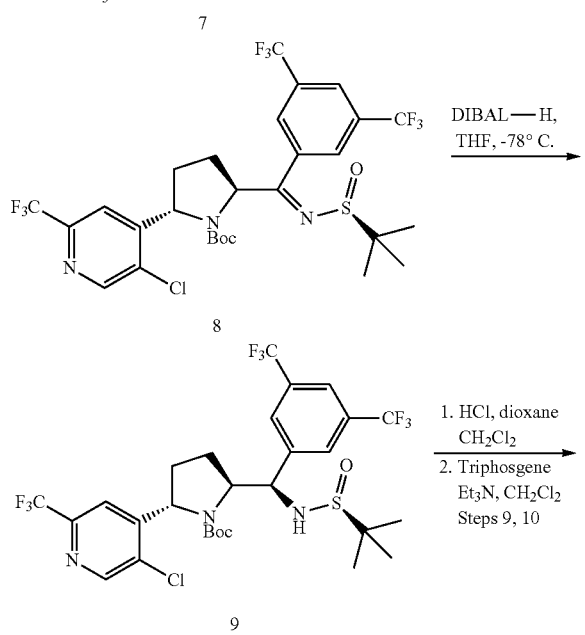

8

9

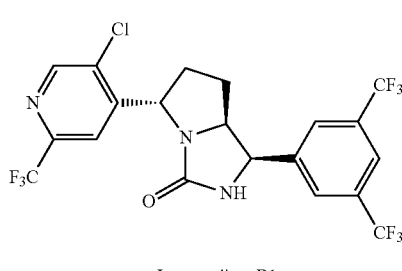

Intermediate B1

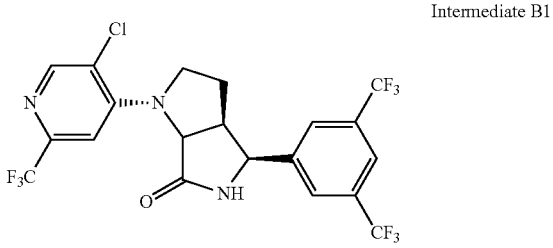

Intermediate B1

(1R,5S,7aS)-1-(3,5-bis(trifluoromethyl)phenyl)-5-(5-chloro-2-(trifluoromethyl)pyridin-4-yl)hexahydro-3H-pyrrolo[1,2-c]imidazol-3-one Step 1:

LDA (lithium diisopropyl amide) preparation: To a solution of diisopropylamine (5.8 mL, 41.3 mmol) in THF (40 mL), at −78° C. in a 250 mL 3 neck RBF, was added n-butyl lithium (1.6 M in hexane, 25.8 mL, 6.49 mmol) and the resulting solution was stirred at that temperature for 0.5 h.

To a solution of iodine (8.37 g, 33.0 mmol) and 5-chloro-2-(trifluoromethyl) pyridine (10 g, 55.08 mmol) in THF (100 mL) at −78° C. in a 500 mL 3 neck RBF, was added the above prepared LDA solution through a canula and the resulting solution was stirred at that temperature for 1 h. The reaction was stopped by the addition of saturated NH$_4$Cl solution (50 mL) and extracted with MTBE (2×100 mL). The organic layer was washed with water (2×50 mL), dried over anhydrous Na$_2$SO$_4$ and concentrated. The crude product was purified by column chromatography (2% EtOAc in petroleum ether) to yield 5-chloro-4-iodo-2-(trifluoromethyl)pyridine. $^1$H NMR (300 MHz, DMSO-d$_6$): δ8.81 (s, 1H), 8.49 (s, 1H); GC-MS calc'd. for C$_6$H$_2$ClF$_3$IN [M+H]$^+$ 307.89. found 307.0.

Step 2:

To a solution of 5-chloro-4-iodo-2-(trifluoromethyl)pyridine (18.2 g, 59.2 mmol) in diethylether (200 mL), at −78° C. in a 1 L 3 neck RBF, was added n-butyl lithium (1.6 M in hexane, 44.5 mL, 71.1 mmol). The resulting solution was stirred at that temperature for 10 minutes and ethyl-N-Boc-(S)-pyroglutamate (16.75 g, 65.2 mmol) in diethylether (130 mL) was added slowly, and the resulting solution was stirred at that temperature for 1 h. The reaction was stopped by the addition of saturated NH$_4$Cl solution (150 mL) and extracted with EtOAc (2×250 mL). The organic layer was washed with water (2×150 mL), dried over anhydrous Na$_2$SO$_4$ and concentrated to yield ethyl (S)-2-((tert-butoxycarbonyl)amino)-5-(5-chloro-2-(trifluoromethyl)pyridin-4-yl)-5-oxopentanoate which was carried forward to the next step without further purification.

Step 3:

A solution of ethyl (S)-2-((tert-butoxycarbonyl)amino)-5-(5-chloro-2-(trifluoromethyl)pyridin-4-yl)-5-oxopentanoate (18 g, crude) in HCl in EtOAc (200 mL) in a 500 mL RBF was stirred at room temperature for 2 h. The reaction solution was concentrated and the residue obtained was taken up in EtOAc (250 mL), washed with aqueous 10% NaHCO$_3$ (2×150 mL), water (2×150 mL), dried over anhydrous Na$_2$SO$_4$ and concentrated. The crude product was purified by column chromatography (2-7% EtOAc in petroleum ether) to yield ethyl (S)-5-(5-chloro-2-(trifluoromethyl)pyridin-4-yl)-3,4-dihydro-2H-pyrrole-2-carboxylate. $^1$H NMR (400 MHz, CDCl$_3$): δ 8.75 (s, 1H), 8.06 (s, 1H), 4.97-4.93 (m, 1H), 4.28 (dd, J=7.2 Hz, J=14.4 Hz, 2H), 3.29-3.24 (m, 1H), 3.19-3.12 (m, 1H), 2.47-2.31 (m, 2H), 1.35 (t, J=7.2 Hz, 3H); UPLC-MS calc'd. for C$_{13}$H$_{12}$ClF$_3$N$_2$O$_2$ [M+H]$^+$ 321.05. found 321.2.

Step 4:

To a solution of ethyl (S)-5-(5-chloro-2-(trifluoromethyl) pyridin-4-yl)-3,4-dihydro-2H-pyrrole-2-carboxylate (5.0 g, 15.6 mmol) in MeOH: AcOH (1:1; 30 mL) at −30° C. in a 250 mL 3 neck RBF, was added sodium borohydride (1.18 g, 31.2 mmol) and the resulting solution was stirred at 0° C. for 2 h. The reaction mixture was quenched with water (25 mL) and concentrated. The residue obtained was taken up in EtOAc (150 mL), washed with aqueous 10% NaHCO$_3$ (2×100 mL), water (2×100 mL), dried over anhydrous Na₂SO₄ and concentrated. The crude product was purified by column chromatography (5% EtOAc in petroleum ether) to yield ethyl (2S,5S)-5-(5-chloro-2-(trifluoromethyl)pyridin-4-yl)pyrrolidine-2-carboxylate. $^1$H NMR (400 MHz, CDCl₃): δ 8.58 (s, 1H), 8.14 (s, 1H), 4.79 (t, J=7.4 Hz, 1H), 4.25 (dd, J=7.2 Hz, J=14.3 Hz, 2H), 4.07 (dd, J=5.3 Hz, J=8.0 Hz, 1H), 2.49-2.42 (m, 1H), 2.29-2.22 (m, 1H), 2.07-2.01 (m, 1H), 1.62-1.55 (m, 1H), 1.32 (t, J=7.1 Hz, 3H); LC-MS ESI calc'd. for C₁₃H₁₄F₃N₂O₂ [M+H]⁺ 323.7. found 323.2.

Step 5:

To a solution of ethyl (2S,5S)-5-(5-chloro-2-(trifluoromethyl)pyridin-4-yl)pyrrolidine-2-carboxylate (1.6 g, 4.96 mmol) in dichloromethane (8 mL) at 0° C. in a 50 mL RBF, was added triethyl amine (1.74 mL, 12.4 mmol) and DMAP (1.5 g, 12.4 mmol) and the resulting solution was stirred at room temperature for 16 h. The reaction solution was diluted with dichloromethane (50 mL), washed with 1.5N HCl (2×100 mL), water (2×100 mL), dried over anhydrous Na₂SO₄ and concentrated. The crude product was purified by column chromatography (7% EtOAc in petroleum ether) to yield 1-(tert-butyl) 2-ethyl (2S,5S)-5-(5-chloro-2-(trifluoromethyl)pyridin-4-yl)pyrrolidine-1,2-dicarboxylate. The crude material was judged to have a 2:3 diastereomeric ratio by $^1$H NMR analysis. UPLC-MS calc'd. for C₁₈H₂₂ClF₃N₂O₄ [M+H]⁺ 423.8. found 423.3.

Step 6:

To a N₂ purged solution of 1-(tert-butyl) 2-ethyl (2S,5S)-5-(5-chloro-2-(trifluoromethyl)pyridin-4-yl)pyrrolidine-1,2-dicarboxylate (1.7 g, 4.0 mmol) and 1-bromo-3,5-bis(trifluoromethyl)benzene (2.95 g, 10.1 mmol) in MTBE (25 mL) stirring at −78° C. in a 250 mL RBF was added dropwise n-BuLi (1.6 M in hexanes, 5.8 mL, 9.2 mmol), and the resulting solution was stirred at that temperature for 0.5 h. The reaction was stopped by the addition of saturated NH₄Cl solution (25 mL), diluted with EtOAc (100 mL) and the layers were separated. The organic layer was washed with water (2×100 mL), dried over anhydrous Na₂SO₄ and concentrated. The crude product was purified by Isolera column chromatography (6% EtOAc in petroleum ether) to yield tert-butyl (2S,5S)-2-(3,5-bis(trifluoromethyl)benzoyl)-5-(5-chloro-2-(trifluoromethyl)pyridin-4-yl)pyrrolidine-1-carboxylate. UPLC-MS calc'd. for C₂₄H₂₀ClF₉N₂O₃ [M+H]⁺ 591.8. found 591.3.

Step 7:

To a solution of tert-butyl (2S,5S)-2-(3,5-bis(trifluoromethyl)benzoyl)-5-(5-chloro-2-(trifluoromethyl)pyridin-4-yl)pyrrolidine-1-carboxylate (1.4 g, 2.37 mmol) and (R)-2-methylpropane-2-sulfinamide (1.44 g, 11.9 mmol) in THF (5 mL) at room temperature in a 100 mL RBF was added titanium (IV) ethoxide (14 mL), and the resulting solution was heated at 70° C. for 12 h. Water (100 mL) was added to the reaction mixture. The solid that formed was filtered out, and the filtrate was extracted with EtOAc (3×50 mL). The organic layer was washed with water (2×50 mL), dried over anhydrous Na₂SO₄ and concentrated. The crude product was purified by column chromatography (4-8% EtOAc in petroleum ether) to yield tert-butyl (2S,5S)-2-((E)-(3,5-bis(trifluoromethyl)phenyl)((tert-butylsulfinyl)imino)methyl)-5-(5-chloro-2-(trifluoromethyl)pyridin-4-yl)pyrrolidine-1-carboxylate. $^1$H NMR (400 MHz, CD₃OD): δ8.76 (s, 1H), 8.21 (bs, 1H), 8.16 (bs, 1H), 8.08 (s, 1H), 5.39 (d, J=9.0 Hz, 1H), 5.24 (d, J=5.6 Hz, 1H), 2.91-2.81 (m, 1H), 2.24-2.17 (m, 1H), 2.05-2.03 (m, 1H), 1.97-1.90 (m, 1H), 1.55 (bs, 1H), 1.30 (s, 9H), 1.22 (s, 9H); UPLC-MS calc'd. for C₂₈H₂₉ClF₉N₃O₃S[M-(t-bu)]⁺ 637.98. found 638.2.

Step 8:

To a solution of tert-butyl (2S,5S)-2-((E)-(3,5-bis(trifluoromethyl)phenyl)((tert-butylsulfinyl)imino)methyl)-5-(5-chloro-2-(trifluoromethyl)pyridin-4-yl)pyrrolidine-1-carboxylate (600 mg, 0.86 mmol) in THF (6 mL), at −78° C. in a 100 mL 3 neck RBF was added, DIBAL-H (1.0 M in toluene, 1.73 mL, 1.72 mmol) and the resulting solution was stirred at that temperature for 0.5 h. The reaction was stopped by the addition of saturated NH₄Cl solution (20 mL), stirred at rt for 0.5 h. The solid that formed was filtered out, and the filtrate was extracted with EtOAc (3×50 mL). The organic layer was washed with water (2×50 mL), dried over anhydrous Na₂SO₄ and concentrated. The crude product was purified by column chromatography (15-20% EtOAc in petroleum ether) to yield tert-butyl (2S,5S)-2-((1R)-(3,5-bis(trifluoromethyl)phenyl)((tert-butylsulfinyl)amino)methyl)-5-(5-chloro-2-(trifluoromethyl)pyridin-4-yl)pyrrolidine-1-carboxylate. UPLC-MS calc'd. for C₂₈H₃₁ClF₉N₃O₃S[M+H]⁺ 696.16. found 696.3.

Step 9:

To a solution of tert-butyl (2S,5S)-2-((1R)-(3,5-bis(trifluoromethyl)phenyl)((tert-butylsulfinyl)amino)methyl)-5-(5-chloro-2-(trifluoromethyl)pyridin-4-yl)pyrrolidine-1-carboxylate (480 mg, 0.69 mmol) in dichloromethane (1 mL), in a 50 mL RBF, was added HCl in dioxane (8 mL) and the resulting solution was stirred at room temperature for 16 hours. The reaction solution was concentrated, the residue was partitioned between EtOAc (50 mL) and aqueous 10% NaHCO₃ solution (20 mL), and the layers were separated. The organic layer was washed with water (2×50 mL), dried over anhydrous Na₂SO₄ and concentrated to yield (R)-(3,5-bis(trifluoromethyl)phenyl)((2S,5S)-5-(5-chloro-2-(trifluoromethyl)pyridin-4-yl)pyrrolidin-2-yl)methanamine. UPLC-MS calc'd. for C₁₉H₁₅ClF₉N₃[M+H]⁺ 492.7. found 492.2.

Step 10:

To a solution of (R)-(3,5-bis(trifluoromethyl)phenyl)((2S,5S)-5-(5-chloro-2-(trifluoromethyl)pyridin-4-yl)pyrrolidin-2-yl)methanamine (250 mg, 0.51 mmol) in CH₂Cl₂ (12.5 mL), stirring at 0° C., were added Et₃N (0.21 mL, 1.52 mmol) and triphosgene (226 mg, 0.76 mmol) and the reaction was allowed to stir at that temperature for 1 h. The reaction mixture was concentrated. The crude product was purified by Isolera column chromatography (15% EtOAc in petroleum ether) to yield Intermediate B1 (1R,5S,7aS)-1-(3,5-bis(trifluoromethyl)phenyl)-5-(5-chloro-2-(trifluoromethyl)pyridin-4-yl)hexahydro-3H-pyrrolo[1,2-c]imidazol-3-one. $^1$H NMR (400 MHz, CDCl₃): δ 8.65 (s, 1H), 7.92 (bs, 1H), 7.88 (m, 3H), 5.49 (bs, 1H), 5.46 (d, J=8.7 Hz, 1H), 5.26 (t, J=8.4 Hz, 1H), 4.47-4.40 (m, 1H), 2.93-2.90 (m, 1H), 1.39-1.26 (m, 2H); LC-MS ESI calc'd. for C₂₀H₁₃ClF₉N₃O [M−H]⁺ 516.7. found 516.0.

Scheme C

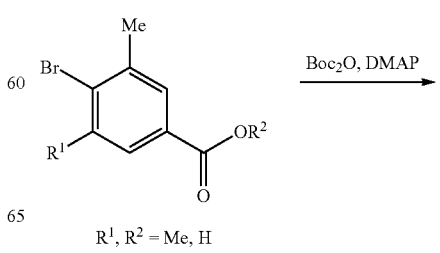

R¹, R² = Me, H

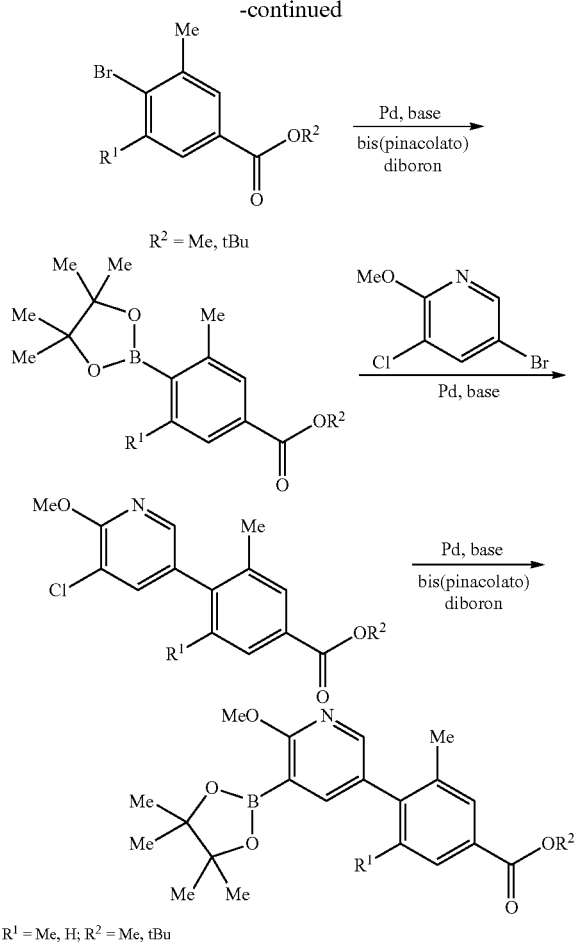

Intermediate C1

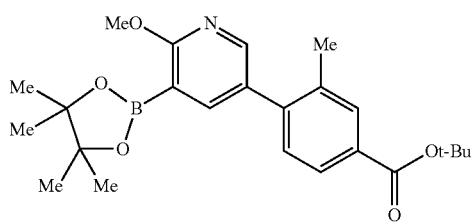

tert-butyl 4-[6-methoxy-5-(4,4,5,5-tetramethyl-1,3, 2-dioxaborolan-2-yl)pyridin-3-yl]-3-methylbenzoate Step 1:

To a 250 mL RBF was added 4-bromo-3-methylbenzoic acid (10 g, 46.5 mmol), DMAP (8.52 g, 69.8 mmol) and tert-butyl alcohol (100 mL). Di-tert-butyl dicarbonate (12.96 mL, 55.8 mmol) was added via syringe to the solution, which caused vigorous bubbling, foaming and the loss of some material. The remaining reaction mixture was heated at 70° C. overnight. The reaction was cooled to room temperature and the volatiles were removed under reduced pressure. Crude material was diluted with ethyl acetate: hexanes (1:4, 200 mL) and was washed sequentially with 5% aqueous KOH (200 mL) and saturated aqueous ammonium chloride (2×100 mL). The organics were dried over sodium sulfate, filtered and concentrated before purification by column chromatography to yield tert-Butyl 4-bromo-3-methylbenzoate. $^1$H NMR (500 MHz, CDCl$_3$) δ 7.87 (s, 1H), 7.67 (d, J=8.3 Hz, 1H), 7.60 (d, J=8.2 Hz, 1H), 2.47 (s, 3H), 1.62 (s, 9H).

Step 2:

To a 250 mL RBF was added 1,1'-bis(di-tert-butylphosphino)ferrocene palladium dichloride (0.317 g, 0.487 mmol), tert-butyl 4-bromo-3-methylbenzoate (6.6 g, 24.34 mmol), bis(pinacolato)diboron (7.42 g, 29.2 mmol), potassium acetate (5.97 g, 60.9 mmol) and dioxane (25 mL). The system was flushed with nitrogen and was heated at 125° C. overnight. The reaction was cooled to room temperature and was diluted with ethyl acetate:hexanes (1:9, 120 mL) and then was washed sequentially with water (150 mL) and then brine (50 mL). The organics were dried over sodium sulfate, filtered and concentrated before purification by column chromatography. tert-Butyl 3-methyl-4-(4,4,5,5-tetramethyl-1,3,2-dioxaborolan-2-yl)benzoate was isolated as a crystalline solid. $^1$H NMR indicated it is about 70% pure. $^1$H NMR (500 MHz, CDCl$_3$) δ 7.8 (m, 3H), 2.60 (s, 3H), 1.58 (s, 9H), 1.39 (s, 12H).

Step 3:

To a 250 mL RBF was added 5-bromo-3-chloro-2-methoxypyridine (1.5 g), tribasic potassium phosphate (2.86 g, 13.5 mmol), bis(diphenylphosphino)ferrocene]palladium (II) dichloromethane adduct (0.275 g, 6.74 mmol), tert-butyl 3-methyl-4-(4,4,5,5-tetramethyl-1,3,2-dioxaborolan-2-yl) benzoate (2.27 g, 7.13 mmol), dioxane (50 mL) and water (3 mL). The flask was sealed and was stirred at 80° C. overnight. The reaction was cooled to room temperature, diluted with ethyl acetate, washed with water, filtered and concentrated. The resultant residue was purified by column chromatography to yield tert-butyl 4-(5-chloro-6-methoxypyridin-3-yl)-3-methylbenzoate. MS ESI calc'd. for $C_{18}H_{21}ClNO_3$ [M+H]+ 334.1. found 334.0.

Step 4:

To a 250 mL RBF was added tert-butyl 4-(5-chloro-6-methoxypyridin-3-yl)-3-methylbenzoate (4.5 g, 13.5 mmol), bis(pinacolato)diboron (6.85 g, 27.0 mmol), potassium acetate (3.97 g, 40.4 mmol), and chloro(2-dicyclohexylphosphino-2',4',6'-triisopropyl-1,1'-biphenyl)[2-(2'-amino-1,1'-biphenyl)]palladium(II) (0.212 g, 0.27 mmol) followed by anhydrous dioxane (50 mL). The system was evacuated and backfilled with nitrogen (3×) and was heated to 120° C. for 2 hours. The mixture was cooled, filtered over Celite® (ethyl acetate wash) and was concentrated. The residue was purified by column chromatography to afford tert-butyl 4-[6-methoxy-5-(4,4,5,5-tetramethyl-1,3,2-dioxaborolan-2-yl)pyridin-3-yl]-3-methylbenzoate. MS ESI calc'd. for $C_{24}H_{33}BNO_5$ [M+H]+ 426.2. found 426.0.

Scheme D

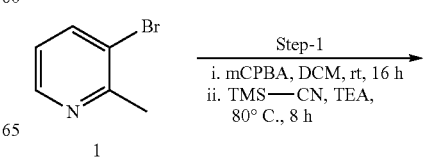

1

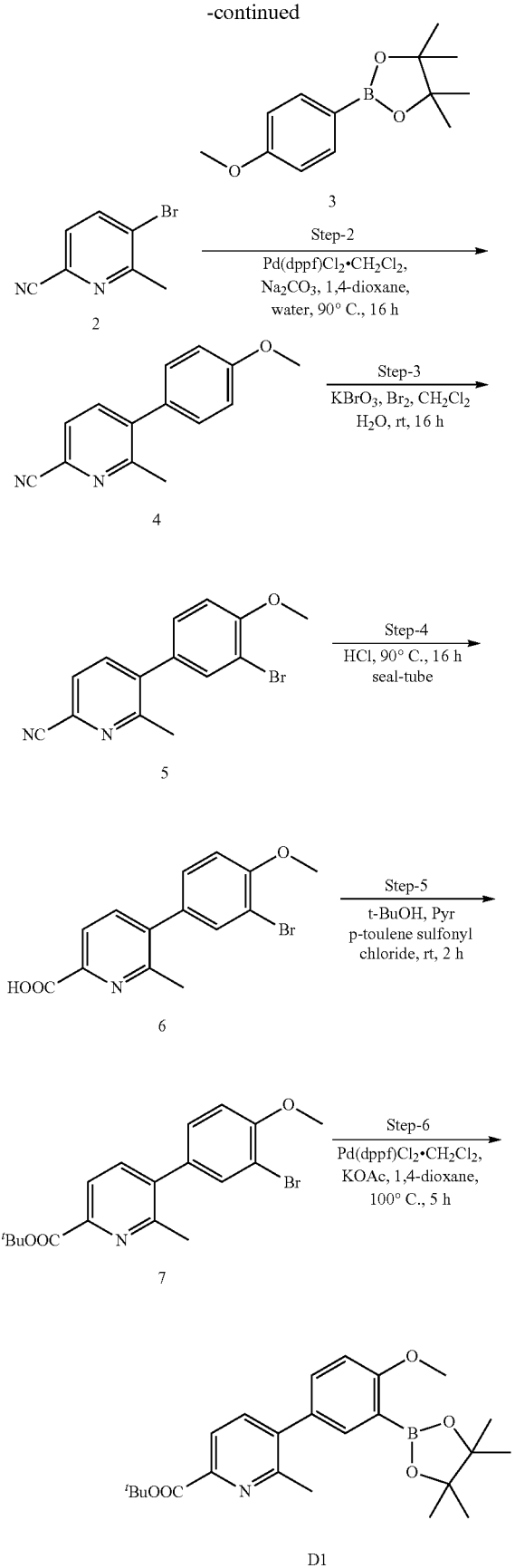

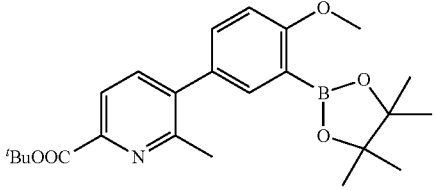

Intermediate D1 tert-butyl 5-(4-methoxy-3-(4,4,5,5-tetramethyl-1,3,2-dioxaborolan-2-yl)phenyl)-6-methylpicolinate Step 1:

To a solution of 3-bromo-2-methylpyridine (5.0 g, 28.7 mmol) in dichloromethane (100 mL) at 0° C. in a 250 mL 3 neck RBF, was added m-CPBA (10.25 g, 57.5 mmol). The resulting solution was stirred at room temperature for 16 h. The reaction solution was concentrated to remove the solvent. The crude product was purified by column chromatography (30% EtOAc in petroleum ether) to yield the intermediate N-oxide compound which was taken up in triethylamine (50 mL) and TMS-CN (50 mL) in a 250 mL sealed tube and heated at 80° C. for 8 h. The reaction solution was concentrated. The crude product was purified by column chromatography (10% EtOAc in petroleum-ether) to yield 5-bromo-6-methylpicolinonitrile. $^1$H NMR (300 MHz, MeOD): δ 8.15 (d, J=8.16 Hz, 1H), 7.59 (d, J=8.13 Hz, 1H), 2.67 (s, 3H).

Step 2:

To a solution of 5-bromo-6-methylpicolinonitrile (5.0 g, 25.2 mmol) in 1,4-dioxane (50 mL) in a 100 mL sealed tube was added 2-(4-methoxyphenyl)-4,4,5,5-tetramethyl-1,3,2-dioxaborolane (4.21 g, 27.7 mmol), and the reaction solution was deoxygenated by alternately evacuating and purging with argon for 10 minutes. Na$_2$CO$_3$ (6.7 g, 63.2 mmol) in water (5 mL) was added, and the mixture was again deoxygenated by alternately evacuating and purging with argon for 10 minutes. Pd(dppf)Cl$_2$.CH$_2$Cl$_2$ (461 mg, 0.63 mmol) was added and the reaction mixture was similarly deoxygenated for 5 minutes. The reaction flask was sealed and the mixture was heated at 90° C. for 16 h. After the completion of the reaction, the crude product was diluted with EtOAc (100 mL), washed with water (2×50 mL), dried over anhydrous Na$_2$SO$_4$ and concentrated. The crude product was purified by Isolera (15% EtOAc in petroleum-ether) to yield 5-(4-methoxyphenyl)-6-methylpicolinonitrile. $^1$H NMR (400 MHz, MeOD): δ 7.80-7.77 (m, 2H), 7.35 (dd, J=2.20, 6.66 Hz, 2H), 7.07 (dd, J=2.12, 6.66 Hz, 2H), 3.88 (s, 3H), 2.54 (s, 3H). LC-MS ESI calc'd. for C$_{14}$H$_{12}$N$_2$O [M+H]$^+$ 225.2. found 225.2.

Step 3:

To a solution of 5-(4-methoxyphenyl)-6-methylpicolinonitrile (12.3 g, 55.6 mmol) in dichloromethane (20 mL) and water (60 mL) in a 500 mL 3 neck RBF, was added KBrO$_3$ (1.85 g, 11.1 mmol) followed by dropwise addition of Br$_2$ (2.18 mL, 41.7 mmol) for 10 minutes. The resulting solution was stirred at room temperature for 16 h. The reaction mixture was diluted with dichloromethane (200 mL), and the layers were separated. The organic layer was washed with saturated sodium thiosulphate solution (2×100 mL), water (1×100 mL), dried over anhydrous Na$_2$SO$_4$, and concentrated. The crude product was purified by column chromatography (5% EtOAc in petroleum-ether) to yield 5-(3-bromo-4-methoxyphenyl)-6-methylpicolinonitrile. $^1$H NMR (300 MHz, CDCl$_3$): δ 7.64-7.58 (m, 2H), 7.52 (d, J=2.16 Hz, 1H), 7.25 (dd, J=2.19, 8.91 Hz, 1H), 7.00 (d, J=8.49 Hz, 1H), 3.97 (s, 3H), 2.56 (s, 3H). LC-MS calc'd. for C$_{14}$H$_{11}$BrN$_2$O [M+H]$^+$ 303.1. found 305.0.

Step 4:

A solution of 5-(3-bromo-4-methoxyphenyl)-6-methylpicolinonitrile (5.0 g, 16.5 mmol) in 9N HCl (100 mL) in a 250 mL sealed tube was heated to 90° C. for 16 h. The reaction solution was concentrated under reduced pressure to remove the solvent and was co-evaporated with toluene (2×50 mL) to yield 5-(3-bromo-4-methoxyphenyl)-6-methylpicolinic acid. $^1$H NMR (300 MHz, DMSO-d$_6$): δ 7.95 (d, J=7.86 Hz, 1H), 7.82 (d, J=7.89 Hz, 1H), 7.64 (d, J=2.13 Hz, 1H), 7.42 (dd, J=2.07, 8.35 Hz, 1H), 7.20 (d, J=8.67 Hz, 1H), 3.79 (s, 3H), 2.48 (s, 3H). LC-MS calc'd. for C$_{14}$H$_{12}$BrNO$_3$[M+H]$^+$ 323.1. found 325.0.

Step 5:

To a solution of 5-(3-bromo-4-methoxyphenyl)-6-methylpicolinic acid (6.4 g, 19.87 mmol) in t-butanol (40 mL), was added pyridine (9.63 mL, 119.2 mmol) slowly. The reaction mixture was cooled to 0° C. and 4-toluenesulfonyl chloride (370 mg, 1.94 mmol) was added. The resulting solution was stirred at room temperature for 2 h. The reaction was quenched by the addition of saturated NaHCO$_3$ solution (20 mL) and stirred for 30 mins. The reaction solution was extracted with MTBE (2×100 mL). The organic layer was washed with water (1×50 mL), dried over anhydrous Na$_2$SO$_4$ and concentrated. The crude product was purified by column chromatography (2% MeOH in dichloromethane) to yield tert-butyl 5-(3-bromo-4-methoxyphenyl)-6-methylpicolinate. $^1$H NMR (300 MHz, CDCl$_3$): δ 7.90 (d, J=7.86 Hz, 1H), 7.59 (d, J=7.92 Hz, 1H), 7.52 (d, J=2.10 Hz, 1H), 7.24 (dd, J=2.13, 8.45 Hz, 1H), 6.98 (d, J=8.46 Hz, 1H), 3.96 (s, 3H), 2.60 (s, 3H), 1.64 (s, 9H). LC-MS calc'd. for C$_{18}$H$_{20}$BrNO$_3$ [M+H]$^+$ 378.1. found 380.0.

Step 6:

To a solution of tert-butyl 5-(3-bromo-4-methoxyphenyl)-6-methylpicolinate (500 mg, 1.32 mmol) in 1,4-dioxane (10 mL) in a 50 mL sealed tube were added 4,4,4',4',5,5,5',5'-octamethyl-2,2'-bi(1,3,2-dioxaborolane) (502 mg, 1.98 mmol), KOAc (392 mg, 3.96 mmol), and the reaction solution was deoxygenated by alternately evacuating and purging with argon for 10 minutes. Pd(dppf)Cl$_2$.CH$_2$Cl$_2$ (108 mg, 0.13 mmol) was added and the reaction was again deoxygenated for 5 minutes. The reaction flask was sealed and the mixture was heated at 100° C. for 5 h. The reaction was then diluted with EtOAc (50 mL), washed with water (1×25 mL), dried over anhydrous Na$_2$SO$_4$ and concentrated. The crude product was purified by Isolera (18% EtOAc in petroleum-ether) to yield tert-butyl 5-(4-methoxy-3-(4,4,5,5-tetramethyl-1,3,2-dioxaborolan-2-yl)phenyl)-6-methylpicolinate. LC-MS calc'd. for C$_{24}$H$_{32}$BNO$_5$ [M+H]$^+$ 426.3. found 426.2.

Scheme E:

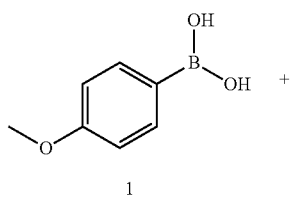

1

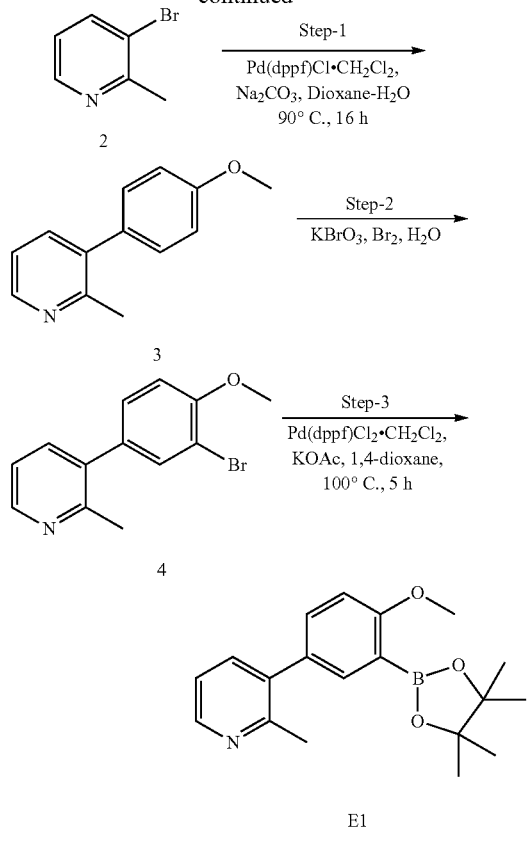

Intermediate E1

3-(4-methoxy-3-(4,4,5,5-tetramethyl-1,3,2-dioxaborolan-2-yl)phenyl)-2-methylpyridine Step 1:

To a solution of 3-bromo-2-methylpyridine (20.0 g, 116.2 mmol) in 1,4-dioxane (150 mL) in a 500 mL sealed tube was added (4-methoxyphenyl)boronic acid (19.4 g, 127.6 mmol), and the reaction solution was deoxygenated by alternately evacuating and purging with argon for 5 minutes. Na$_2$CO$_3$ (30.7 g, 290.1 mmol) in water (75 mL) was added, and the reaction was again deoxygenated by alternately evacuating and purging with argon for 10 minutes. Pd(dppf)Cl$_2$.CH$_2$Cl$_2$ (2.5 g, 3.4 mmol) was added and the reaction was similarly deoxygenated for 5 minutes. The reaction flask was sealed and the mixture was heated at 90° C. for 16 h. The reaction solution was concentrated, and the residue that was obtained was diluted with EtOAc (300 mL), washed with water (2×100 mL), dried over anhydrous Na$_2$SO$_4$ and concentrated. The crude product was purified by Isolera (15% EtOAc in petroleum-ether) to yield 3-(4-methoxyphenyl)-2-methylpyridine. ¹H NMR (300 MHz, CDCl₃): δ 8.47 (dd, J=1.56, 4.83 Hz, 1H), 7.50 (dd, J=1.56, 7.63 Hz, 1H), 7.27-7.22 (m, 2H), 7.17 (dd, J=4.86, 7.60 Hz, 1H), 6.99-6.96 (m, 2H), 3.86 (s, 3H), 2.52 (s, 3H). LC-MS calc'd. for $C_{13}H_{13}NO$ [M+H]⁺ 200.2. found 199.8.

Step 2:

To a solution of 3-(4-methoxyphenyl)-2-methylpyridine (17.5 g, 87.9 mmol) in dichloromethane (20 mL) and water (80 mL), in a 500 mL 3 neck RBF, was added KBrO₃ (2.93 g, 17.6 mmol) followed by dropwise addition of Br₂ (3.39 mL, 65.94 mmol) for 10 minutes. The resulting solution was stirred at room temperature for 16 h. The reaction solution was diluted with dichloromethane (200 mL), and the layers were separated. The organic layer was washed with saturated sodium thiosulphate solution (2×100 mL), water (1×100 mL), dried over anhydrous Na₂SO₄ and concentrated. The crude product was purified by column chromatography (5% EtOAc in petroleum-ether) to yield 3-(3-bromo-4-methoxyphenyl)-2-methylpyridine. ¹H NMR (300 MHz, DMSO-d6): δ 8.72 (d, J=5.43 Hz, 1H), 8.22 (d, J=7.83 Hz, 1H), 7.80-7.76 (m, 1H), 7.73 (d, J=2.10 Hz, 1H), 7.48 (dd, J=2.10, 8.49 Hz, 1H), 7.26 (d, J=8.58 Hz, 1H), 3.91 (s, 3H), 2.60 (s, 3H). LC-MS calc'd. for $C_{13}H_{12}BrNO$ [M+H]⁺ 278.1. found 280.0.

Step 3:

To a solution of 3-(3-bromo-4-methoxyphenyl)-2-methylpyridine (500 mg, 1.80 mmol) in 1,4-dioxane (10 mL) in a 50 mL sealed tube were added 4,4,4',4',5,5,5',5'-octamethyl-2,2'-bi(1,3,2-dioxaborolane) (913 mg, 3.59 mmol) and KOAc (533 mg, 5.39 mmol), and the reaction solution was deoxygenated by alternately evacuating and purging with argon for 10 minutes. Dichlorobis(triphenylphosphine)palladium (126 mg, 0.18 mmol) was added and the reaction was again deoxygenated for 5 minutes. The reaction flask was sealed and the mixture was heated at 90° C. for 12 h. The reaction was then diluted with EtOAc (50 mL), washed with water (1×25 mL), dried over anhydrous Na₂SO₄ and concentrated. The crude product was purified by Isolera (18% EtOAc in petroleum-ether) to yield 3-(4-methoxy-3-(4,4,5,5-tetramethyl-1,3,2-dioxaborolan-2-yl)phenyl)-2-methylpyridine. LC-MS calc'd. for $C_{19}H_{24}BNO_3$ [M+H]⁺ 325.2. found 326.2.

EXAMPLES

The following schemes and examples are provided so that the invention will be more fully appreciated and understood. The schemes and examples are illustrative and are not to be construed as limiting the invention. Starting materials are made using known procedures or as shown below.

The compounds of the present invention can be synthesized according to the general scheme outlined below. The examples, which are CETP inhibitors based on the assay data provided in the examples, were synthesized using the procedures described below. The starting materials in the schemes are commercially available or are readily synthesized by a person skilled in the art.

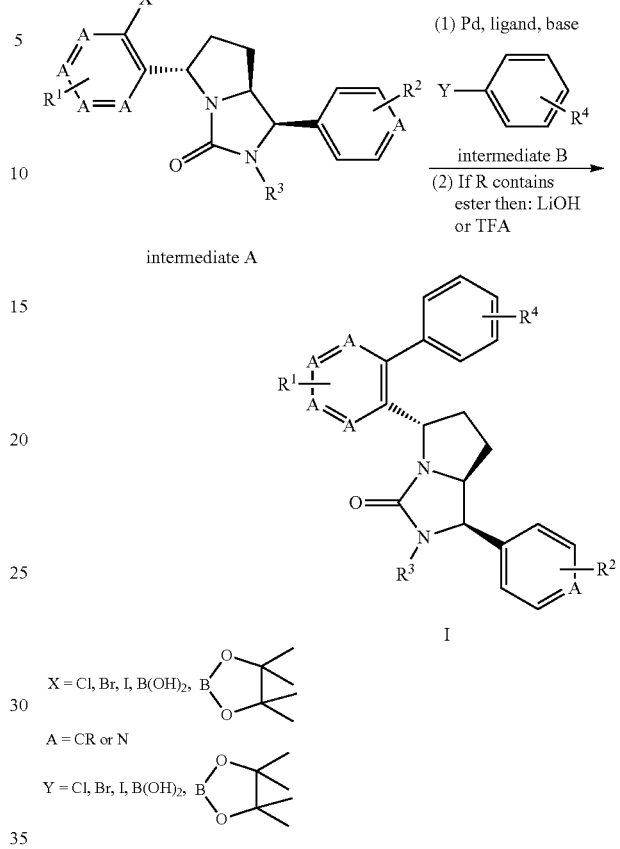

Scheme 1

In accordance with Scheme 1, a cross-coupling reaction between Intermediate A and an appropriately functionalized boronic acid/ester/halide (intermediate B) provides compounds of the general formula (I). Some of the intermediates B were synthesized according to published procedures in WO 2012058187. In cases where an ester group is present in the final product, a saponification or hydrolysis may subsequently be carried out to generate the acid.

Example 1

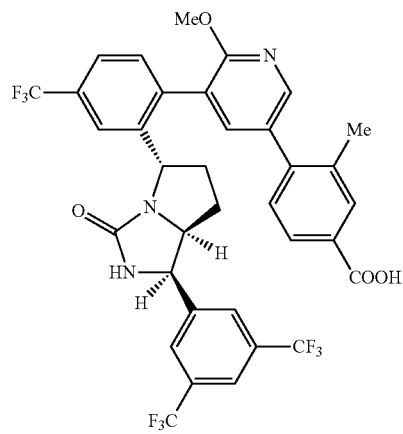 [SMILES: COc1ncc(-c2ccc(C(=O)O)cc2C)cc1-c1ccc(C(F)(F)F)cc1[C@@H]1CC[C@H]2[C@@H](c3cc(C(F)(F)F)cc(C(F)(F)F)c3)NC(=O)N12]

4-(5-(2-((1R,5 S,7aS)-1-(3,5-bis(trifluoromethyl) phenyl)-3-oxohexahydro-1H-pyrrolo[1,2-c]imidazol-5-yl)-4-(trifluoromethyl)phenyl)-6-methoxypyridin-3-yl)-3-methylbenzoic acid Step 1:

To a 2-5 ml microwave reaction vial was charged intermediate A1 (20 mg, 0.039 mmol) along with methyl 4-(6-methoxy-5-(4,4,5,5-tetramethyl-1,3,2-dioxaborolan-2-yl) pyridin-3-yl)-3-methylbenzoate (19.46 mg, 0.043 mmol), potassium phosphate (18.07 mg, 0.085 mmol) and chloro (2-dicyclohexylphosphino-2',4',6'-triisopropyl-1,1'-biphenyl)[2-(2-aminoethyl)phenyl)]palladium(II) (XPhos Pre-Catalyst, Aldrich, 1.430 mg, 1.935 µmol). The vial was sealed and degassed and refilled with nitrogen. Solvent THF (1 ml) and Water (0.1 ml) were then added and the vial was degassed again. The mixture was then exposed to microwave irradiation at 100° C. for 30 min. The mixture was then diluted with ethyl acetate (5 ml), filtered through a syringe filter, and was washed with ethyl acetate (2×1 mL). The filtrate was concentrated and the residue was purified by MPLC (4 g silica gel, 0 to 25% ethyl acetate in hexanes, 40 CV) to afford product methyl 4-(5-(2-((1R,5S,7aS)-1-(3,5-bis(trifluoromethyl)phenyl)-3-oxohexahydro-1H-pyrrolo[1, 2-c]imidazol-5-yl)-4-(trifluoromethyl)phenyl)-6-methoxypyridin-3-yl)-3-methylbenzoate. LC-MS (ESI): [M+H]$^+$ for $C_{36}H_{28}F_9N_3O_4$: cald 738.2 found 738.2.

Step 2:

A 20 ml sample vial was charged with methyl 4-(5-(2-((1R,5S,7aS)-1-(3,5-bis(trifluoromethyl)phenyl)-3-oxohexahydro-1H-pyrrolo[1,2-c]imidazol-5-yl)-4-(trifluoromethyl)phenyl)-6-methoxypyridin-3-yl)-3-methylbenzoate (28 mg, 0.038 mmol) along with THF (0.5 ml), MeOH (0.500 ml), and water (0.1 ml), followed by addition of lithium hydroxide monohydrate (12 mg, 0.286 mmol). The mixture was then stirred at room temperature for 15 hrs overnight. The mixture was neutralized with HCl (1N, 0.286 mL) and concentrated. The product was purified by reverse phase HPLC using a column supplied by YMC (40-80% acetonitrile in water with 0.5% TFA) to afford 4-(5-(2-((1R, 5S,7aS)-1-(3,5-bis(trifluoromethyl)phenyl)-3-oxohexahydro-1H-pyrrolo[1,2-c]imidazol-5-yl)-4-(trifluoromethyl) phenyl)-6-methoxypyridin-3-yl)-3-methylbenzoic acid. LC-MS (ESI): [M+H]$^+$ for $C_{35}H_{24}F_9N_3O_4$: cald 724.2 found 724.1. RTA (95% HS): 335 nM.

Example 2

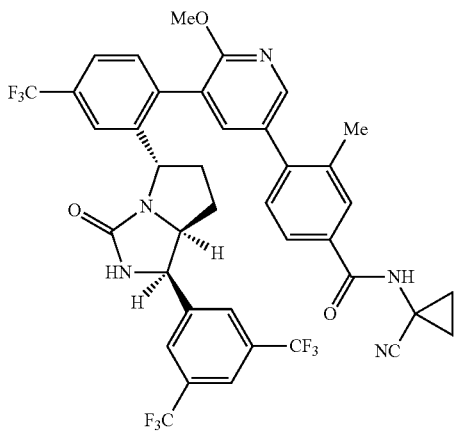 [SMILES: COc1ncc(-c2ccc(C(=O)NC3(C#N)CC3)cc2C)cc1-c1ccc(C(F)(F)F)cc1[C@@H]1CC[C@H]2[C@@H](c3cc(C(F)(F)F)cc(C(F)(F)F)c3)NC(=O)N12]

4-{5-[2-{(1R,5S,7aS)-1-[3,5-bis(trifluoromethyl) phenyl]-3-oxohexahydro-1H-pyrrolo[1,2-c]imidazol-5-yl}-4-(trifluoromethyl)phenyl]-6-methoxypyridin-3-yl}-N-(1-cyanocyclopropyl)-3-methylbenzamide Step 1:

1-Cyano-2-ethoxy-2-oxoethylidenaminooxy)dimethylamino-morpholino-carbenium hexafluorophosphate (COMU coupling reagent, 19.72 mg, 0.046 mmol) was added to a solution of 4-(5-(2-((1R,5S,7aS)-1-(3,5-bis(trifluoromethyl)phenyl)-3-oxohexahydro-1H-pyrrolo[1,2-c] imidazol-5-yl)-4-(trifluoromethyl)phenyl)-6-methoxypyridin-3-yl)-3-methylbenzoic acid (33.4 mg, 0.046 mmol), 1-aminocyclopropanecarbonitrile hydrochloride (5.47 mg, 0.046 mmol) and DIEA (0.024 ml, 0.138 mmol) in DMF (1.0 ml). The resulting mixture was stirred for 2 hrs at 40° C. The mixture was filtered through a syringe filter and purified by RP HPLC (column from YMC, 25 to 75% acetonitrile in water with 0.05% TFA) to afford a TFA salt of the product: 4-{5-[2-{(1R,5S,7aS)-1-[3,5-bis(trifluoromethyl)phenyl]-3-oxohexahydro-1H-pyrrolo[1,2-c]imidazol-5-yl}-4-(trifluoromethyl)phenyl]-6-methoxypyridin-3-yl}-N-(1-cyanocyclopropyl)-3-methylbenzamide. LC-MS ESI calc'd. for $C_{39}H_{30}F_9N_5O_3$ [M+H]+ 788.2. found 788.2. RTA (95% HS): 276 nM.

Example 3

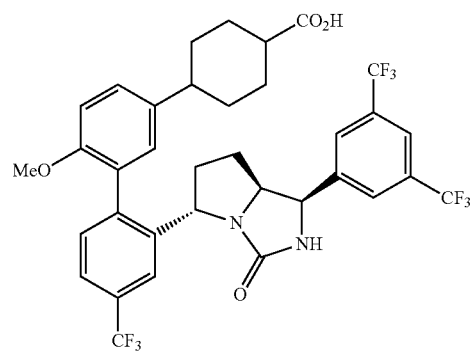

4-(2'-((1R,5 S,7aS)-1-(3,5-bis(trifluoromethyl)phenyl)-3-oxohexahydro-1H-pyrrolo[1,2-c]imidazol-5-yl)-6-methoxy-4'-(trifluoromethyl)-[1,1'-biphenyl]-3-yl)cyclohexanecarboxylic acid Step 1:

To a solution of (1R,5S,7aS)-1-(3,5-bis(trifluoromethyl) phenyl)-5-(2-chloro-5-(trifluoromethyl)phenyl)tetrahydro-1H-pyrrolo[1,2-c]imidazol-3(2H)-one (50 mg, 0.097 mmol) in THF (5 mL) and water (1 mL) were added methyl 4-(4-methoxy-3-(4,4,5,5-tetramethyl-1,3,2-dioxaborolan-2-yl)phenyl)cyclohexanecarboxylate (54 mg, 0.15 mmol) and $K_3PO_4$ (45 mg, 0.21 mmol), and the reaction was deoxygenated by alternately evacuating and purging with argon for 10 min. X-phos precatalyst (4 mg, 0.005 mmol) was added and the reaction was again deoxygenated for 5 min. The reaction flask was sealed and the mixture was heated at 60° C. for 3 h. The reaction was then diluted with EtOAc, rinsed with water, dried over anhydrous $Na_2SO_4$ and concentrated. The crude product was purified by Isolera (15% EtOAc/petroleum ether) to yield methyl 4-(2'-((1R,5S,7aS)-1-(3,5- bis(trifluoromethyl)phenyl)-3-oxohexahydro-1H-pyrrolo[1,2-c]imidazol-5-yl)-6-methoxy-4'-(trifluoromethyl)-[1,1'-biphenyl]-3-yl)cyclohexanecarboxylate. LC-MS ESI calc'd. for $C_{36}H_{33}F_9N_2O_4$ [M+H]+ 729.2. found 729.2.

Step 2:

To a solution of methyl 4-(2'-((1R,5S,7aS)-1-(3,5-bis(trifluoromethyl)phenyl)-3-oxohexahydro-1H-pyrrolo[1,2-c]imidazol-5-yl)-6-methoxy-4'-(trifluoromethyl)-[1,1'-biphenyl]-3-yl)cyclohexanecarboxylate (55 mg, 0.07 mmol) in THF/MeOH/H₂O (3.5 mL), was added LiOH.H₂O (10 mg, 0.23 mmol) and the reaction was stirred at rt for 18 h. The crude reaction product was acidified by the addition of citric acid and extracted with MTBE. The organic layer was dried over anhydrous Na₂SO₄ and concentrated to yield 4-(2'-((1R,5S,7aS)-1-(3,5-bis(trifluoromethyl)phenyl)-3-oxohexahydro-1H-pyrrolo[1,2-c]imidazol-5-yl)-6-methoxy-4'-(trifluoromethyl)-[1,1'-biphenyl]-3-yl)cyclohexanecarboxylic acid. ¹H NMR (400 MHz, CDCl₃) δ 7.86 (s, 1H), 7.78 (s, 2H), 7.70 (s, 2H), 7.53-7.55 (m, 1H), 7.30-7.32 (m, 2H), 7.21-7.24 (dd, 1H, J=8, 2 Hz), 6.90 (d, 1H, J=8 Hz), 5.38 (d, 1H, J=9 Hz), 4.84-4.89 (dd, 1H, J=9, 7 Hz), 4.55-4.59 (m, 1H), 3.70 (s, 3H), 2.61 (m, 1H), 2.45-2.56 (m, 1H), 2.26 (m, 1H), 2.01-2.25 (m, 4H), 1.55-1.69 (m, 4H), 1.23-1.33 (m, 1H), 1.04 (m, 1H), 0.95 (m, 1H); LC-MS ESI calc'd. for $C_{35}H_{31}F_9N_2O_4$ [M+H]+ 715.2. found 715.2. RTA (95% HS): 1727 nM.

The following examples in Table 1 were prepared according to methods outlined above:

| Example | Structure | IUPAC Name | Exact Mass [M + H]⁺ or [M − H]⁻ | IC₅₀ (nM) |
|---|---|---|---|---|
| Example 4 | 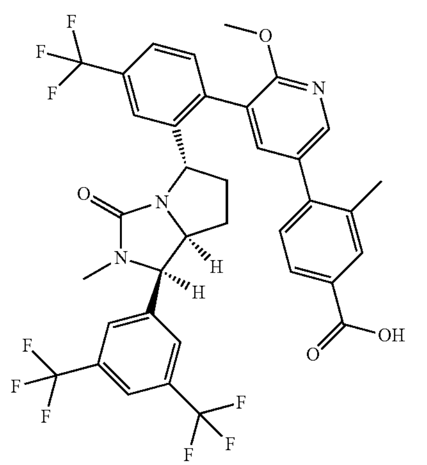 [SMILES: COc1ncc(-c2ccc(C(=O)O)cc2C)cc1-c1ccc(C(F)(F)F)cc1[C@@H]1CC[C@H]2[C@@H](c3cc(C(F)(F)F)cc(C(F)(F)F)c3)N(C)C(=O)N12] | 4-{5-[2-{(1R,5S,7aS)-1-[3,5-bis(trifluoromethyl)phenyl]-2-methyl-3-oxohexahydro-1H-pyrrolo[1,2-c]imidazol-5-yl}-4-(trifluoromethyl)phenyl]-6-methoxypyridin-3-yl}-3-methylbenzoic acid | Calcd: 738.2 Found: 738.2 | 1500 |
| Example 5 | 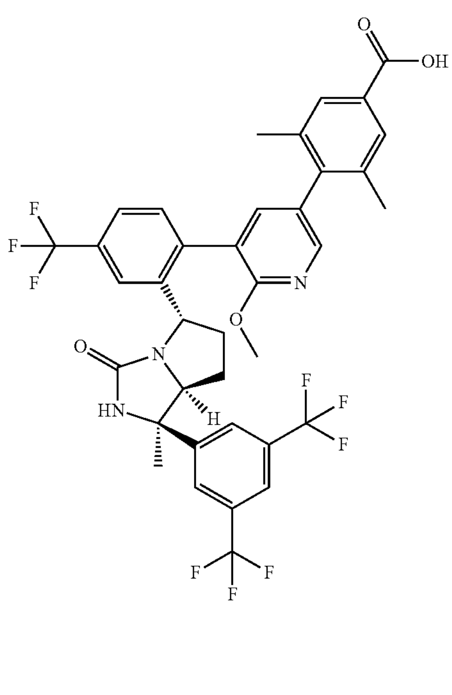 [SMILES: COc1ncc(-c2c(C)cc(C(=O)O)cc2C)cc1-c1ccc(C(F)(F)F)cc1[C@@H]1CC[C@@H]2N1C(=O)N[C@]2(C)c1cc(C(F)(F)F)cc(C(F)(F)F)c1] | 4-{5-[2-{(1R,5S,7aS)-1-[3,5-bis(trifluoromethyl)phenyl]-3-oxohexahydro-1H-pyrrolo[1,2-c]imidazol-5-yl}-4-(trifluoromethyl)phenyl]-6-methoxypyridin-3-yl}-3,5-dimethylbenzoic acid | Calcd: 738.2 Found: 738.2 | 392 |

-continued

| Example | Structure | IUPAC Name | Exact Mass [M + H]+ or [M − H]− | IC$_{50}$ (nM) |
|---|---|---|---|---|
| Example 6 | 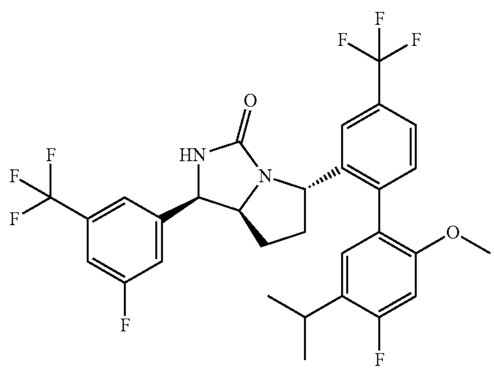 [SMILES: COc1cc(F)c(C(C)C)cc1-c1ccc(C(F)(F)F)cc1[C@@H]1CC[C@H]2[C@@H](c3cc(F)cc(C(F)(F)F)c3)NC(=O)N12] | (1R,5S,7aS-5-[4'-fluoro-2'-methoxy-5'-(1-methylethyl)-4-(trifluoromethyl)biphenyl-2-yl]-1-[3-fluoro-5-(trifluoromethyl)phenyl]hexahydro-3H-pyrrolo[1,2-c]imidazol-3-one | Calcd: 599.2 Found: 599.2 | 1067 |
| Example 7 | 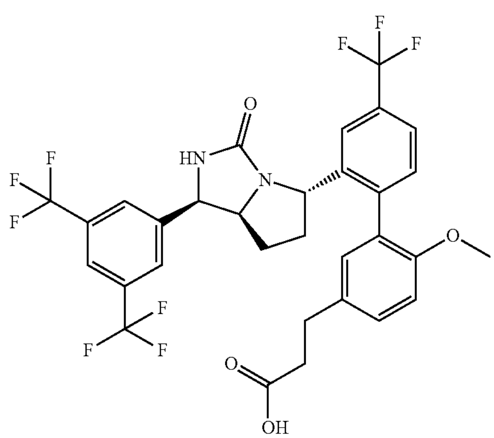 [SMILES: COc1ccc(CCC(=O)O)cc1-c1ccc(C(F)(F)F)cc1[C@@H]1CC[C@H]2[C@@H](c3cc(C(F)(F)F)cc(C(F)(F)F)c3)NC(=O)N12] | 3-[2'-{(1R,5S,7aS)-1-[3,5-bis(trifluoromethyl)phenyl]-3-oxohexahydro-1H-pyrrolo[1,2-c]imidazol-5-yl}-6-methoxy-4'-(trifluoromethyl)biphenyl-3-yl]propanoic acid | Calcd: 661.2 Found: 661.2 | 1200 |
| Example 8 | 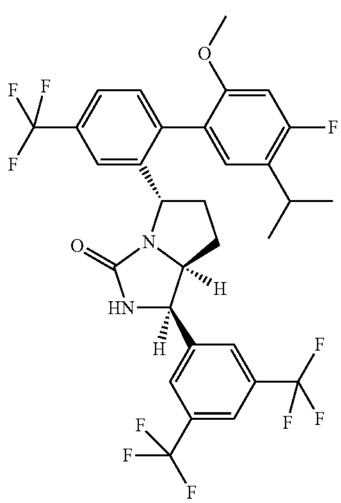 [SMILES: COc1cc(F)c(C(C)C)cc1-c1ccc(C(F)(F)F)cc1[C@@H]1CC[C@H]2[C@@H](c3cc(C(F)(F)F)cc(C(F)(F)F)c3)NC(=O)N12] | (1R,5S,7aS)-1-[3,5-bis(trifluoromethyl)phenyl]-5-[4'-fluoro-2'-methoxy-5'-(1-methylethyl)-4-(trifluoromethyl)biphenyl-2-yl]hexahydro-3H-pyrrolo[1,2-c]imidazol-3-one | Calcd: 649.2 Found: 649.2 | 701 |

-continued

| Example | Structure | IUPAC Name | Exact Mass [M + H]+ or [M − H]− | IC50 (nM) |
|---|---|---|---|---|
| Example 9 | 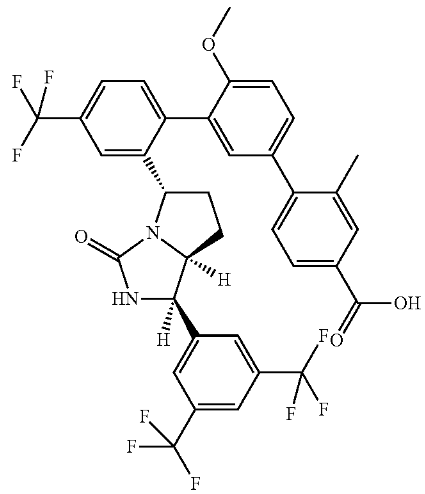 [SMILES: COc1ccc(-c2ccc(C(=O)O)cc2C)cc1-c1ccc(C(F)(F)F)cc1[C@@H]1CC[C@H]2[C@@H](c3cc(C(F)(F)F)cc(C(F)(F)F)c3)NC(=O)N12] | 2''-(1R,5S,7aS)-1-[3,5-bis(trifluoromethyl)phenyl]-3-oxohexahydro-1H-pyrrolo[1,2-c]imidazol-5-yl}-4'-methoxy-2-methyl-4''-(trifluoromethyl)-1,1':3',1''-terphenyl-4-carboxylic acid | Calcd: 721.2 Found: 721.0 | 1362 |
| Example 10 | 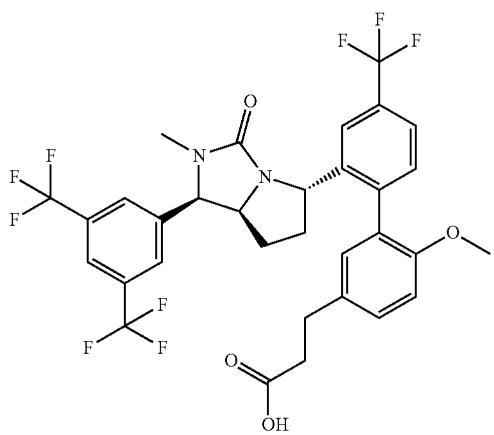 [SMILES: COc1ccc(CCC(=O)O)cc1-c1ccc(C(F)(F)F)cc1[C@@H]1CC[C@H]2[C@@H](c3cc(C(F)(F)F)cc(C(F)(F)F)c3)N(C)C(=O)N12] | 3-[2'-{(1R,5S,7aS)-1-[3,5-bis(trifluoromethyl)phenyl]-2-methyl-3-oxohexahydro-1H-pyrrolo[1,2-c]imidazol-5-yl}-6-methoxy-4'-(trifluoromethyl)biphenyl-3-yl]propanoic acid | Calcd: 675.2 Found: 675.2 | 2947 |
| Example 11 | 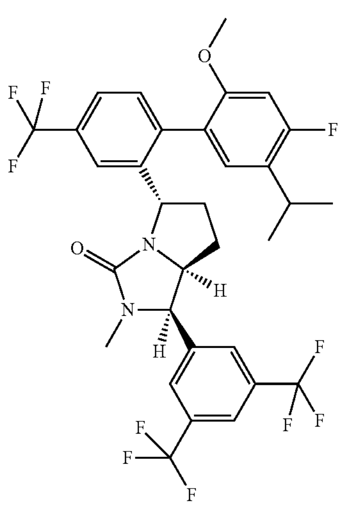 [SMILES: COc1cc(F)c(C(C)C)cc1-c1ccc(C(F)(F)F)cc1[C@@H]1CC[C@H]2[C@@H](c3cc(C(F)(F)F)cc(C(F)(F)F)c3)N(C)C(=O)N12] | (1R,5S,7aS)-1-[3,5-bis(trifluoromethyl)phenyl]-5-[4'-fluoro-2'-methoxy-5'-(1-methylethyl)-4-(trifluoromethyl)biphenyl-2-yl]-2-methylhexahydro-3H-pyrrolo[1,2-c]imidazol-3-one | Calcd: 663.2 Found: 663.2 | 2297 |

| Example | Structure | IUPAC Name | Exact Mass [M + H]+ or [M − H]− | IC50 (nM) |
|---|---|---|---|---|
| Example 12 | 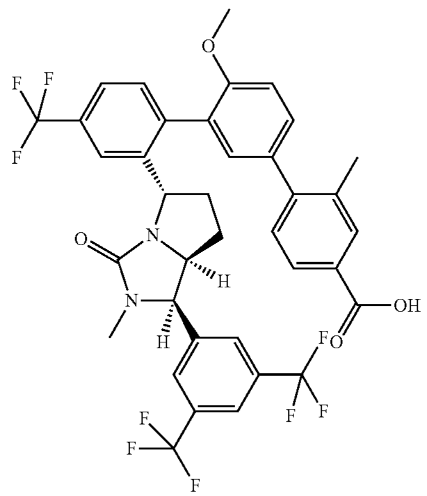 [SMILES: COc1ccc(-c2ccc(C(=O)O)cc2C)cc1-c1ccc(C(F)(F)F)cc1[C@@H]1CC[C@H]2[C@@H](c3cc(C(F)(F)F)cc(C(F)(F)F)c3)N(C)C(=O)N12] | 2''-{(1R,5S,7aS)-1-[3,5-bis(trifluoromethyl)phenyl]-2-methyl-3-oxohexahydro-1H-pyrrolo[1,2-c]imidazol-5-yl]-4'-methoxy-2-methyl-4''-(trifluoromethyl)-1,1':3',1''-terphenyl-4-carboxylic acid | Calcd: 737.2<br>Found: 737.2 | 1419 |
| Example 13 | 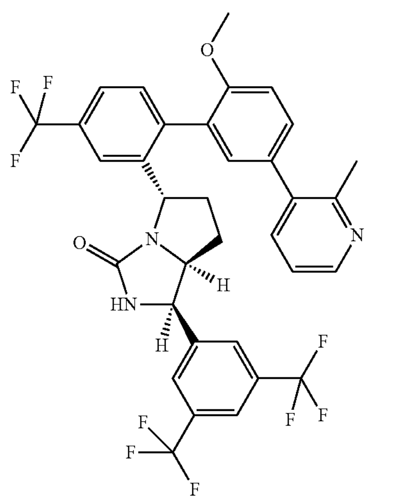 [SMILES: COc1ccc(-c2cccnc2C)cc1-c1ccc(C(F)(F)F)cc1[C@@H]1CC[C@H]2[C@@H](c3cc(C(F)(F)F)cc(C(F)(F)F)c3)NC(=O)N12] | (1R,5S,7aS)-1-[3,5-bis(trifluoromethyl)phenyl]-5-[2'-methoxy-5'-(2-methylpyridin-3-yl)-4-(trifluoromethyl)biphenyl-2-yl]hexahydro-3H-pyrrolo[1,2-c]imidazol-3-one | Calcd: 680.2<br>Found: 680.2 | 795 |
| Example 14 | 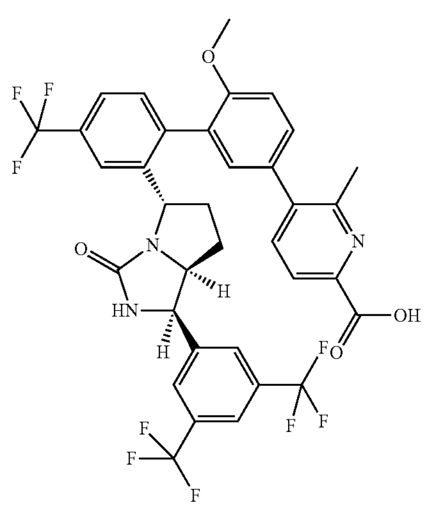 [SMILES: COc1ccc(-c2ccc(C(=O)O)nc2C)cc1-c1ccc(C(F)(F)F)cc1[C@@H]1CC[C@H]2[C@@H](c3cc(C(F)(F)F)cc(C(F)(F)F)c3)NC(=O)N12] | 5-[2'-{(1R,5S,7aS)-1-[3,5-bis(trifluoromethyl)phenyl]-3-oxohexahydro-1H-pyrrolo[1,2-c]imidazol-5-yl}-methoxy-4'-(trifluoromethyl)biphenyl-3-yl]-6-methylpyridine-2-carboxylic acid | Calcd: 724.2<br>Found: 724.0 | 1934 |

| Example | Structure | IUPAC Name | Exact Mass [M + H]+ or [M − H]− | IC$_{50}$ (nM) |
|---|---|---|---|---|
| Example 15 | 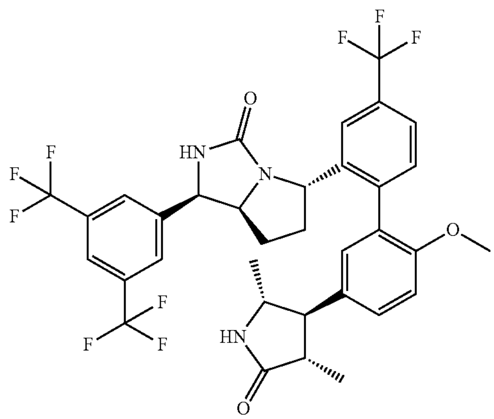 [SMILES: COc1ccc([C@H]2[C@H](C)C(=O)N[C@@H]2C)cc1-c1ccc(C(F)(F)F)cc1[C@@H]1CC[C@H]2[C@@H](c3cc(C(F)(F)F)cc(C(F)(F)F)c3)NC(=O)N12] | (1R,5S,7aS)-1-[3,5-bis(trifluoromethyl)phenyl]-5-{5'-[(2R,3R,4S)-2,4-dimethyl-5-oxopyrrolidin-3-yl]-2'-methoxy-4-(trifluoromethyl)biphenyl-2-yl}hexahydro-3H-pyrrolo[1,2-c]imidazol-3-one | Calcd: 700.2 Found: 700.2 | 1737 |
| Example 16 | 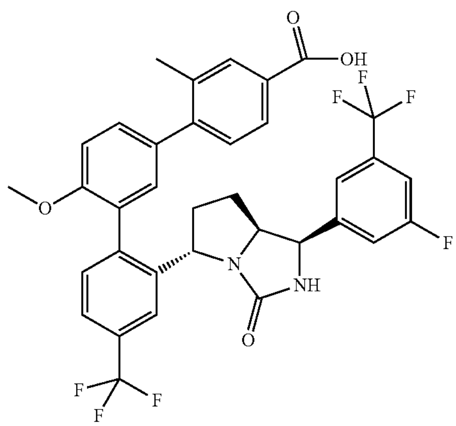 [SMILES: COc1ccc(-c2ccc(C(=O)O)cc2C)cc1-c1ccc(C(F)(F)F)cc1[C@@H]1CC[C@H]2[C@@H](c3cc(F)cc(C(F)(F)F)c3)NC(=O)N12] | 2''-{(1R,5S,7aS)-1-[3-fluoro-5-(trifluoromethyl)phenyl]-3-oxohexahydro-1H-pyrrolo[1,2-c]imidazol-5-yl}-4'-methoxy-2-methyl-4''-(trifluoromethyl)-1,1':3',1''-terphenyl-4-carboxylic acid | Calcd: 673.2 Found: 673.2 | 1507 |
| Example 17 | 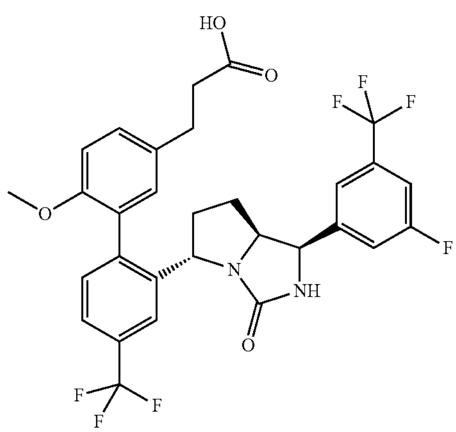 [SMILES: COc1ccc(CCC(=O)O)cc1-c1ccc(C(F)(F)F)cc1[C@@H]1CC[C@H]2[C@@H](c3cc(F)cc(C(F)(F)F)c3)NC(=O)N12] | 3-[2'-{(1R,5S,7aS)-1-[3-fluoro-5-(trifluoromethyl)phenyl]-3-oxohexahydro-1H-pyrrolo[1,2-c]imidazol-5-yl}-6-methoxy-4'-(trifluoromethyl)biphenyl-3-yl]propanoic acid | Calcd: 611.2 Found: 611.2 | 3159 |

-continued

| Example | Structure | IUPAC Name | Exact Mass [M + H]+ or [M − H]− | IC50 (nM) |
|---------|-----------|------------|-------------------------------|-----------|
| Example 18 | 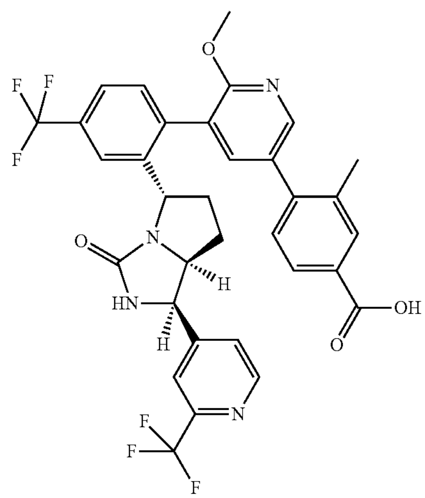 [SMILES: COc1ncc(-c2ccc(C(=O)O)cc2C)cc1-c1ccc(C(F)(F)F)cc1[C@@H]1CC[C@H]2[C@@H](c3ccnc(C(F)(F)F)c3)NC(=O)N12] | 4-{6-methoxy-5-[2-{(1R,5S,7aS)-3-oxo-1-[2-(trifluoromethyl)pyridin-4-yl]hexahydro-1H-pyrrolo[1,2-c]imidazol-5-yl}-4-(trifluoromethyl)phenyl]pyridin-3-yl}-3-methylbenzoic acid | Calcd: 657.2 Found: 657.2 | 5040 |
| Example 19 | 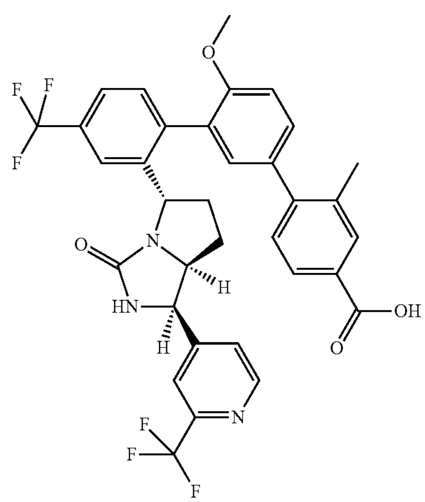 [SMILES: COc1ccc(-c2ccc(C(=O)O)cc2C)cc1-c1ccc(C(F)(F)F)cc1[C@@H]1CC[C@H]2[C@@H](c3ccnc(C(F)(F)F)c3)NC(=O)N12] | 4'-methoxy-2-methyl-2''-{(1R,5S,7aS)-3-oxo-1-[2-(trifluoromethyl)pyridin-4-yl]hexahydro-1H-pyrrolo[1,2-c]imidazol-5-yl}-4''-(trifluoromethyl)-1,1':3',1''-terphenyl-4-carboxylic acid | Calcd: 656.2 Found: 656.2 | 4871 |
| Example 20 | 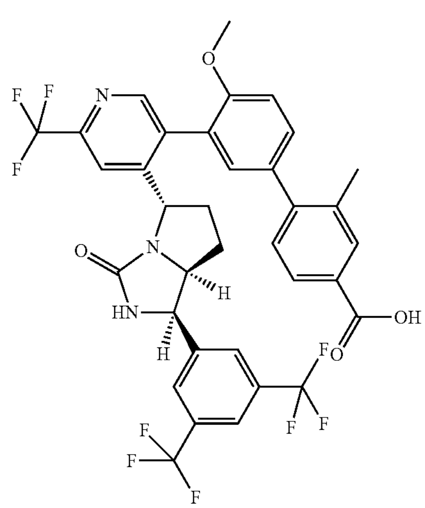 [SMILES: COc1ccc(-c2ccc(C(=O)O)cc2C)cc1-c1cnc(C(F)(F)F)cc1[C@@H]1CC[C@H]2[C@@H](c3cc(C(F)(F)F)cc(C(F)(F)F)c3)NC(=O)N12] | 3'-[4-{(1R,5S,7aS)-1-[3,5-bis(trifluoromethyl)phenyl]-3-oxohexahydro-1H-pyrrolo[1,2-c]imidazol-5-yl}-6-(trifluoromethyl)pyridin-3-yl]-4'-methoxy-2-methylbiphenyl-4-carboxylic acid | Calcd: 724.2 Found: 724.2 | 1570 |

-continued

| Example | Structure | IUPAC Name | Exact Mass [M + H]+ or [M − H]− | IC50 (nM) |
|---|---|---|---|---|
| Example 21 | 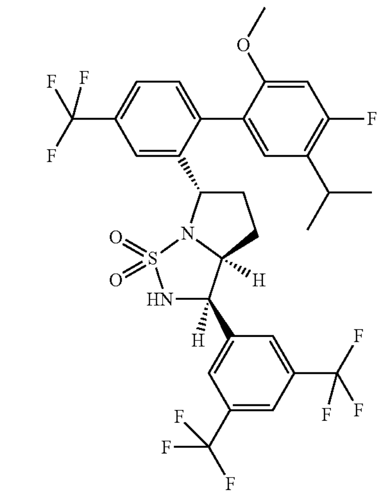 [SMILES: COc1cc(F)c(C(C)C)cc1-c1ccc(C(F)(F)F)cc1[C@@H]1CC[C@H]2[C@@H](c3cc(C(F)(F)F)cc(C(F)(F)F)c3)NS(=O)(=O)N12] | (3R,3aS,6S)-3-[3,5-bis(trifluoromethyl)phenyl]-6-[4'-fluoro-2'-methoxy-5'-(1-methylethyl)-4-(trifluoromethyl)biphenyl-2-yl]hexahydropyrrolo[1,2-b][1,2,5]thiadiazole 1,1-dioxide | Calc'd: 685.2, Found: 685.2 | 479 |
| Example 22 | 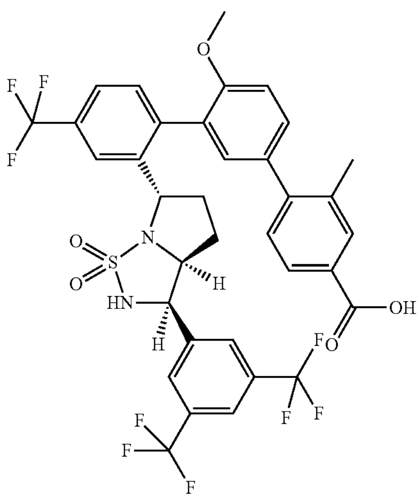 [SMILES: COc1ccc(-c2ccc(C(=O)O)cc2C)cc1-c1ccc(C(F)(F)F)cc1[C@@H]1CC[C@H]2[C@@H](c3cc(C(F)(F)F)cc(C(F)(F)F)c3)NS(=O)(=O)N12] | 2''-{(3R,3aS,6S)-3-[3,5-bis(trifluoromethyl)phenyl]-1,1-dioxidohexahydropyrrolo[1,2-b][1,2,5]thiadiazol-6-yl}-4'-methoxy-2-methyl-4''-(trifluoromethyl)-1,1';3',1''-terphenyl-4-carboxylic acid | [M − H]− Calc'd: 757.2, Found: 757.0 | 984 |
| Example 23 | 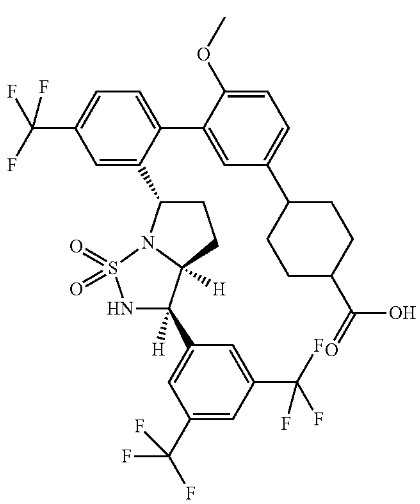 [SMILES: COc1ccc(C2CCC(C(=O)O)CC2)cc1-c1ccc(C(F)(F)F)cc1[C@@H]1CC[C@H]2[C@@H](c3cc(C(F)(F)F)cc(C(F)(F)F)c3)NS(=O)(=O)N12] | 4-[2'-{(3R,3aS,6S)-3-[3,5-bis(trifluoromethyl)phenyl]-1,1-dioxidohexahydropyrrolo[1,2-b][1,2,5]thiadiazol-6-yl}-6-methoxy-4'-(trifluoromethyl)biphenyl-3-yl]cyclohexanecarboxylic acid | [M − H]− Calc'd: 749.2, Found: 749.2 | 268 |

| Example | Structure | IUPAC Name | Exact Mass [M + H]+ or [M − H]− | IC50 (nM) |
|---|---|---|---|---|
| Example 24 | 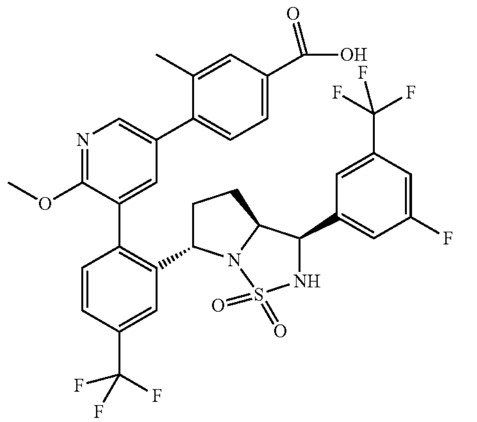 [SMILES: COc1ncc(-c2ccc(C(=O)O)cc2C)cc1-c1ccc(C(F)(F)F)cc1[C@@H]1CC[C@H]2[C@@H](c3cc(F)cc(C(F)(F)F)c3)NS(=O)(=O)N12] | 4-{5-[2-{(3R,3aS,6S)-3-[3-fluoro-5-(trifluoromethyl)phenyl]-1,1-dioxidohexahydropyrrolo[1,2-b][1,2,5]thiadiazol-6-yl}-4-(trifluoromethyl)phenyl]-6-methoxypyridin-3-yl}-3-methylbenzoic acid | [M − H]− Calc'd: 708.2, Found: 708.2 | 1258 |
| Example 25 | 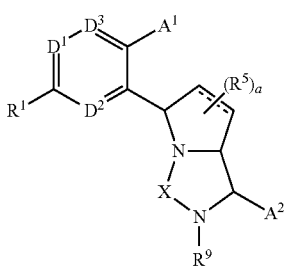 | 3-[2'-{(3R,3aS,6S)-3-[3-fluoro-5-(trifluoromethyl)phenyl]-1,1-dioxidohexahydropyrrolo[1,2-b][1,2,5]thiadiazol-6-yl}-6-methoxy-4'-(trifluoromethyl)biphenyl-3-yl]propanoic acid | Calc'd: 647.1, Found: 647.2 | 3117 |

What is claimed is:

1. A compound of Formula I, or a pharmaceutically acceptable salt thereof:

I wherein X is —C(=O), $R^1$ is H, —$C_1$-$C_5$ alkyl, —O$C_1$-$C_5$ alkyl, —$C_2$-$C_5$ alkenyl, —O$C_2$-$C_5$ alkenyl, —$C_2$-$C_5$ alkynyl, —O$C_2$-$C_5$ alkynyl, —OH, halogen, —CN, —N$R^6R^7$, —$CO_2R^8$, —C(O)N$R^6R^7$, —$SO_2$N$R^6R^7$, HET(3), or $C_{3-6}$ cycloalkyl optionally having 1-2 double bonds, wherein —$C_1$-$C_5$ alkyl, —O$C_1$-$C_5$ alkyl, —$C_2$-$C_5$ alkenyl, —O$C_2$-$C_5$ alkenyl, —$C_2$-$C_5$ alkynyl, and —O$C_2$-$C_5$ alkynyl are each optionally substituted with 1-7 halogens, and wherein HET(3) and $C_{3-6}$ cycloalkyl optionally having 1-2 double bonds are optionally substituted with 1-3 substituent groups which are each independently halogen, —$C_1$-$C_3$ alkyl, —O$C_1$-$C_3$ alkyl, —$C_2$-$C_3$ alkenyl, —O$C_2$-$C_3$ alkenyl, —$C_2$-$C_3$ alkynyl, or —O$C_2$-$C_3$ alkynyl, wherein —$C_1$-$C_3$ alkyl, —O$C_1$-$C_3$ alkyl, —$C_2$-$C_3$ alkenyl, —O$C_2$-$C_3$ alkenyl, —$C_2$-$C_3$alkynyl, and —O$C_2$-$C_3$ alkynyl are each optionally substituted with 1-7 halogens;

$R^6$ and $R^7$ are each independently H, —$C_1$-$C_5$ alkyl, phenyl, naphthyl, $C_{3-6}$ cycloalkyl optionally having 1-2 double bonds, or HET(3), wherein phenyl, naphthyl, $C_{3-6}$ cycloalkyl, and HET(3) are optionally substituted with 1-3 substituent groups which are each independently halogen, —$C_1$-$C_3$ alkyl, —O$C_1$-$C_3$ alkyl, —$C_2$-$C_3$ alkenyl, —O$C_2$-$C_3$ alkenyl, —$C_2$-$C_3$ alkynyl, or —O$C_2$-$C_3$ alkynyl, wherein —$C_1$-$C_3$ alkyl, —O$C_1$-$C_3$ alkyl, —$C_2$-$C_3$ alkenyl, —O$C_2$-$C_3$ alkenyl, —$C_2$-$C_3$alkynyl, and —O$C_2$-$C_3$ alkynyl are each optionally substituted with 1-7 halogens;

$R^8$ is H or —$C_{1-5}$alkyl optionally substituted with 1-7 halogens;

$R^9$ is H or —$C_{1-5}$alkyl optionally substituted with 1-7 halogens;

HET(3) is a 3-6 membered heterocyclic ring having 1-3 heteroatom groups which are each independently N, NH, O, S, S(O), or S(O)$_2$ and optionally having 1-3 double bonds;

The dashed line in Formula I represents an optional double bond;

$D^1$ is $CR^2$;

$D^2$ is $CR^3$;

$D^3$ is $CR^4$;

$R^2$, $R^3$, and $R^4$ are each independently H, —$C_1$-$C_5$ alkyl, —$OC_1$-$C_5$ alkyl, —$C_2$-$C_5$ alkenyl, —$OC_2$-$C_5$ alkenyl, —$C_2$-$C_5$ alkynyl, —$OC_2$-$C_5$ alkynyl, —OH, halogen, —CN, —$NR^6R^7$, —$CO_2R^8$, —$C(O)NR^6R^7$, or —$SO_2NR^6R^7$, wherein —$C_1$-$C_5$ alkyl, —$OC_1$-$C_5$ alkyl, —$C_2$-$C_5$ alkenyl, —$OC_2$-$C_5$ alkenyl, —$C_2$-$C_5$ alkynyl, and —$OC_2$-$C_5$ alkynyl are optionally substituted with 1-7 halogens;

Each $R^5$ is independently —$C_1$-$C_5$ alkyl, —$OC_1$-$C_5$ alkyl, —$C_2$-$C_5$ alkenyl, —$OC_2$-$C_5$ alkenyl, —$C_2$-$C_5$ alkynyl, —$OC_2$-$C_5$ alkynyl, —OH, halogen, —CN, —$NR^6R^7$, —$CO_2R^8$, —$C(O)NR^6R^7$, or —$SO_2NR^6R^7$, wherein —$C_1$-$C_5$ alkyl, —$OC_1$-$C_5$ alkyl, —$C_2$-$C_5$ alkenyl, —$OC_2$-$C_5$ alkenyl, —$C_2$-$C_5$ alkynyl, and —$OC_2$-$C_5$ alkynyl are optionally substituted with 1-7 halogens;

$A^1$ is phenyl, HET(1), or $C_3$-$C_8$ cycloalkyl optionally having 1-2 double bonds, wherein $A^1$ is optionally substituted with one substituent group Z and is optionally substituted with 1-3 groups which are each independently —$C_1$-$C_5$ alkyl, —$OC_1$-$C_5$ alkyl, —$C_2$-$C_5$ alkenyl, —$OC_2$-$C_5$ alkenyl, —$C_2$-$C_5$ alkynyl, —$OC_2$-$C_5$ alkynyl, halogen, —OH, or —CN, wherein —$C_1$-$C_5$ alkyl, —$OC_1$-$C_5$ alkyl, —$C_2$-$C_5$ alkenyl, —$OC_2$-$C_5$ alkenyl, —$C_2$-$C_5$ alkynyl, and —$OC_2$-$C_5$ alkynyl are optionally substituted with 1-7 halogens;

HET(1) is a 5- or 6-membered heterocyclic ring having 1-4 heteroatom groups which are each independently —N—, —NH—, —S—, —O—, —S(O)—, or —S(O)$_2$—, optionally having one group —C(=O)—, and optionally having 1-3 double bonds;

Z is $A^3$, —$C_1$-$C_3$alkylene-$CO_2R^8$, —$C_1$-$C_3$alkylene-$C(O)NR^6R^7$, —$C_1$-$C_3$alkylene-$SO_2NR^6R^7$, —$CO_2R^8$, —$C(O)NR^6R^7$, —$SO_2NR^6R^7$, or —$C_1$-$C_3$alkylene-HET(2), wherein —$C_1$-$C_3$alkylene in all uses is optionally substituted with 1-7 halogens, and HET(2) is optionally substituted with 1-3 substituents which are independently —$C_{1-3}$alkyl optionally substituted with 1-5 halogens, —$OC_{1-3}$alkyl optionally substituted with 1-5 halogens, halogen or $NR^6R^7$;

$A^3$ is phenyl, $C_3$-$C_6$ cycloalkyl optionally having 1-2 double bonds, or HET(1), wherein $A^3$ is optionally substituted with 1-3 groups which are each independently —$C_1$-$C_5$ alkyl, —$OC_1$-$C_5$ alkyl, —$C_2$-$C_5$ alkenyl, —$OC_2$-$C_5$ alkenyl, —$C_2$-$C_5$ alkynyl, —$OC_2$-$C_5$ alkynyl, halogen, —OH, or —CN, wherein —$C_1$-$C_5$ alkyl, —$OC_1$-$C_5$ alkyl, —$C_2$-$C_5$ alkenyl, —$OC_2$-$C_5$ alkenyl, —$C_2$-$C_5$ alkynyl, and —$OC_2$-$C_5$ alkynyl are optionally substituted with 1-7 halogens; and $A^3$ is optionally substituted with one group which is HET(2), —$C_{1-4}$ alkylene-$CO_2R^8$, —$C_{1-4}$alkylene-$C(O)NR^6R^7$, —$C_1$-$C_4$alkylene-$SO_2NR^6R^7$, —$CO_2R^8$, —$C(O)NR^6R^7$, —$SO_2NR^6R^7$, or —$C(O)NR^6C_{3-6}$cycloalkyl in which $C_{3-6}$ cycloalkyl is optionally substituted with 1-3 substituents which are independently selected from halogen, $C_{1-2}$alkyl, and —CN, wherein —$C_1$-$C_4$alkylene in all uses is optionally substituted with 1-7 halogens; and wherein HET(2) is optionally substituted with 1-3 groups which are each independently halogen, —$C_{1-5}$alkyl optionally substituted with 1-7 halogens, —$OC_{1-5}$alkyl optionally substituted with 1-7 halogens, or $NR^6R^7$;

HET(2) is a 5-6 membered heterocyclic ring having 1-3 heteroatom groups which are each independently N, NH, O, or S, optionally having one group —C(=O)—, and optionally having 1-3 double bonds;

$A^2$ is phenyl or HET(1), wherein $A^2$ is optionally substituted with 1-3 substituent groups which are each independently —$C_1$-$C_5$ alkyl, —$OC_1$-$C_5$ alkyl, —$C_2$-$C_5$ alkenyl, —$OC_2$-$C_5$ alkenyl, —$C_2$-$C_5$alkynyl, —$OC_2$-$C_5$alkynyl, halogen, —CN, —OH, or $C_{3-6}$cycloalkyl, wherein —$C_1$-$C_5$ alkyl, —$OC_1$-$C_5$ alkyl, —$C_2$-$C_5$ alkenyl, —$OC_2$-$C_5$ alkenyl, —$C_2$-$C_5$alkynyl, and —$OC_2$-$C_5$ alkynyl are optionally substituted with 1-7 halogens, and $C_{3-6}$cycloalkyl is optionally substituted with 1-3 substituents which are each independently halogen, —$C_1$-$C_3$ alkyl, or —$OC_1$-$C_3$ alkyl, wherein —$C_1$-$C_3$ alkyl and —$OC_1$-$C_3$ alkyl are each optionally substituted with 1-7 halogens; and a is 0 or an integer from 1-3.

2. The compound of claim 1, or a pharmaceutically acceptable salt thereof:

wherein $R^1$ is —$C_1$-$C_5$ alkyl, —$OC_1$-$C_5$ alkyl, halogen, —$NR^6R^7$, HET(3), or $C_{3-6}$ cycloalkyl optionally having 1-2 double bonds, wherein —$C_1$-$C_5$ alkyl and —$OC_1$-$C_5$ alkyl are optionally substituted with 1-7 halogens, and wherein HET(3) and $C_{3-6}$ cycloalkyl optionally having 1-2 double bonds are optionally substituted with 1-3 substituent groups which are each independently halogen, $CH_3$, $CF_3$, $OCH_3$, or $OCF_3$;

$R^2$, $R^3$, and $R^4$ are each independently H, —$C_1$-$C_5$ alkyl, —$OC_1$-$C_5$ alkyl, or halogen, wherein —$C_1$-$C_5$ alkyl and —$OC_1$-$C_5$ alkyl are optionally substituted with 1-7 halogens;

Each $R^5$ is independently —$C_1$-$C_5$ alkyl, —$OC_1$-$C_5$ alkyl, or halogen, wherein —$C_1$-$C_5$ alkyl and —$OC_1$-$C_5$ alkyl are optionally substituted with 1-7 halogens;

$A^1$ is phenyl, HET(1), or $C_3$-$C_6$ cycloalkyl optionally having 1-2 double bonds, wherein $A^1$ is optionally substituted with one substituent group Z and is optionally substituted with 1-3 groups which are each independently halogen, —OH, —CN, —$C_{1-5}$alkyl optionally substituted with 1-7 halogens, or —$OC_{1-5}$alkyl optionally substituted with 1-7 halogens;

$A^3$ is phenyl, $C_3$-$C_6$ cycloalkyl optionally having 1-2 double bonds, or HET(1), wherein $A^3$ is optionally substituted with 1-3 groups which are each independently —$C_1$-$C_5$ alkyl optionally substituted with 1-7 halogens, —$OC_1$-$C_5$ alkyl optionally substituted with 1-7 halogens, —OH, or halogen, and is optionally substituted with one group which is HET(2), —$C_{1-2}$alkylene-$CO_2R^8$, —$C_{1-2}$alkylene-$C(O)NR^6R^7$, —$C_1$-$C_2$alkylene-$SO_2NR^6R^7$, —$CO_2R^8$, —$C(O)NR^6R^7$, —$SO_2NR^6R^7$, or —$C(O)NR^6C_{3-6}$cycloalkyl wherein $C_{3-6}$cycloalkyl is optionally substituted with 1-3 substituents which are independently selected from halogen, $C_{1-2}$alkyl, and —CN, wherein —$C_1$-$C_2$alkylene is optionally substituted with 1-3 halogens; and wherein HET(2) is optionally substituted with 1-3 groups which are each independently halogen, —$C_{1-5}$alkyl optionally substituted with 1-7 halogens, —$OC_{1-5}$alkyl optionally substituted with 1-7 halogens, or $NR^6R^7$; and $A^2$ is phenyl or HET(1), wherein $A^2$ is optionally substituted with 1-3 substituent groups which are each independently $C_{1-5}$alkyl optionally substituted with 1-7 halogens, —$OC_{1-5}$alkyl optionally substituted with 1-7 halogens, halogen, —OH, —CN, or $C_{3-6}$cycloalkyl optionally substituted with 1-3 substituents which are each independently halogen, $CF_3$, $CH_3$, $-OCF_3$, or $-OCH_3$.

3. The compound of claim 2, or a pharmaceutically acceptable salt thereof:
wherein X is $-C(=O)-$;
$R^1$ is $CH_3$, $CF_3$, $-OCH_3$, $-OCF_3$, halogen, or $-NR^6R^7$;
$R^6$ and $R^7$ are each independently H or $-C_1$-$C_5$ alkyl;
$R^2$, $R^3$, and $R^4$ are each independently H, $C_{1-3}$alkyl, $CF_3$, $-OC_{1-3}$alkyl, $-OCF_3$, or halogen;
Each $R^5$ is independently $CH_3$, $CF_3$, $-OCH_3$, $-OCF_3$, or halogen;
$A^1$ is phenyl, HET(1), or $C_3$-$C_6$ cycloalkyl optionally having 1-2 double bonds, wherein $A^1$ is optionally substituted with one substituent group Z and is optionally substituted with 1-3 groups which are each independently $-C_{1-3}$alkyl optionally substituted with 1-5 halogens, $-OC_{1-3}$alkyl optionally substituted with 1-5 halogens, halogen, $-OH$, or $-CN$;
Each HET(1) is a 5- or 6-membered heterocyclic ring having 1-3 heteroatom groups which are each independently $-N-$, $-NH-$, $-S-$, or $-O-$, optionally having one group $-C(=O)-$, and optionally having 1-3 double bonds;
Z is $A^3$, $-(CH_2)_{1-3}-CO_2R^8$, $-(CH_2)_{1-3}-C(O)NR^6R^7$, $-(CH_2)_{1-3}-SO_2NR^6R^7$, $-CO_2R^8$, $-C(O)NR^6R^7$, $-SO_2NR^6R^7$, or $-(CH_2)_{1-3}$-HET(2), wherein HET(2) is optionally substituted with 1-3 substituents which are independently $-C_{1-3}$alkyl optionally substituted with 1-5 halogens, $-OC_{1-3}$alkyl optionally substituted with 1-5 halogens, halogen or $NR^6R^7$;
$R^8$ is H or $-C_{1-3}$alkyl optionally substituted with 1-3 halogens;
$R^9$ is H or $-C_{1-5}$alkyl;
$A^3$ is phenyl, $C_3$-$C_6$ cycloalkyl optionally having 1-2 double bonds, or HET(1), wherein $A^3$ is optionally substituted with 1-3 groups which are each independently $CH_3$, $CF_3$, $-OCH_3$, $-OCF_3$, $-OH$, or halogen, and is optionally substituted with one group which is HET(2), $-(CH_2)_{1-2}-CO_2R^8$, $-(CH_2)_{1-2}-C(O)NR^6R^7$, $-(CH_2)_{1-2}-SO_2NR^6R^7$, $-CO_2R^8$, $-C(O)NR^6R^7$, $-SO_2NR^6R^7$, or $-C(O)NR^6$cyclopropyl, wherein cyclopropyl is optionally substituted with 1-3 substituents which are independently selected from 1-3 halogens, one $CH_3$, and one $-CN$, and HET(2) is optionally substituted with 1-3 groups which are each independently $CH_3$, $CF_3$, $-OCH_3$, $-OCF_3$, halogen, or $NR^6R^7$;
$A^2$ is phenyl or HET(1), wherein $A^2$ is substituted with 1-3 substituent groups which are each independently $CH_3$, $CF_3$, $-OCH_3$, $-OCF_3$, halogen, $-CN$, $-OH$, or $C_{3-4}$cycloalkyl optionally substituted with 1-3 substituents which are each independently halogen, $CF_3$, $CH_3$, $-OCF_3$, or $-OCH_3$; and
a is 0, 1, or 2.

4. The compound of claim 3, or a pharmaceutically acceptable salt thereof, wherein:
$R^1$ is $CH_3$, $CF_3$, $-OCH_3$, $-OCF_3$, F, Cl, or $-NR^6R^7$;
$R^6$ and $R^7$ are each independently H or $-C_1$-$C_3$ alkyl;
$D^1$ is $CR^2$, wherein $R^2$ is H, $-C_{1-3}$alkyl, F, or Cl;
$D^2$ is $CR^3$, wherein $R^3$ is H, $-C_{1-3}$alkyl, F, or Cl;
$D^3$ is $CR^4$, wherein $R^4$ is H, $-C_{1-3}$alkyl, F, or Cl;
$R^5$ is $CH_3$;
$A^1$ is phenyl, pyridinyl, pyrazinyl, pyrimidinyl, pyridazinyl, pyrazolyl, imidazolyl, isoxazolyl, thiazolyl, oxadiazolyl, thiadiazolyl, oxazolyl, pyrrolyl, thienyl, furyl, cyclopropyl, cyclobutyl, cyclohexyl, cyclohexenyl, cyclopentyl, or cyclopentenyl, wherein $A^1$ is optionally substituted with 1-3 groups which are each independently F, Cl, $-OCH_3$, $-OCF_3$, $-C_{1-3}$alkyl, $-CN$, or $CF_3$, and optionally one substituent group Z;
Z is $A^3$, $-CH_2CH_2CO_2R^8$, $-CH_2CH_2C(O)NR^6R^7$, $-CH_2CH_2SO_2NR^6R^7$, or $-CH_2CH_2$-HET(2), wherein HET(2) is optionally substituted with 1-2 substituent groups which are each independently $CH_3$, $CF_3$, $-OCH_3$, $-OCF_3$, halogen, or $NR^6R^7$;
$R^8$ is H or $-CH_3$;
$R^9$ is H or $-C_{1-3}$alkyl;
HET(2) is a 5-membered heterocyclic ring having 1-3 heteroatom groups which are each independently N, NH, O, or S, optionally having one group $-C(=O)$, and optionally having 1-3 double bonds;
$A^3$ is phenyl, cyclopropyl, cyclobutyl, cyclohexyl, cyclohexenyl, cyclopentyl, cyclopentenyl, or HET(1), wherein HET(1) is pyridinyl, pyrazinyl, pyrimidinyl, pyridazinyl, pyrazolyl, imidazolyl, isoxazolyl, thiazolyl, oxadiazolyl, thiadiazolyl, oxazolyl, pyrrolyl, thienyl, furyl, or a 5-6-membered heterocyclic ring having 1-2 heteroatom groups which are independently $-N-$, $-NH-$ or $-O-$, and optionally one $-C(=O)-$ group, wherein $A^3$ is optionally substituted with 1-2 groups which are each independently $CH_3$, $CF_3$, $-OCH_3$, $-OCF_3$, $-OH$, or halogen, and is optionally substituted with 1 group which is $-CO_2R^8$, $-C(O)NR^6R^7$, $-SO_2NR^6R^7$, HET(2), or $-C(O)NR^6$cyclopropyl wherein cyclopropyl is optionally substituted with 1-3 substituents which are independently selected from 1-3 halogens, one $CH_3$ and one $-CN$, and HET(2) is optionally substituted with 1-2 substituent groups which are each independently $CH_3$, $CF_3$, $-OCH_3$, $-OCF_3$, halogen, or $NR^6R^7$;
$A^2$ is phenyl or HET(1) wherein $A^2$ is substituted with 1-3 substituent groups which are each independently $CF_3$, $CH_3$, F, Cl, $-CN$, or cyclopropyl; and
a is 0 or 1.

5. The compound of claim 4 having Formula 1a, or a pharmaceutically acceptable salt thereof:

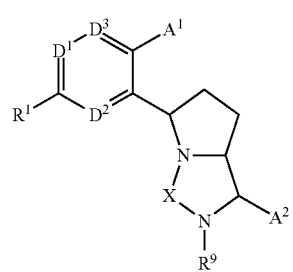

Ia wherein RI is $CF_3$, F, or $-N(CH_3)_2$;
$R^6$ and $R^7$ are each independently H or $-CH_3$;
$D^1$ is $CR^2$, wherein $R^2$ is H or $C_{1-3}$alkyl;
$D^2$ is $CR^3$, wherein $R^3$ is H or $CH_3$;
$D^3$ is $CR^4$, wherein $R^4$ is H or $CH_3$;
$A^1$ is phenyl, pyridinyl, thienyl, furyl, cyclohexenyl, or cyclopentenyl, wherein $A^1$ is optionally substituted with 1-3 groups which are each independently F, Cl, $-OCH_3$, isopropyl, $-CN$, $-CH_3$, or $CF_3$, and optionally one substituent group Z;
Z is $A^3$, $-CH_2CH_2CO_2R^8$, $-CH_2CH_2$-(5-oxo-4,5-dihydro-1,3,4-oxadiazol-2-yl), or $-CH_2CH_2$-(5-amino-1,3,4-oxadiazol-2-yl);

R⁸ is H or —CH₃;

R⁹ is H or —CH₃;

A³ is phenyl, cyclobutyl, cyclopentyl, cyclohexyl, or HET(1), wherein HET(1) is pyridinyl, 6-oxopiperidinyl, 2-oxo-1,3-oxazolidinyl, 2-oxo-1,3-oxazinanyl, 5-oxopyrrolidinyl, -(5-oxo-4,5-dihydro-1,3,4-oxadiazol-2-yl), or -(5-amino-1,3,4-oxadiazol-2-yl) wherein A³ is optionally substituted with 1-2 groups —CH₃, —OCH₃, or —OH, and is optionally substituted with 1 group which is —CO₂R⁸ or —C(=O)NHcyclopropyl which is optionally substituted with 1-3 groups independently selected from one —CN and 1-3 halogens; and A² is phenyl or pyridinyl, wherein A² is substituted with 1 or 2 groups which are each independently CF₃, CH₃, F, or Cl.

6. The compound of claim 5 having Formula 1a, or a pharmaceutically acceptable salt thereof, wherein R¹ is CF₃;

D¹ is CR², wherein R² is H;

D² is CR³, wherein R³ is H;

D³ is CR⁴, wherein R⁴ is H;

A¹ is phenyl or pyridinyl, wherein A¹ is optionally substituted with 1-3 groups which are each independently F, —OCH₃, or isopropyl, and optionally one substituent group Z;

Z is A³ or —CH₂CH₂CO₂R⁸;

R⁸ is H or —CH₃;

R⁹ is H or —CH₃;

A³ is phenyl, cyclohexyl, or HET(1), wherein HET(1) is pyridinyl or 5-oxopyrrolidinyl, wherein A³ is optionally substituted with 1-2 groups —CH₃ and is optionally substituted with 1 group which is —CO₂R⁸ or —C(=O)NHcyclopropyl which has a geminal —CN substituent on the cyclopropyl ring; and A² is phenyl or pyridinyl, wherein A² is substituted with 1-2 groups which are selected from CF₃ and F.

7. The compound of claim 6, or a pharmaceutically acceptable salt thereof, having the structure below:

67
-continued
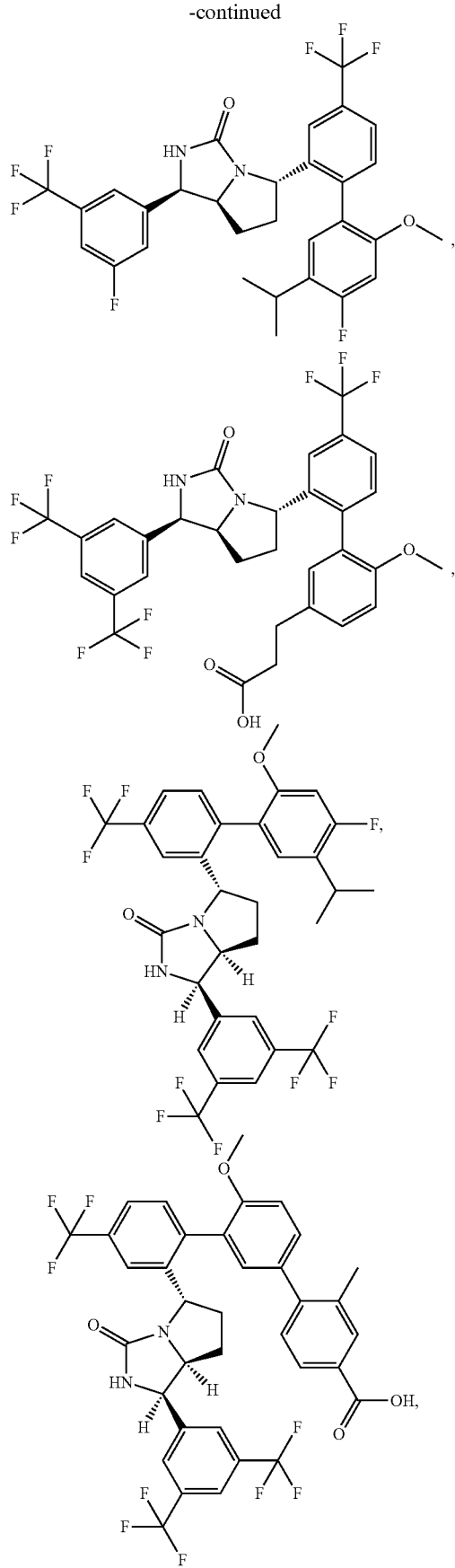
68
-continued
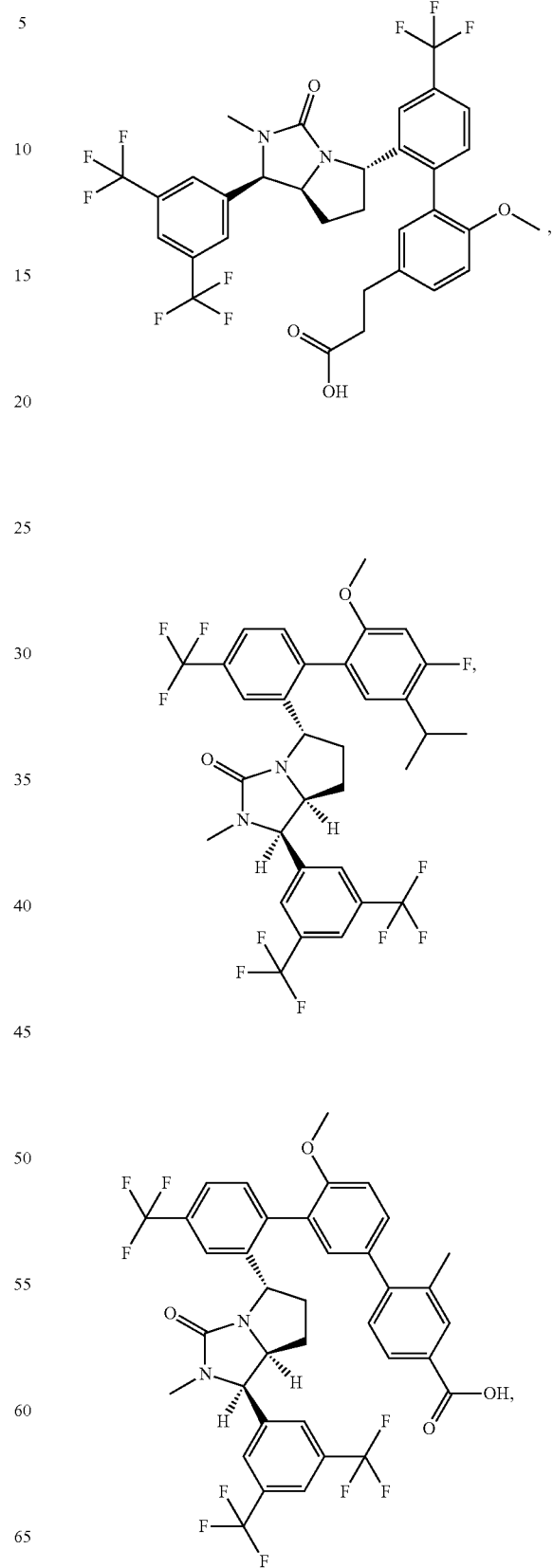

69
-continued
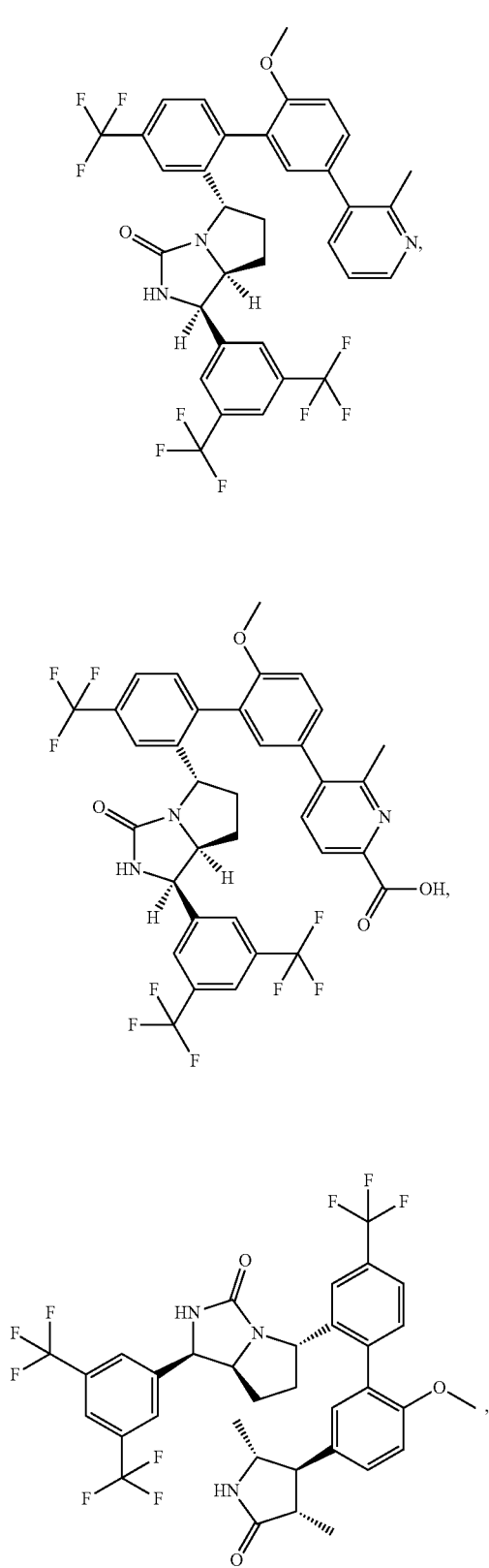
70
-continued
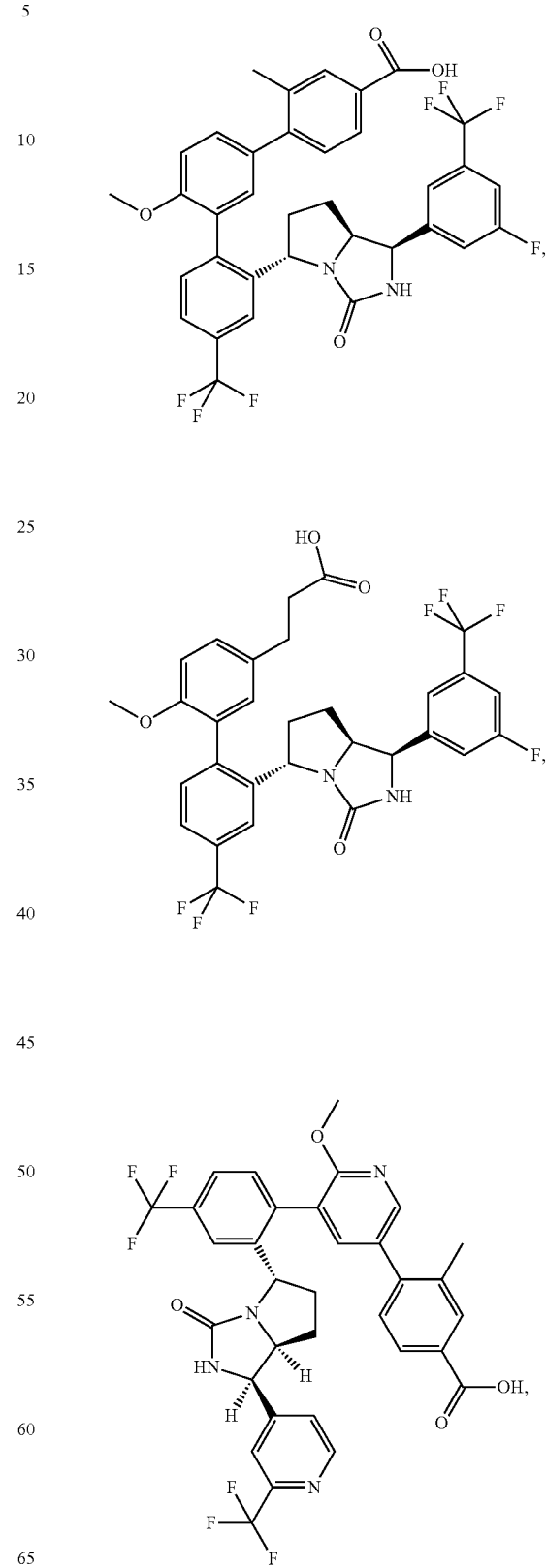

-continued

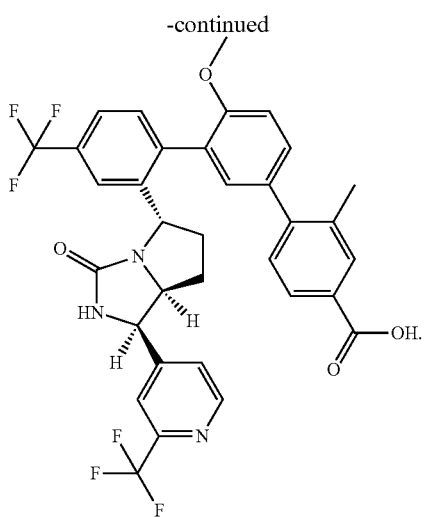

8. A pharmaceutical composition comprising the compound of claim 1 or a pharmaceutically acceptable salt thereof, and a pharmaceutically acceptable carrier.

9. A pharmaceutical composition comprising the compound of claim 1 or a pharmaceutically acceptable salt thereof, a pharmaceutically acceptable carrier, and one or more active ingredients selected from the group consisting of:
(i) HMG-CoA reductase inhibitors;
(ii) bile acid sequestrants;
(iii) niacin;
(iv) PPARα agonists;
(v) cholesterol absorption inhibitors;
(vi) acyl CoA:cholesterol acyltransferase (ACAT) inhibitors;
(vii) phenolic anti-oxidants;
(viii) microsomal triglyceride transfer protein (MTP)/ApoB secretion inhibitors;
(ix) anti-oxidant vitamins;
(x) thyromimetics;
(xi) LDL (low density lipoprotein) receptor inducers;
(xii) platelet aggregation inhibitors;
(xiii) vitamin B12 (also known as cyanocobalamin);
(xiv) folic acid or a pharmaceutically acceptable salt or ester thereof;
(xv) FXR and LXR ligands;
(xvi) agents that enhance ABCA1 gene expression;
(xvii) ileal bile acid transporters; and
(xviii) niacin receptor agonists.

10. The compound of claim 1, or a pharmaceutically acceptable salt thereof, having the structure below:

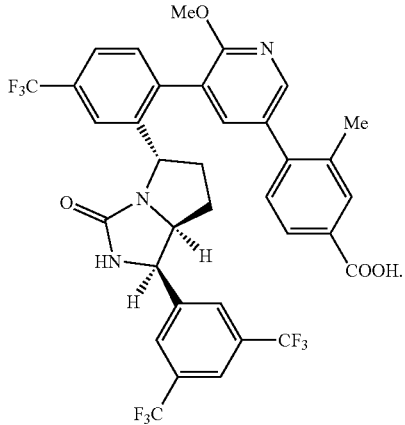 [SMILES: COc1ncc(-c2ccc(C(=O)O)cc2C)cc1-c1ccc(C(F)(F)F)cc1[C@@H]1CC[C@H]2[C@@H](c3cc(C(F)(F)F)cc(C(F)(F)F)c3)NC(=O)N12]

* * * * *